(12) United States Patent
Cojocaru et al.

(10) Patent No.: US 7,332,569 B2
(45) Date of Patent: Feb. 19, 2008

(54) BRAIN NATRIURETIC PEPTIDE SPLICED VARIANT

(75) Inventors: Gad S. Cojocaru, Ramat-HaSharon (IL); Alexander Diber, Rishon-LeZion (IL); Amit Novik, Beit-HaSharon (IL); Sarah Pollock, Tel-Aviv (IL); Zurit Levine, Herzlia (IL); Yossi Cohen, Banstead (GB); Michal Ayalon-Soffer, Ramat-HaSharon (IL)

(73) Assignee: Compugen Ltd., Tel Aviv (IL)

( * ) Notice: Subject to any disclaimer, the term of this patent is extended or adjusted under 35 U.S.C. 154(b) by 0 days.

(21) Appl. No.: 11/043,590

(22) Filed: Jan. 27, 2005

(65) Prior Publication Data

US 2005/0277156 A1    Dec. 15, 2005

Related U.S. Application Data

(60) Provisional application No. 60/539,127, filed on Jan. 27, 2004, provisional application No. 60/587,851, filed on Jul. 15, 2004, provisional application No. 60/607,246, filed on Sep. 7, 2004, provisional application No. 60/622,016, filed on Oct. 27, 2004.

(51) Int. Cl.
*C07K 14/435* (2006.01)

(52) U.S. Cl. .................................... 530/324

(58) Field of Classification Search .................. None
See application file for complete search history.

(56) References Cited

U.S. PATENT DOCUMENTS 5,948,761 A * 9/1999 Seilhamer et al. ............ 514/12

OTHER PUBLICATIONS

Alberts et al. Molecular Biology of the Cell, 3rd edition, 1994, p. 465.*
Fu et al. EMBO Journal, 1996, vol. 15, pp. 4392-4401.*
Bowie et al. Science, 1990, 257:1306-1310.*
Nature Genetics, 1999, 21:440-443.*
Burgess et al. J of Cell Bio. 111:2129-2138, 1990.*
Gustafsson, J. A., Eur J Cancer. Sep. 2000;36 Suppl 4:S16.*
Pawson et al. 2003, Science 300:445-452.*

* cited by examiner

*Primary Examiner*—Robert C. Hayes
*Assistant Examiner*—Chang-Yu Wang
(74) *Attorney, Agent, or Firm*—Staas & Halsey LLP

(57) ABSTRACT

Novel BNP variants. The novel BNP variants according to the present invention may optionally be used for diagnosis of a BNP variant-detectable disease as described herein.

1 Claim, 7 Drawing Sheets
(6 of 7 Drawing Sheet(s) Filed in Color)

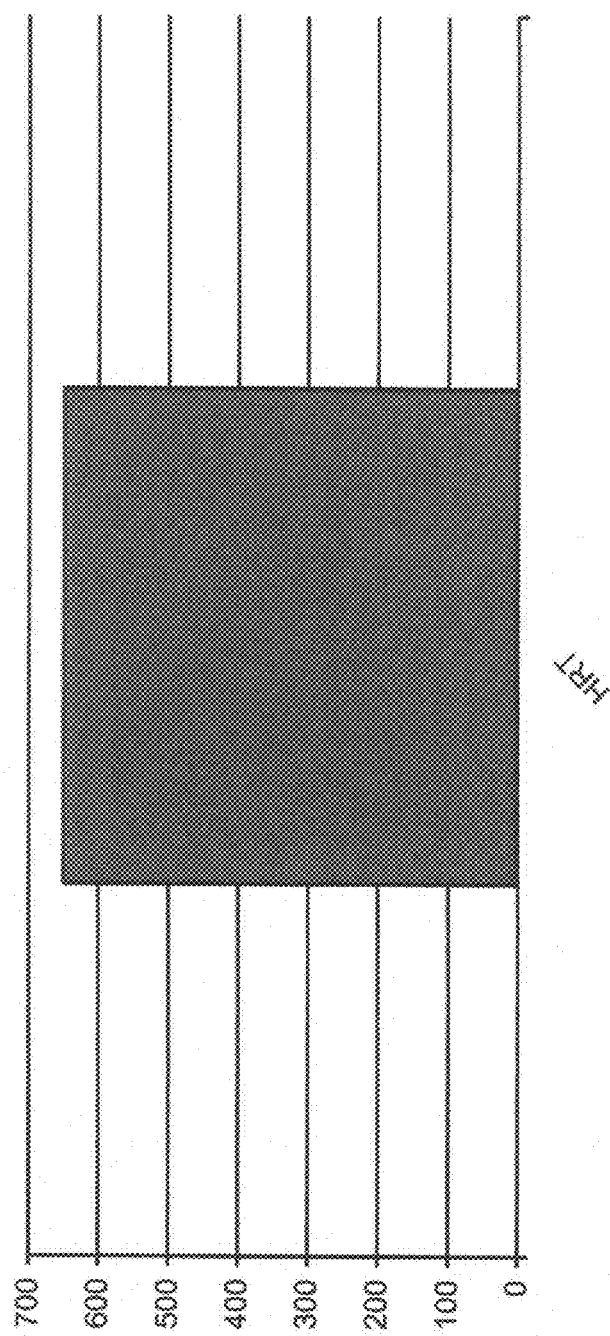

N-normal; F- fibrotic; Neg – negative control, no RT

SEQUENCE LISTING

<160> NUMBER OF SEQ ID NOS: 47

<210> SEQ ID NO 1
<211> LENGTH: 1396
<212> TYPE: DNA
<213> ORGANISM: Homo sapiens

<400> SEQUENCE: 1

```
aggcgcggag gggctcattc ccgggccctg atctcagagg cccggaatgt ggctgataaa      60
tcagagataa ccctgcatgg cagggcaggc ccgacactca gctccaggat aaaaggccac     120
ggtgtcccga ggagccagga ggagcacccc gcaggctgag ggcaggtggg aagcaaaccc     180
ggacgcatcg cagcagcagc agcagcagca gaagcagcag cagcagcctc cgcagtccct     240
ccagagacat ggatccccag acagcacctt cccgggcgct cctgctcctg ctcttcttgc     300
atctggcttt cctgggaggt cgttcccacc cgctgggcag ccccggttca gcctcggact     360
tggaaacgtc cgggttacag gagcagcgca accatttgca gggcaaactg tcggagctgc     420
```

-continued

| | |
|---|---|
| aggtggagca gacatccctg gagcccctcc aggagagccc ccgtcccaca ggtgtctgga | 480 |
| agtcccggga ggtagccacc gagggcatcc gtgggcaccg caaaatggtc ctctacaccc | 540 |
| tgcgggcacc acgaagcccc aagatggtgc aagggtctgg ctgctttggg aggaagatgg | 600 |
| accggatcag ctcctccagt ggcctgggct gcaaaggtaa gcaccccctg ccaccccggc | 660 |
| cgccttcccc cattccagtg tgtgacactg ttagagtcac tttggggttt gttgtctctg | 720 |
| ggaaccacac tctttgagaa aaggtcacct ggacatcgct tcctcttgtt aacagccttc | 780 |
| agggccaagg ggtgcctttg tggaattagt aaatgtgggc ttatttcatt accatgccca | 840 |
| caataccttc tccccacctc ctacttctta tcaaaggggc agaatctcct ttggggggtct | 900 |
| gtttatcatt tggcagcccc ccagtggtgc agaaagagaa ccaaacattt cctcctggtt | 960 |
| tcctctaaac tgtctatagt ctcaaaggca gagagcagga tcaccagagc aatgataatc | 1020 |
| cccaatttac agatgaggaa actgaggctc agagagttgc attaagcctc aaacgtctga | 1080 |
| tgactaacag ggtggtgggt ggcacacgat gaggtaagct cagcccctgc ctccatctcc | 1140 |
| caccctaacc atcatcaccc tctctctttc cctgacagtg ctgaggcggc attaagagga | 1200 |
| agtcctggct gcagacacct gcttctgatt ccacaagggg ctttttcctc aaccctgtgg | 1260 |
| ccgcctttga agtgactcat ttttttaatg tatttatgta tttatttgat tgttttatat | 1320 |
| aagatggttt cttacctttg agcacaaaat ttccacggtg aaataaagtc aacattataa | 1380 |
| gctttatctt ttgaaa | 1396 |

<210> SEQ ID NO 2
<211> LENGTH: 1086
<212> TYPE: DNA
<213> ORGANISM: Homo sapiens

<400> SEQUENCE: 2

| | |
|---|---|
| aggcgcggag gggctcattc ccgggccctg atctcagagg cccggaatgt ggctgataaa | 60 |
| tcagagataa ccctgcatgg cagggcaggc ccgacactca gctccaggat aaaaggccac | 120 |
| ggtgtcccga ggagccagga ggagcacccc gcaggctgag ggcaggtggg aagcaaaccc | 180 |
| ggacgcatcg cagcagcagc agcagcagca gaagcagcag cagcagcctc cgcagtccct | 240 |
| ccagagacat ggatccccag acagcacctt cccgggcgct cctgctcctg ctcttcttgc | 300 |
| atctggcttt cctgggaggt cgttcccacc cgctgggcag ccccggttca gcctcggact | 360 |
| tggaaacgtc cgggttacag gtgagagcgg agggcagctc aggggattg acagcagca | 420 |
| atgaaagggt cctcacctgc tgtcccaaga ggccctcatc tttcctttgg aattagtgat | 480 |
| aaaggaatca gaaaatggag agactgggtg ccctgaccct gtacccaagg cagtcggttc | 540 |
| acttgggtgc catgaagggc tggtgagccc aggggtgggt ccctgaggct ggacgcccc | 600 |
| cattcattgc aggagcagcg caaccatttg cagggcaaac tgtcggagct gcaggtggag | 660 |
| cagacatccc tggagcccct ccaggagagc cccgtcccca caggtgtctg gaagtcccgg | 720 |
| gaggtagcca ccgagggcat ccgtgggcac cgcaaaatgg tcctctacac cctgcgggca | 780 |
| ccacgaagcc ccaagatggt gcaagggtct ggctgctttg gaggaagat ggaccggatc | 840 |
| agctcctcca gtggcctggg ctgcaaagtg ctgaggcggc attaagagga agtcctggct | 900 |
| gcagacacct gcttctgatt ccacaagggg ctttttcctc aaccctgtgg ccgcctttga | 960 |
| agtgactcat ttttttaatg tatttatgta tttatttgat tgttttatat aagatggttt | 1020 |
| cttacctttg agcacaaaat ttccacggtg aaataaagtc aacattataa gctttatctt | 1080 |
| ttgaaa | 1086 |

<210> SEQ ID NO 3
<211> LENGTH: 1628
<212> TYPE: DNA
<213> ORGANISM: Homo sapiens

<400> SEQUENCE: 3

```
aggcgcggag gggctcattc ccgggccctg atctcagagg cccggaatgt ggctgataaa      60
tcagagataa ccctgcatgg cagggcaggc ccgacactca gctccaggat aaaaggccac     120
ggtgtcccga ggagccagga ggagcacccc gcaggctgag ggcaggtggg aagcaaaccc     180
ggacgcatcg cagcagcagc agcagcagca gaagcagcag cagcagcctc cgcagtccct     240
ccagagacat ggatcccag acagcacctt cccgggcgct cctgctcctg ctcttcttgc      300
atctggcttt cctgggaggt cgttcccacc cgctgggcag ccccggttca gcctcggact     360
tggaaacgtc cggggttacag gtgagagcgg agggcagctc aggggattg acagcagca      420
atgaaagggt cctcacctgc tgtcccaaga ggccctcatc tttcctttgg aattagtgat     480
aaaggaatca gaaatggag agactgggtg ccctgaccct gtacccaagg cagtcggttc      540
acttgggtgc catgaagggc tggtgagccc aggggtgggt ccctgaggct ggacgcccc      600
cattcattgc aggagcagcg caaccatttg cagggcaaac tgtcggagct gcaggtggag     660
cagacatccc tggagcccct ccaggagagc ccgtccca caggtgtctg gaagtcccgg       720
gaggtagcca ccgagggcat ccgtgggcac cgcaaaatgg tcctctacac cctgcgggca     780
ccacgaagcc ccaagatggt gcaagggtct ggctgctttg ggaggaagat ggaccggatc     840
agctcctcca gtggcctggg ctgcaaaggt aagcaccccc tgccaccccg gccgccttcc     900
cccattccag tgtgtgacac tgttagagtc actttggggt tgttgtctc tgggaaccac      960
actctttgag aaaaggtcac ctggacatcg cttcctcttg ttaacagcct tcagggccaa    1020
ggggtgcctt tgtggaatta gtaaatgtgg gcttatttca ttaccatgcc cacaatacct    1080
tctccccacc tcctacttct tatcaaaggg gcagaatctc ctttggggt ctgtttatca     1140
tttggcagcc cccagtggt gcagaaagag aaccaaacat ttcctcctgg tttcctctaa     1200
actgtctata gtctcaaagg cagagagcag gatcaccaga gcaatgataa tccccaattt    1260
acagatgagg aaactgaggc tcagagagtt gcattaagcc tcaaacgtct gatgactaac    1320
agggtggtgg gtggcacacg atgaggtaag ctcagcccct gcctccatct cccaccctaa    1380
ccatcatcac cctctctctt tccctgacag tgctgaggcg gcattaagag gaagtcctgg    1440
ctgcagacac ctgcttctga ttccacaagg ggcttttttcc tcaaccctgt ggccgccttt    1500
gaagtgactc atttttttaa tgtatttatg tatttatttg attgtttat ataagatggt     1560
ttcttacctt tgagcacaaa atttccacgg tgaaataaag tcaacattat aagctttatc    1620
ttttgaaa                                                             1628
```

<210> SEQ ID NO 4
<211> LENGTH: 586
<212> TYPE: DNA
<213> ORGANISM: Homo sapiens

<400> SEQUENCE: 4

```
aggcgcggag gggctcattc ccgggccctg atctcagagg cccggaatgt ggctgataaa      60
tcagagataa ccctgcatgg cagggcaggc ccgacactca gctccaggat aaaaggccac     120
ggtgtcccga ggagccagga ggagcacccc gcaggctgag ggcaggtggg aagcaaaccc     180
```

```
ggacgcatcg cagcagcagc agcagcagca gaagcagcag cagcagcctc cgcagtccct      240
ccgtgggcac cgcaaaatgg tcctctacac cctgcgggca ccacgaagcc ccaagatggt      300
gcaagggtct ggctgctttg ggaggaagat ggaccggatc agctcctcca gtggcctggg      360
ctgcaaagtg ctgaggcggc attaagagga agtcctggct gcagacacct gcttctgatt      420
ccacaagggg cttttcctc aaccctgtgg ccgcctttga agtgactcat ttttttaatg       480
tatttatgta tttatttgat tgttttatat aagatggttt cttacctttg agcacaaaat      540
ttccacggtg aaataaagtc aacattataa gctttatctt ttgaaa                     586

<210> SEQ ID NO 5
<211> LENGTH: 240
<212> TYPE: DNA
<213> ORGANISM: Artificial
<220> FEATURE:
<223> OTHER INFORMATION: Synthetic oligonucleotide

<400> SEQUENCE: 5
aggcgcggag gggctcattc ccgggccctg atctcagagg cccggaatgt ggctgataaa       60
tcagagataa ccctgcatgg cagggcaggc ccgacactca gctccaggat aaaaggccac      120
ggtgtcccga ggagccagga ggagcacccc gcaggctgag ggcaggtggg aagcaaaccc      180
ggacgcatcg cagcagcagc agcagcagca gaagcagcag cagcagcctc cgcagtccct      240

<210> SEQ ID NO 6
<211> LENGTH: 140
<212> TYPE: DNA
<213> ORGANISM: Artificial
<220> FEATURE:
<223> OTHER INFORMATION: Synthetic oligonucleotide

<400> SEQUENCE: 6
ccagagacat ggatccccag acagcacctt cccgggcgct cctgctcctg ctcttcttgc       60
atctggcttt cctgggaggt cgttcccacc cgctgggcag ccccggttca gcctcggact      120
tggaaacgtc cgggttacag                                                  140

<210> SEQ ID NO 7
<211> LENGTH: 232
<212> TYPE: DNA
<213> ORGANISM: Artificial
<220> FEATURE:
<223> OTHER INFORMATION: Synthetic oligonucleotide

<400> SEQUENCE: 7
gtgagagcgg agggcagctc aggggattg gacagcagca atgaaagggt cctcacctgc        60
tgtcccaaga ggccctcatc tttcctttgg aattagtgat aaaggaatca gaaaatggag      120
agactgggtg ccctgaccct gtacccaagg cagtcggttc acttgggtgc catgaagggc      180
tggtgagccc aggggtgggt ccctgaggct tggacgcccc cattcattgc ag              232

<210> SEQ ID NO 8
<211> LENGTH: 128
<212> TYPE: DNA
<213> ORGANISM: Artificial
<220> FEATURE:
<223> OTHER INFORMATION: Synthetic oligonucleotide

<400> SEQUENCE: 8
gagcagcgca accatttgca gggcaaactg tcggagctgc aggtggagca gacatccctg       60
gagcccctcc aggagagccc ccgtcccaca ggtgtctgga agtcccggga ggtagccacc      120
``` gagggcat                                                                128

<210> SEQ ID NO 9
<211> LENGTH: 128
<212> TYPE: DNA
<213> ORGANISM: Artificial
<220> FEATURE:
<223> OTHER INFORMATION: Synthetic oligonucleotide

<400> SEQUENCE: 9
ccgtgggcac cgcaaaatgg tcctctacac cctgcgggca ccacgaagcc ccaagatggt      60
gcaagggtct ggctgctttg ggaggaagat ggaccggatc agctcctcca gtggcctggg     120
ctgcaaag                                                              128

<210> SEQ ID NO 10
<211> LENGTH: 542
<212> TYPE: DNA
<213> ORGANISM: Artificial
<220> FEATURE:
<223> OTHER INFORMATION: Synthetic oligonucleotide

<400> SEQUENCE: 10
gtaagcaccc cctgccaccc cggccgcctt cccccattcc agtgtgtgac actgttagag      60
tcactttggg gtttgttgtc tctgggaacc acactctttg agaaaaggtc acctggacat     120
cgcttcctct tgttaacagc cttcagggcc aaggggtgcc tttgtggaat tagtaaatgt     180
gggcttattt cattaccatg cccacaatac cttctcccca cctcctactt cttatcaaag     240 ggcagaatc tcctttgggg gtctgtttat catttggcag cccccagtg gtgcagaaag       300 agaaccaaac atttcctcct ggtttcctct aaactgtcta tagtctcaaa ggcagagagc     360
aggatcacca gagcaatgat aatccccaat ttacagatga ggaaactgag gctcagagag     420
ttgcattaag cctcaaacgt ctgatgacta acagggtggt gggtggcaca cgatgaggta     480
agctcagccc ctgcctccat ctcccaccct aaccatcatc accctctctc tttccctgac     540
ag                                                                    542

<210> SEQ ID NO 11
<211> LENGTH: 218
<212> TYPE: DNA
<213> ORGANISM: Artificial
<220> FEATURE:
<223> OTHER INFORMATION: Synthetic oligonucleotide

<400> SEQUENCE: 11
tgctgaggcg gcattaagag gaagtcctgg ctgcagacac ctgcttctga ttccacaagg      60 ggcttttttcc tcaaccctgt ggccgccttt gaagtgactc attttttttaa tgtatttatg    120 tatttatttg attgttttat ataagatggt ttcttacctt tgagcacaaa atttccacgg     180
tgaaataaag tcaacattat aagctttatc ttttgaaa                             218

<210> SEQ ID NO 12
<211> LENGTH: 134
<212> TYPE: PRT
<213> ORGANISM: Homo sapiens

<400> SEQUENCE: 12

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro

-continued

```
                    20                  25                  30

Gly Ser Ala Ser Asp Leu Glu Thr Ser Gly Leu Gln Glu Gln Arg Asn
            35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Gly Leu Gly Cys
        115                 120                 125

Lys Val Leu Arg Arg His
    130
```

<210> SEQ ID NO 13
<211> LENGTH: 162
<212> TYPE: PRT
<213> ORGANISM: Homo sapiens

<400> SEQUENCE: 13

```
Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
                20                  25                  30

Gly Ser Ala Ser Asp Leu Glu Thr Ser Gly Leu Gln Glu Gln Arg Asn
            35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Gly Leu Gly Cys
        115                 120                 125

Lys Gly Lys His Pro Leu Pro Pro Arg Pro Ser Pro Ile Pro Val
    130                 135                 140

Cys Asp Thr Val Arg Val Thr Leu Gly Phe Val Val Ser Gly Asn His
145                 150                 155                 160

Thr Leu
```

<210> SEQ ID NO 14
<211> LENGTH: 75
<212> TYPE: PRT
<213> ORGANISM: Homo sapiens

<400> SEQUENCE: 14

```
Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
                20                  25                  30

Gly Ser Ala Ser Asp Leu Glu Thr Ser Gly Leu Gln Val Arg Ala Glu
            35                  40                  45
```

Gly Ser Ser Gly Gly Leu Asp Ser Ser Asn Glu Arg Val Leu Thr Cys
        50                  55                  60

Cys Pro Lys Arg Pro Ser Ser Phe Leu Trp Asn
 65                  70                  75

<210> SEQ ID NO 15
<211> LENGTH: 42
<212> TYPE: PRT
<213> ORGANISM: Homo sapiens

<400> SEQUENCE: 15

Met Val Leu Tyr Thr Leu Arg Ala Pro Arg Ser Pro Lys Met Val Gln
  1               5                  10                  15

Gly Ser Gly Cys Phe Gly Arg Lys Met Asp Arg Ile Ser Ser Ser
             20                  25                  30

Gly Leu Gly Cys Lys Val Leu Arg Arg His
         35                  40

<210> SEQ ID NO 16
<211> LENGTH: 60
<212> TYPE: PRT
<213> ORGANISM: Homo sapiens

<400> SEQUENCE: 16

Ser Pro Lys Met Val Gln Gly Ser Gly Cys Phe Gly Arg Lys Met Asp
  1               5                  10                  15

Arg Ile Ser Ser Ser Ser Gly Leu Gly Cys Lys Gly Lys His Pro Leu
             20                  25                  30

Pro Pro Arg Pro Pro Ser Pro Ile Pro Val Cys Asp Thr Val Arg Val
             35                  40                  45

Thr Leu Gly Phe Val Val Ser Gly Asn His Thr Leu
         50                  55                  60

<210> SEQ ID NO 17
<211> LENGTH: 32
<212> TYPE: PRT
<213> ORGANISM: Homo sapiens

<400> SEQUENCE: 17

Ser Pro Lys Met Val Gln Gly Ser Gly Cys Phe Gly Arg Lys Met Asp
  1               5                  10                  15

Arg Ile Ser Ser Ser Ser Gly Leu Gly Cys Lys Val Leu Arg Arg His
             20                  25                  30

<210> SEQ ID NO 18
<211> LENGTH: 20
<212> TYPE: DNA
<213> ORGANISM: Artificial
<220> FEATURE:
<223> OTHER INFORMATION: Synthetic oligonucleotide

<400> SEQUENCE: 18
cttcccccat tccagtgtgt                                              20

<210> SEQ ID NO 19
<211> LENGTH: 20
<212> TYPE: DNA
<213> ORGANISM: Artificial
<220> FEATURE:
<223> OTHER INFORMATION: Synthetic oligonucleotide

<400> SEQUENCE: 19

```
gaggaagcga tgtccaggtg                                              20

<210> SEQ ID NO 20
<211> LENGTH: 102
<212> TYPE: DNA
<213> ORGANISM: Artificial
<220> FEATURE:
<223> OTHER INFORMATION: Synthetic oligonucleotide

<400> SEQUENCE: 20
cttcccccat tccagtgtgt gacactgtta gagtcacttt ggggtttgtt gtctctggga   60
accacactct ttgagaaaag gtcacctgga catcgcttcc tc                     102

<210> SEQ ID NO 21
<211> LENGTH: 20
<212> TYPE: DNA
<213> ORGANISM: Artificial
<220> FEATURE:
<223> OTHER INFORMATION: Synthetic oligonucleotide

<400> SEQUENCE: 21
gcagcaatga aagggtcctc                                              20

<210> SEQ ID NO 22
<211> LENGTH: 19
<212> TYPE: DNA
<213> ORGANISM: Artificial
<220> FEATURE:
<223> OTHER INFORMATION: Synthetic oligonucleotide

<400> SEQUENCE: 22
catggcaccc aagtgaacc                                               19

<210> SEQ ID NO 23
<211> LENGTH: 140
<212> TYPE: DNA
<213> ORGANISM: Artificial
<220> FEATURE:
<223> OTHER INFORMATION: Synthetic oligonucleotide

<400> SEQUENCE: 23
gcagcaatga aagggtcctc acctgctgtc ccaagaggcc ctcatctttc ctttggaatt   60
agtgataaag gaatcagaaa atggagagac tgggtgccct gaccctgtac ccaaggcagt  120
cggttcactt gggtgccatg                                              140

<210> SEQ ID NO 24
<211> LENGTH: 20
<212> TYPE: DNA
<213> ORGANISM: Artificial
<220> FEATURE:
<223> OTHER INFORMATION: Synthetic oligonucleotide

<400> SEQUENCE: 24
gtccgggtta caggagcagc                                              20

<210> SEQ ID NO 25
<211> LENGTH: 19
<212> TYPE: DNA
<213> ORGANISM: Artificial
<220> FEATURE:
<223> OTHER INFORMATION: Synthetic oligonucleotide

<400> SEQUENCE: 25
```

```
ccgcctcagc actttgcag                                                 19
```

<210> SEQ ID NO 26
<211> LENGTH: 280
<212> TYPE: DNA
<213> ORGANISM: Artificial
<220> FEATURE:
<223> OTHER INFORMATION: Synthetic oligonucleotide

<400> SEQUENCE: 26

```
gtccgggtta caggagcagc gcaaccattt gcagggcaaa ctgtcggagc tgcaggtgga    60
gcagacatcc ctggagcccc tccaggagag ccccgtccc acaggtgtct ggaagtcccg    120
ggaggtagcc accgagggca tccgtgggca ccgcaaaatg gtcctctaca ccctgcgggc   180
accacgaagc cccaagatgg tgcaagggtc tggctgcttt gggaggaaga tggaccggat   240
cagctcctcc agtggcctgg gctgcaaagt gctgaggcgg                         280
```

<210> SEQ ID NO 27
<211> LENGTH: 20
<212> TYPE: DNA
<213> ORGANISM: Artificial
<220> FEATURE:
<223> OTHER INFORMATION: Synthetic oligonucleotide

<400> SEQUENCE: 27

```
gttcagcctc ggacttggaa                                                20
```

<210> SEQ ID NO 28
<211> LENGTH: 26
<212> TYPE: DNA
<213> ORGANISM: Artificial
<220> FEATURE:
<223> OTHER INFORMATION: Synthetic oligonucleotide

<400> SEQUENCE: 28

```
gtgactctaa cagtgtcaca cactgg                                         26
```

<210> SEQ ID NO 29
<211> LENGTH: 21
<212> TYPE: DNA
<213> ORGANISM: Artificial
<220> FEATURE:
<223> OTHER INFORMATION: Synthetic oligonucleotide

<400> SEQUENCE: 29

```
ccttgtggaa tcagaagcag g                                              21
```

<210> SEQ ID NO 30
<211> LENGTH: 23
<212> TYPE: DNA
<213> ORGANISM: Artificial
<220> FEATURE:
<223> OTHER INFORMATION: Synthetic oligonucleotide

<400> SEQUENCE: 30

```
tggcaagaag aaggtctggt tag                                            23
```

<210> SEQ ID NO 31
<211> LENGTH: 22
<212> TYPE: DNA
<213> ORGANISM: Artificial
<220> FEATURE:
<223> OTHER INFORMATION: Synthetic oligonucleotide

<400> SEQUENCE: 31
tgatcagccc atctttgatg ag                                              22

<210> SEQ ID NO 32
<211> LENGTH: 101
<212> TYPE: DNA
<213> ORGANISM: Artificial
<220> FEATURE:
<223> OTHER INFORMATION: Synthetic oligonucleotide

<400> SEQUENCE: 32
tggcaagaag aaggtctggt tagaccccaa tgagaccaat gaaatcgcca atgccaactc     60
ccgtcagcag atccggaagc tcatcaaaga tgggctgatc a                        101

<210> SEQ ID NO 33
<211> LENGTH: 20
<212> TYPE: DNA
<213> ORGANISM: Artificial
<220> FEATURE:
<223> OTHER INFORMATION: Synthetic oligonucleotide

<400> SEQUENCE: 33
cggtttgctg cggtaatcat                                                 20

<210> SEQ ID NO 34
<211> LENGTH: 21
<212> TYPE: DNA
<213> ORGANISM: Artificial
<220> FEATURE:
<223> OTHER INFORMATION: Synthetic oligonucleotide

<400> SEQUENCE: 34
tttcttgctg ccagtctgga c                                               21

<210> SEQ ID NO 35
<211> LENGTH: 122
<212> TYPE: DNA
<213> ORGANISM: Artificial
<220> FEATURE:
<223> OTHER INFORMATION: Synthetic oligonucleotide

<400> SEQUENCE: 35
cggtttgctg cggtaatcat gaggataaga gagccacgaa ccacggcact gattttcagt     60
tctgggaaaa tggtgtgcac aggagccaag agtgaagaac agtccagact ggcagcaaga    120
aa                                                                   122

<210> SEQ ID NO 36
<211> LENGTH: 19
<212> TYPE: DNA
<213> ORGANISM: Artificial
<220> FEATURE:
<223> OTHER INFORMATION: Synthetic oligonucleotide

<400> SEQUENCE: 36
atttgggtcg cggttcttg                                                  19

<210> SEQ ID NO 37
<211> LENGTH: 21
<212> TYPE: DNA
<213> ORGANISM: Artificial
<220> FEATURE:
<223> OTHER INFORMATION: Synthetic oligonucleotide

<400> SEQUENCE: 37

```
tgccttgaca ttctcgatgg t                                              21

<210> SEQ ID NO 38
<211> LENGTH: 133
<212> TYPE: DNA
<213> ORGANISM: Artificial
<220> FEATURE:
<223> OTHER INFORMATION: Synthetic oligonucleotide

<400> SEQUENCE: 38
atttgggtcg cggttcttgt tgtggatcg ctgtgatcgt cacttgacaa tgcagatctt    60
cgtgaagact ctgactggta agaccatcac cctcgaggtt gagcccagtg acaccatcga  120
gaatgtcaag gca                                                     133

<210> SEQ ID NO 39
<211> LENGTH: 20
<212> TYPE: DNA
<213> ORGANISM: Artificial
<220> FEATURE:
<223> OTHER INFORMATION: Synthetic oligonucleotide

<400> SEQUENCE: 39
tgggaacaag agggcatctg                                                20

<210> SEQ ID NO 40
<211> LENGTH: 22
<212> TYPE: DNA
<213> ORGANISM: Artificial
<220> FEATURE:
<223> OTHER INFORMATION: Synthetic oligonucleotide

<400> SEQUENCE: 40
ccaccactgc atcaaattca tg                                             22

<210> SEQ ID NO 41
<211> LENGTH: 86
<212> TYPE: DNA
<213> ORGANISM: Artificial
<220> FEATURE:
<223> OTHER INFORMATION: Synthetic oligonucleotide

<400> SEQUENCE: 41
tgggaacaag agggcatctg ctaaagtttc agattccatt tctgctcagt atccagtagt    60
ggatcatgaa tttgatgcag tggtgg                                         86

<210> SEQ ID NO 42
<211> LENGTH: 30
<212> TYPE: PRT
<213> ORGANISM: Artificial
<220> FEATURE:
<223> OTHER INFORMATION: Synthetic peptide

<400> SEQUENCE: 42

Gly Lys His Pro Leu Pro Pro Arg Pro Pro Ser Pro Ile Pro Val Cys
1               5                   10                  15

Asp Thr Val Arg Val Thr Leu Gly Phe Val Val Ser Gly Asn
            20                  25                  30

<210> SEQ ID NO 43
<211> LENGTH: 31
<212> TYPE: PRT
<213> ORGANISM: Artificial
<220> FEATURE:
<223> OTHER INFORMATION: Synthetic peptide
```

<400> SEQUENCE: 43

Val Arg Ala Glu Gly Ser Ser Gly Gly Leu Asp Ser Ser Asn Glu Arg
1               5                   10                  15

Val Leu Thr Cys Cys Pro Lys Arg Pro Ser Ser Phe Leu Trp Asn
            20                  25                  30

<210> SEQ ID NO 44
<211> LENGTH: 748
<212> TYPE: DNA
<213> ORGANISM: Homo sapiens

<400> SEQUENCE: 44

| | | | | | |
|---|---|---|---|---|---|
| gcagataatg | ggaggagccg | ggcccgagcg | agctctttcc | tttcgctgct | gcggccgcag | 60 |
| ccatgagtat | gctcaggctt | cagaagaggc | tcgcctctag | tgtcctccgc | tgtggcaaga | 120 |
| agaaggtctg | gttagacccc | aatgagacca | atgaaatcgc | caatgccaac | tcccgtcagc | 180 |
| agatccggaa | gctcatcaaa | gatgggctga | tcatccgcaa | gcctgtgacg | gtccattccc | 240 |
| gggctcgatg | ccggaaaaac | accttggccc | gccggaaggg | caggcacatg | gcataggta | 300 |
| agcggaaggg | tacagccaat | gcccgaatgc | agagaaggt | cacatggatg | aggagaatga | 360 |
| ggattttgcg | ccggctgctc | agaagatacc | gtgaatctaa | gaagatcgat | cgccacatgt | 420 |
| atcacagcct | gtacctgaag | gtgaagggga | atgtgttcaa | aaacaagcgg | attctcatgg | 480 |
| aacacatcca | caagctgaag | gcagacaagg | cccgcaagaa | gctcctggct | gaccaggctg | 540 |
| aggcccgcag | gtctaagacc | aaggaagcac | gcaagcgccg | tgaagagcgc | ctccaggcca | 600 |
| agaaggagga | gatcatcaag | actttatcca | aggaggaaga | gaccaagaaa | taaaacctcc | 660 |
| cactttgtct | gtacatactg | gcctctgtga | ttacatagat | cagccattaa | aataaaacaa | 720 |
| gccttaatct | gcaaaaaaaa | aaaaaaaa | | | | 748 |

<210> SEQ ID NO 45
<211> LENGTH: 1867
<212> TYPE: DNA
<213> ORGANISM: Homo sapiens

<400> SEQUENCE: 45

| | | | | | |
|---|---|---|---|---|---|
| ggttcgctgt | ggcgggcgcc | tgggccgccg | gctgtttaac | ttcgcttccg | ctggcccata | 60 |
| gtgatctttg | cagtgaccca | gcagcatcac | tgtttcttgg | cgtgtgaaga | taacccaagg | 120 |
| aattgaggaa | gttgctgaga | agagtgtgct | ggagatgctc | taggaaaaaa | ttgaatagtg | 180 |
| agacgagttc | cagcgcaagg | gtttctggtt | tgccaagaag | aaagtgaaca | tcatggatca | 240 |
| gaacaacagc | ctgccaccctt | acgctcaggg | cttggcctcc | cctcagggtg | ccatgactcc | 300 |
| cggaatccct | atctttagtc | caatgatgcc | ttatggcact | ggactgaccc | cacagcctat | 360 |
| tcagaacacc | aatagtctgt | ctattttgga | agagcaacaa | aggcagcagc | agcaacaaca | 420 |
| acagcagcag | cagcagcagc | agcagcaaca | gcaacagcag | cagcagcagc | agcagcagca | 480 |
| gcagcagcag | cagcagcagc | agcagcagca | gcaacaggca | gtggcagctg | cagccgttca | 540 |
| gcagtcaacg | tcccagcagg | caacacaggg | aacctcaggc | caggcaccac | agctcttcca | 600 |
| ctcacagact | ctcacaactg | cacccttgcc | gggcaccact | ccactgtatc | cctcccccat | 660 |
| gactcccatg | acccccatca | ctcctgccac | gccagcttcg | gagagttctg | ggattgtacc | 720 |
| gcagctgcaa | aatattgtat | ccacagtgaa | tcttggttgt | aaacttgacc | taaagaccat | 780 |
| tgcacttcgt | gcccgaaacg | ccgaatataa | tcccaagcgg | tttgctgcgg | taatcatgag | 840 |

-continued

| | |
|---|---|
| gataagagag ccacgaacca cggcactgat tttcagttct gggaaaatgg tgtgcacagg | 900 |
| agccaagagt gaagaacagt ccagactggc agcaagaaaa tatgctagag ttgtacagaa | 960 |
| gttgggtttt ccagctaagt tcttggactt caagattcag aatatggtgg ggagctgtga | 1020 |
| tgtgaagttt cctataaggt tagaaggcct tgtgctcacc caccaacaat ttagtagtta | 1080 |
| tgagccagag ttatttcctg gtttaatcta cagaatgatc aaaccagaa ttgttctcct | 1140 |
| tattttgtt tctggaaaag ttgtattaac aggtgctaaa gtcagagcag aaatttatga | 1200 |
| agcatttgaa aacatctacc ctattctaaa gggattcagg aagacgacgt aatggctctc | 1260 |
| atgtacccett gcctccccca cccccttctt ttttttttt taaacaaatc agtttgtttt | 1320 |
| ggtacctta aatggtggtg ttgtgagaag atggatgttg agttgcaggg tgtggcacca | 1380 |
| ggtgatgccc ttctgtaagt gcccaccgcg ggatgccggg aagggcatt atttgtgcac | 1440 |
| tgagaacacc gcgcagcgtg actgtgagtt gctcataccg tgctgctatc tgggcagcgc | 1500 |
| tgcccattta tttatatgta gattttaaac actgctgttg acaagttggt ttgagggaga | 1560 |
| aaactttaag tgttaaagcc acctctataa ttgattggac tttttaattt taatgttttt | 1620 |
| ccccatgaac cacagttttt atatttctac cagaaaagta aaaatctttt ttaaaagtgt | 1680 |
| tgttttcta atttataact cctaggggtt atttctgtgc cagacacatt ccacctctcc | 1740 |
| agtattgcag gacagaatat atgtgttaat gaaaatgaat ggctgtacat attttttct | 1800 |
| ttcttcagag tactctgtac aataaatgca gtttataaaa gtgttaaaaa aaaaaaaaa | 1860 |
| aaaaaaa | 1867 |

```
<210> SEQ ID NO 46
<211> LENGTH: 2201
<212> TYPE: DNA
<213> ORGANISM: Homo sapiens

<400> SEQUENCE: 46
```

| | |
|---|---|
| cgggatttgg gtcgcggttc ttgtttgtgg atcgctgtga tcgtcacttg acaatgcaga | 60 |
| tcttcgtgaa gactctgact ggtaagacca tcaccctcga ggttgagccc agtgacacca | 120 |
| tcgagaatgt caaggcaaag atccaagata aggaaggcat ccctcctgac cagcagaggc | 180 |
| tgatctttgc tggaaaacag ctggaagatg ggcgcaccct gtctgactac aacatccaga | 240 |
| agagtccac cctgcacctg gtgctccgtc tcagaggtgg gatgcaaatc ttcgtgaaga | 300 |
| cactcactgg caagaccatc acccttgagg tggagcccag tgacaccatc gagaacgtca | 360 |
| aagcaaagat ccaggacaag gaaggcattc ctcctgacca gcagaggttg atctttgccg | 420 |
| gaaagcagct ggaagatggg cgcaccctgt ctgactacaa catccagaaa gagtctaccc | 480 |
| tgcacctggt gctccgtctc agaggtggga tgcagatctt cgtgaagacc ctgactggta | 540 |
| agaccatcac cctcgaggtg gagcccagtg accatcga atgtcaag gcaaagatcc | 600 |
| aagataagga aggcattcct cctgatcagc agaggttgat ctttgccgga aaacagctgg | 660 |
| aagatggtcg taccctgtct gactacaaca tccagaaaga gtccaccttg cacctggtac | 720 |
| tccgtctcag aggtgggatg caaatcttcg tgaagacact cactggcaag accatcaccc | 780 |
| ttgaggtcga gcccagtgac actatcgaga cgtcaaagc aaagatccaa gacaaggaag | 840 |
| gcattcctcc tgaccagcag aggttgatct ttgccggaaa gcagctggaa gatgggcgca | 900 |
| ccctgtctga ctacaacatc cagaaagagt ctaccctgca cctggtgctc cgtctcagag | 960 |
| gtgggatgca gatcttcgtg aagacccctga ctggtaagac catcaccctc gaagtggagc | 1020 |
| cgagtgacac cattgagaat gtcaaggcaa agatccaaga caaggaaggc atccctcctg | 1080 |

-continued

```
accagcagag gttgatcttt gccggaaaac agctggaaga tggtcgtacc ctgtctgact    1140
acaacatcca gaaagagtcc accttgcacc tggtgctccg tctcagaggt gggatgcaga    1200
tcttcgtgaa gaccctgact ggtaagacca tcactctcga ggtggagccg agtgacacca    1260
ttgagaatgt caaggcaaag atccaagaca aggaaggcat ccctcctgat cagcagaggt    1320
tgatctttgc tgggaaacag ctggaagatg acgcaccct gtctgactac aacatccaga    1380
aagagtccac cctgcacctg gtgctccgtc ttagaggtgg gatgcagatc ttcgtgaaga    1440
ccctgactgg taagaccatc actctcgaag tggagccgag tgacaccatt gagaatgtca    1500
aggcaaagat ccaagacaag gaaggcatcc ctcctgacca gcagaggttg atctttgctg    1560
ggaaacagct ggaagatgga cgcaccctgt ctgactacaa catccagaaa gagtccaccc    1620
tgcacctggt gctccgtctt agaggtggga tgcagatctt cgtgaagacc ctgactggta    1680
agaccatcac tctcgaagtg gagccgagtg acaccattga gaatgtcaag gcaaagatcc    1740
aagacaagga aggcatccct cctgaccagc agaggttgat ctttgctggg aaacagctgg    1800
aagatggacg caccctgtct gactacaaca tccagaaaga gtccaccctg cacctggtgc    1860
tccgtctcag aggtgggatg cagatcttcg tgaagaccct gactggtaag accatcaccc    1920
tcgaggtgga gcccagtgac accatcgaga atgtcaaggc aaagatccaa gataaggaag    1980
gcatccctcc tgatcagcag aggttgatct ttgctgggaa acagctggaa gatggacgca    2040
ccctgtctga ctacaacatc cagaaagagt ccactctgca cttggtcctg cgcttgaggg    2100
ggggtgtcta agtttcccct tttaaggttt caacaaattt cattgcactt tcctttcaat    2160
aaagttgttg cattcccaaa aaaaaaaaaa aaaaaaaaa a                         2201
```

<210> SEQ ID NO 47
<211> LENGTH: 2277
<212> TYPE: DNA
<213> ORGANISM: Homo sapiens

<400> SEQUENCE: 47

```
gactgcgcgg cggcaacagc agacatgtcg ggggtccggg gcctgtcgcg gctgctgagc     60
gctcggcgcc tggcgctggc caaggcgtgg ccaacagtgt tgcaaacagg aacccgaggt    120
tttcacttca ctgttgatgg gaacaagagg gcatctgcta aagtttcaga ttccatttct    180
gctcagtatc cagtagtgga tcatgaattt gatgcagtgg tggtaggcgc tggaggggca    240
ggcttgcgag ctgcatttgg cctttctgag gcagggttta atacagcatg tgttaccaag    300
ctgtttccta ccaggtcaca cactgttgca gcgcagggag gaatcaatgc tgctctgggg    360
aacatggagg aggacaactg gaggtggcat ttctacgaca ccgtgaaggg ctccgactgg    420
ctgggggacc aggatgccat ccactacatg acggagcagg ccccgccgc cgtggtcgag    480 ctagaaaatt atggcatgcc gtttagcaga actgaagatg ggaagattta tcagcgtgca    540
tttggtggac agagcctcaa gttttggaaag ggcgggcagg cccatcggtg ctgctgtgtg    600
gctgatcgga ctggccactc gctattgcac accttatatg gacggtctct gcgatatgat    660
accagctatt ttgtggagta ttttgccttg gatctcctga tggagaacgg ggagtgccgt    720
ggtgtcatcg cactgtgcat agaggacggg tccatccatc gcataagagc aaagaacact    780
gttgttgcca caggaggcta cgggcgcacc tacttcagct gcacgtctgc ccacaccagc    840
actggcgacg gcacggccat gatcaccagg gcaggcctttc cttgccagga cctagagttt    900
gttcagttcc accccacagg catatatggt gctggttgtc tcattacgga aggatgtcgt    960
```

-continued

```
ggagagggag gcattctcat taacagtcaa ggcgaaaggt ttatggagcg atacgcccct    1020
gtcgcgaagg acctggcgtc tagagatgtg gtgtctcggt cgatgactct ggagatccga    1080
gaaggaagag gctgtggccc tgagaaagat cacgtctacc tgcagctgca ccacctacct    1140
ccagagcagc tggccacgcg cctgcctggc atttcagaga cagccatgat cttcgctggc    1200
gtggacgtca cgaaggagcc gatccctgtc ctccccaccg tgcattataa catgggcggc    1260
attcccacca actacaaggg gcaggtcctg aggcacgtga atggccagga tcagattgtg    1320
cccggcctgt acgcctgtgg ggaggccgcc tgtgcctcgg tacatggtgc caaccgcctc    1380
ggggcaaact cgctcttgga cctggttgtc tttggtcggg catgtgccct gagcatcgaa    1440
gagtcatgca ggcctggaga taaagtccct ccaattaaac caaacgctgg ggaagaatct    1500
gtcatgaatc ttgacaaatt gagatttgct gatggaagca taagaacatc ggaactgcga    1560
ctcagcatgc agaagtcaat gcaaaatcat gctgccgtgt tccgtgtggg aagcgtgttg    1620
caagaaggtt gtgggaaaat cagcaagctc tatgagacc taaagcacct gaagacgttc    1680
gaccggggaa tggtctggaa cacagacctg gtggagaccc tggagctgca gaacctgatg    1740
ctgtgtgcgc tgcagaccat ctacggagca gaggcgcgga aggagtcacg gggcgcgcat    1800
gccagggaag actacaaggt gcggattgat gagtacgatt actccaagcc catccagggg    1860
caacagaaga agccctttga ggagcactgg aggaagcaca ccctgtcctt tgtggacgtt    1920
ggcactggga aggtcactct ggaatataga cccgtaatcg acaaaacttt gaacgaggct    1980
gactgtgcca ccatcccgcc agccattcgc tcctactgat gagacaagat gtggtgatga    2040
cagaatcagc ttttgtaatt atgtataata gctcatgcat gtgtccatgt cataactgtc    2100
ttcatacgct tctgcactct ggggaagaag gagtacattg aagggagatt ggcacctagt    2160
ggctgggagc ttgccaggaa cccagtggcc agggagcgtg gcacttacct ttgtcccttg    2220
cttcattctt gtgagatgat aaaactgggc acagctctta ataaaatat aaatgag      2277
```

BRAIN NATRIURETIC PEPTIDE SPLICED VARIANT

CROSS-REFERENCE TO RELATED APPLICATION(S)

This application is related to Novel Brain Natriuretic Peptide Variants and Methods of use thereof, and claims priority to the below U.S. provisional applications which are incorporated by reference herein:

Application No. 60/539,127 filed Jan. 27, 2004—Novel Polynucleotides Encoding Polypeptides and Methods using same Application No. 60/587,851 filed Jul. 15, 2004—Novel Polynucleotides Encoding Polypeptides and Methods using same Application No. 60/607,246 filed Sep. 7, 2004—Novel Polynucleotides Encoding Polypeptides and Methods using same Application No. 60/622,016 filed Oct. 27, 2004—Variants of BNP, Use as Diagnostic Markers, and Assays and Methods of Use

FIELD OF THE INVENTION

The present invention is related to novel nucleotide and protein sequences that are variants of BNP, and assays and methods of use thereof.

BACKGROUND OF THE INVENTION

Degradation and remodeling of the ECM are essential processes for normal repair after tissue trauma. The physiological response to tissue trauma is a complex process involving multiple factors including cell migration and replication, turnover of extracellular matrix (ECM) components and changes to the cellular microenvironment. Essentially, such a response involves the repair or replacement of damaged tissues. The precise nature of such repair or replacement depends upon the tissues involved, although all such processes involve certain basic principles. The normal and necessary repair of any tissue after any trauma requires the coordination of a wide array of factors by regulated gene expression.

Fibrosis is therefore typically a reaction to tissue trauma. A number of different factors are believed to affect or modulate the biological pathways or mechanisms leading to tissue fibrosis. Such factors may include early inflammatory actions, a local increase in fibroblast cell populations, modulation of the synthetic function of fibroblasts, and altered regulation of the biosynthesis and degradation of collagen.

The pathophysiological response to the tissue trauma seen in fibrosis results in the formation of abnormal tissues which do not duplicate the functionality of the original organ tissue, so that the repair of tissue trauma does not lead to a complete restoration of organ capacity and function. One example of a fibrotic process which results from pathophysiological responses to tissue trauma is cardiac fibrosis. Cardiac fibrosis has a number of causes, which lead to the deposition of fibrotic tissue. For example, cardiac fibrosis may result from heart failure, hypertension and other cardiac pathological/disease states. As the deposition of such fibrotic tissue increases, the ability of the heart to function decreases, leading to disability and eventually death of the patient. The formation of fibrotic tissue in the heart is characterized by the deposition of abnormally large amounts of extracellular matrix components, including collagen, as well as other matrix proteins. Therefore, the cardiac fibrotic process needs to be inhibited in order to prevent damage to the cardiac tissue and hence to the ability of the heart to function.

Cardiac fibroblasts are important to the cardiac fibrotic process because they produce interstitial proteins and other myocardial components which have been implicated in heart failure (Hess et al, Circ., 63:360-371 (1981); Villari et al, Am. J. Cardiol., 69:927-934 (1992); Villari et al, JACC, 22:1477-1484 (1993); Brilla et al, Circ. Res., 69:107-115 (1991); and Sabbah et al, Mol. & Cell Biochem., 147:29-34 (1995)).

The pathology of heart failure is clearly associated with fibrosis for a number of cardiac pathological or disease states, including those associated with both volume and pressure overload (Maron et al, Am. J. Cardiol., 35:725-739 (1975); Schwarz et al, Am. J. Cardiol., 42:661-669 (1978); Fuster et al, Circ., 55:504-508 (1976); Bartosova et al, J. Physiol., 200:285-295 (1969); Weber et al, Circ., 83:1849-1865 (1991); Schaper et al, Basic Res. Cardiol., 87:S1303-S1309 (1992); Boluyt et al, Circ. Res., 75:23-32 (1994); and Bishop et al, J. Mol. Cell Cardiol., 22:1157-1165 (1990)). Cardiac surgery also may cause cardiac fibrosis; such fibrosis may also lead to the requirement for an additional operation, which is often associated with higher morbidity and mortality.

Detection and/or quantitation of cardiac fibrosis is therefore very important for preventing or treating such fibrosis. Various imaging techniques may be used to see the effects of cardiac fibrosis, but actually detecting such fibrosis at the molecular level currently requires an invasive procedure to obtain a tissue sample (biopsy), as there are no commercially available non-invasive tests for detection of cardiac fibrosis at the molecular level.

BNP (Brain Natriuretic Peptide) belongs to a family of natriuretic peptides produced by the heart. BNP and its related natriuretic peptide ANP contain a 17-amino acid ring structure and are produced by the cardiac atria in response to volume overload and by ventricles in response to pressure overload, respectively (Broomsma et al., 2001. Cardiovascular Research 51, 442-449.; McCullough et al., 2003. Reviews in cardiovascular medicine 4, suppl. 7, S3-S12). These hormones have powerful diuretic, natriuretic, vascular smooth muscle relaxing and vasodilation actions, thus lowering blood volume and blood pressure (Azzay et al., 2003. Heart Failure Review 8, 315-320.). With its impressive physiologic actions, BNP was an attractive target for development as a therapeutic agent for heart failure and/or as a diagnostic marker.

Both ANP and BNP are formed as pre-pro-polypeptides. Human BNP is derived from the 134-aa precursor preproBNP. Upon stimulation of release, a 26-aa signal peptide sequence is cleaved from the N-terminus of preproBNP. During release into circulation, the remaining proBNP1-108 prohormone is further cleaved by corin, a membrane-bound serine protease, into an N-terminal pro-BNP1-76 fragment and the active 32-peptide, C-terminal proBNP77-108 hormone termed BNP (Azzay et al., 2003. Heart Failure Review 8, 315-320.). The principal function of ANP and BNP is to protect the cardiovascular system from volume overload. They are secreted in response to the wall stretch, ventricular dilation and/or increased pressures resulting from fluid overload (Azzay et al., 2003. Heart Failure Review 8, 315-320.). Both cause intravascular volume contraction by inducing a shift of fluid from the capillary bed to the interstitium, resulting in a decrease in preload and blood pressure. BNP has the important ability to decrease left ventricular filling pressures without a resultant reflex tachycardia, reflex vasoconstriction, and further activation of vasoconstricting neurohumoral systems. BNP also has lusiotropic effects and has been demonstrated to inhibit cardiac fibrosis. The natriuretic peptides also appear to exhibit an antimitogenic effect in the heart and other organ systems, suggesting a potential role in the modulation of cell growth. Additional evidence suggests a direct vasodilatory effect on the coronary arteries with a reduction in myocardial oxygen consumption.

In addition to these cardiac and vascular properties, BNP has a direct effect on renal hemodynamics and function. Increased glomerular filtration is the result of an unbalanced vasodilatation of the afferent arterioles and vasoconstriction of the efferent arterioles. There also appears to be a direct tubular effect on sodium and water handling, resulting in natriuresis and diuresis as well as inhibition of aldosterone and rennin release. The net effect of these properties is balanced vasodilatation of the arterial and venous beds as well as natriuresis and diuresis (Fonarow G. C, 2003. Heart Failure Review 8, 321-325.).

Most effects of ANP and BNP are mediated through binding to the A-type natriuretic peptide receptor, which activates guanyl cyclase, leading to the formation of cyclic guanosine monophosphate (cGMP). CGMP has potent vasodilatory actions and acts as a second messenger for BNP. The A-type natriuretic peptide receptor is expressed in a variety of tissues, including kidney, blood vessels, adrenal glands, heart, lungs, adipose tissue, eye, pregnant uterus and placenta. Clearance of ANP and BNP from the blood is effected in two ways: through a special clearance receptor, the C-type natriuretic receptor, and through enzymatic degradation by neutral endopeptidases (Broomsma et al., 2001. Cardiovascular Research 51, 442-449). The natriuretic peptides are characterized by a 17 aa central ring structure, which is formed by a disulfide bridge and is suggested to be necessary for the binding of these peptides to their respective receptors and for their biological activity (Azzay et al., 2003. Heart Failure Review 8, 315-320.).

ANP and BNP are both expressed more in Atria than Ventrcles. BNP has a more favorable expression in ventricles (atria:ventricle expression ration 3:1 compared with 40:1 to ANP). In a situation of a failing heart both BNP and ANP expression is increased 100-fold above normal levels (Trends Endocrinol Metab. 2003 Nov;14(9):411-6). However, BNP rise is often larger and more rapid than ANP, and it emerged as a superior marker for heart failure and left-ventricular dysfunction (Azzay et al., 2003. Heart Failure Review 8, 315-320.). BNP was shown to have a diagnostic benefit for few different clinical purposes: 1. Elevated plasma levels of BNP are found in conditions of increased cardiac wall stress. In congestive heart failure (CHF), circulating concentrations of BNP are clearly elevated and this elevation reflects the severity of the condition. Therefore it can be used to establish prognosis in patients with heart failure. In addition, it provides a tool to monitor changes in the severity of failure without using more sophisticated diagnostic modalities like Echo imaging.

2. Several studies have clearly shown that natriuretic peptides are excellent prognostic indicators for survival in heart failure.

3. Detection of response to treatment: a continued increase in plasma concentration would be indicative of unsuccessful, and a decrease of successful, treatment. 4. In myocardial infarction ANP and BNP concentrations are also elevated, and are of prognostic value for indicating patients most at risk. 5. BNP measurements help to differentiate between cardiac versus non-cardiac causes of dyspnea (Lancet. 1994 Feb. 19;343(8895):440-4). However there is limited evidence that it can be a useful marker for the very early detection of cardiac damage or heart failure when patients are still asymptomatic.

The N-terminal proBNP (ntBNP) is more stable and its serum levels rise more then BNP, therefore it is theoretically a better marker for BNP overproduction than BNP itself. Yet, its added value over BNP diagnostic wise is minor. When studying CHF population with left ventricular ejection fraction (LVEF)<40% BNP and ntBNP showed no difference in the diagnostic properties. For patients with LVEF<50% (less severe patients), ntBNP showed slight improvement over BNP—receiver operating characteristics area under curve of 0.82 for ntBNP and 0.794 for BNP (Eur J Heart Fail. 2004 Mar. 15;6(3):295-300).

SUMMARY OF THE INVENTION

The background art does not teach or suggest variants of BNP. The background art also does not teach or suggest variants of BNP that are useful as diagnostic markers. The background art also does not teach or suggest variants of BNP that are useful as diagnostic markers for cardiac diseases and/or pathology.

The present invention overcomes these deficiencies of the background art by providing BNP variants, which may optionally be used as diagnostic markers.

Preferably these BNP variants are useful as diagnostic markers for cardiac diseases and/or pathology, including but not limited to for heart failure and left verntricular disfunction. According to preferred embodiments of the present invention, cardiac disease and/or pathology and/or condition and/or disorder may comprise one or more of Myocardial infarct, acute coronary syndrome, angina pectoris (stable and unstable), cardiomyopathy, myocarditis, congestive heart failure or any type of heart failure, the detection of reinfarction, the detection of success of thrombolytic therapy after Myocardial infarct, Myocardial infarct after surgery, assessing the size of infarct in Myocardial infarct, the differential diagnosis of heart related conditions from lung related conditions (as pulmonary embolism), the differential diagnosis of Dyspnea, and cardiac valve related conditions.

As used herein the phrase "cardiac disease" includes any type of cardiac pathology and/or disorder and/or damage, including both chronic and acute damage, as well as progression from acute to chronic damage of the heart, and also propagation of one acute event to another acute event. An example of the latter may occur when an infarct is followed by another infarct in a relatively short period of time, such as within 24 hours for example. An infarct may also lead to acute heart failure immediately after the infarct, as another example. These non-limiting examples are intended to demonstrate that cardiac disease may also comprise a plurality of acute events.

These variant markers may be described as "BNP variant disease markers". According to one embodiment of the present invention markers are specifically released to the bloodstream under disease conditions according to one of the above differential variant marker conditions. Optionally and preferably, the variant marker is detected in a biological sample which may optionally be taken from a subject (patient). According to preferred embodiments of the present invention, examples of suitable biological samples include but are not limited to blood, serum, plasma, blood cells, urine, sputum, saliva, stool, spinal fluid, lymph fluid, the external secretions of the skin, respiratory, intestinal, and genitourinary tracts, tears, milk, neuronal tissue, and any human organ or tissue. In a preferred embodiment, the biological sample comprises cardiac tissue and/or a serum sample and/or a urine sample and/or any other tissue or liquid sample. The sample can optionally be diluted with a suitable eluant before contacting the sample to the antibody, if an antibody is used.

Localization was determined according to four different software programs: tmhmm (from Center for Biological Sequence Analysis, Technical University of Denmark DTU, dotcbsdotdtudotdk/services/TMHMM/TMHMM2.0b.guide.php) or tmpred (from EMBnet, maintained by the ISREC Bionformatics group and the LICR Information Technology Office, Ludwig Institute for Cancer Research, Swiss Institute of Bioinformatics, dotchdot embnetdot org/software/TMPRED_form dothtml) for transmembrane region prediction; signalp_hmm and signalp_nn (both from Center for Biological Sequence Analysis, Technical University of Denmark DTU, dot cbsdotdtudot dk/services/SignalP/background/predictiondotphp) for signal peptide prediction. The terms "signalp_hmm and signalp_nn" refer to two modes of operation for the program SignalP: hmm refers to Hidden Markov Model, while nn refers to neural networks. Localization was also determined through manual inspection of known protein localization and/or gene structure, and the use of heuristics by the individual inventor. In some cases for the manual inspection of cellular localization prediction inventors used the ProLoc computational platform [Einat Hazkani-Covo, Erez Levanon, Galit Rotman, Dan Graur and Amit Novik; (2004) Evolution of multicellularity in metazoa: comparative analysis of the subcellular localization of proteins in Saccharomyces, Drosophila and Caenorhabditis. Cell Biology International 2004;28(3): 171-8.], which predicts protein localization based on various parameters including, protein domains (e.g., prediction of trans-membranous regions and localization thereof within the protein), pI, protein length, amino acid composition, homology to pre-annotated proteins, recognition of sequence patterns which direct the protein to a certain organelle (such as, nuclear localization signal, NLS, mitochondria localization signal), signal peptide and anchor modeling and using unique domains from Pfam that are specific to a single compartment.

Information is given in the text with regard to SNPs (single nucleotide polymorphisms). A description of the abbreviations is as follows. "T->C" means that the SNP results in a change at the position given in the table from T to C. Similarly, "M->Q" means that the SNP has caused a change in the corresponding amino acid sequence, from methionine (M) to glutamine (Q). If, in place of a letter at the right hand side for the nucleotide sequence SNP, there is a space, it indicates that a frameshift has occurred. A frameshift may also be indicated with a hyphen (-). A stop codon is indicated with an asterisk at the right hand side (*). As part of the description of an SNP, a comment may be found in parentheses after the above description of the SNP itself. This comment may include an FTId, which is an identifier to a SwissProt entry that was created with the indicated SNP. An FTId is a unique and stable feature identifier, which allows to construct links directly from position-specific annotation in the feature table to specialized protein-related databases. The FTId is always the last component of a feature in the description field, as follows: FTId=XXX_number, in which XXX is the 3-letter code for the specific feature key, separated by an underscore from a 6-digit number. In the table of the amino acid mutations of the wild type proteins of the selected splice variants of the invention, the header of the first column is "SNP position(s) on amino acid sequence", representing a position of a known mutation on amino acid sequence. SNPs may optionally be used as diagnostic markers according to the present invention, alone or in combination with one or more other SNPs and/or any other diagnostic marker. Preferred embodiments of the present invention comprise such SNPs, including but not limited to novel SNPs on the known (WT or wild type) protein sequences given below, as well as novel nucleic acid and/or amino acid sequences formed through such SNPs, and/or any SNP on a variant amino acid and/or nucleic acid sequence described herein.

The below list relates to abbreviations on the histogram showing EST expression of this cluster (tissues not shown had neglible or no expression).

ADP=adipocyte

BLD=blood

BLDR=bladder

BRN=brain

BONE=bone

BM=bone marrow

BRS=mammary gland

CAR=cartilage

CNS=central nervous system

COL=colon

E-ADR=endocrine_adrenal_gland

E-PAN=endocrine_pancreas

E-PT=endocrine_parathyroid_thyroid

ENDO=endocrine_unchar

EPID=epididymis

GI=gastrointestinal tract

GU=genitourinary

HN=head and neck

HRT=heart

KD=kidney

LI=liver

LUNG=lung

LN=lymph node

MUS=muscle

OV=ovary

PNS=peripheral nervous system

PRO=prostate

SKIN=skin

SPL=spleen

SYN=synovial membrane

TCELL=immune T cells

THYM=thymus

TST=testes

UTER=cervix-uterus

VAS=vascular

The Homology to the wild type was determined by Smith-Waterman version 5.1.2 Using Special (non default) parameters as follows:

model=sw.model
   GAPEXT=0
   GAPOP=100.0
   MATRIX=blosum100

It should be noted that the terms "segment", "seg" and "node" are used interchangeably in reference to nucleic acid sequences of the present invention; they refer to portions of nucleic acid sequences that were shown to have one or more properties as described below. They are also the building blocks that were used to construct complete nucleic acid sequences as described in greater detail below. Optionally and preferably, they are examples of oligonucleotides which are embodiments of the present invention, for example as amplicons, hybridization units and/or from which primers and/or complementary oligonucleotides may optionally be derived, and/or for any other use.

As used herein the phrase "cardiac disease" includes any type of cardiac pathology and/or disorder and/or damage, including both chronic and acute damage, as well as progression from acute to chronic damage of the heart, and also propagation of one acute event to another acute event. An example of the latter may occur when an infarct is followed by another infarct in a relatively short period of time, such as within 24 hours for example. An infarct may also lead to acute heart failure immediately after the infarct, as another example. These non-limiting examples are intended to demonstrate that cardiac disease may also comprise a plurality of acute events.

The term "marker" in the context of the present invention refers to a nucleic acid fragment, a peptide, or a polypeptide, which is differentially present in a sample taken from patients having a cardiac disease, such as acute cardiac damage for example, as compared to a comparable sample taken from subjects who do not have cardiac disease.

As used herein the phrase "differentially present" refers to differences in the quantity of a marker present in a sample taken from patients having cardiac disease as compared to a comparable sample taken from patients who do not have cardiac disease. For example, a nucleic acid fragment may optionally be differentially present between the two samples if the amount of the nucleic acid fragment in one sample is significantly different from the amount of the nucleic acid fragment in the other sample, for example as measured by hybridization and/or NAT-based assays. A polypeptide is differentially present between the two samples if the amount of the polypeptide in one sample is significantly different from the amount of the polypeptide in the other sample. It should be noted that if the marker is detectable in one sample and not detectable in the other, then such a marker can be considered to be differentially present. For example, in the case of acute cardiac damage, it is possible that a marker (such as a protein or fragment thereof) could optionally be present in a blood sample from the patient, indicating the presence of damage; lack of presence of such a marker (and/or presence at a low level) would therefore optionally and preferably indicate a lack of such damage. Alternatively, chronically damaged heart might cause a low level of the marker to be present in the blood sample, while acute damage would cause a high level to be present. One of ordinary skill in the art could easily determine such relative levels of the markers; further guidance is provided in the description of each individual marker below.

As used herein the phrase "diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein the phrase "diagnosing" refers to classifying a disease or a symptom, determining a severity of the disease, monitoring disease progression, forecasting an outcome of a disease and/or prospects of recovery. The term "detecting" may also optionally encompass any of the above.

Diagnosis of a disease according to the present invention can be effected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject, as described in greater detail below.

As used herein, the term "level" refers to expression levels of RNA and/or protein or to DNA copy number of a marker of the present invention.

Typically the level of the marker in a biological sample obtained from the subject is different (i.e., increased or decreased) from the level of the same variant in a similar sample obtained from a healthy individual (examples of biological samples are described herein).

Numerous well known tissue or fluid collection methods can be utilized to collect the biological sample from the subject in order to determine the level of DNA, RNA and/or polypeptide of the variant of interest in the subject.

Examples include, but are not limited to, fine needle biopsy, needle biopsy, core needle biopsy and surgical biopsy (e.g., brain biopsy), and lavage. Regardless of the procedure employed, once a biopsy/sample is obtained the level of the variant can be determined and a diagnosis can thus be made.

Determining the level of the same variant in normal tissues of the same origin is preferably effected along-side to detect an elevated expression and/or amplification and/or a decreased expression, of the variant as opposed to the normal tissues.

A "test amount" of a marker refers to an amount of a marker present in a sample being tested. A test amount can be either in absolute amount (e.g., microgram/ml) or a relative amount (e.g., relative intensity of signals).

A "test amount" of a marker refers to an amount of a marker in a subject's sample that is consistent with a diagnosis of cardiac disease. A test amount can be either in absolute amount (e.g., microgram/ml) or a relative amount (e.g., relative intensity of signals).

A "control amount" of a marker can be any amount or a range of amounts to be compared against a test amount of a marker. For example, a control amount of a marker can be the amount of a marker in a patient with cardiac disease or a person without cardiac disease. A control amount can be either in absolute amount (e.g., microgram/ml) or a relative amount (e.g., relative intensity of signals).

"Detect" refers to identifying the presence, absence or amount of the object to be detected.

A "label" includes any moiety or item detectable by spectroscopic, photo chemical, biochemical, immunochemical, or chemical means. For example, useful labels include 32P, 35S, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The label often generates a measurable signal, such as a radioactive, chromogenic, or fluorescent signal, that can be used to quantify the amount of bound label in a sample. The label can be incorporated in or attached to a primer or probe either covalently, or through ionic, van der Waals or hydrogen bonds, e.g., incorporation of radioactive nucleotides, or biotinylated nucleotides that are recognized by streptavadin. The label may be directly or indirectly detectable. Indirect detection can involve the binding of a second label to the first label, directly or indirectly. For example, the label can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules (see, e.g., P. D. Fahrlander and A. Klausner, Bio/Technology 6:1165 (1988)). Quantitation of the signal is achieved by, e.g., scintillation counting, densitometry, or flow cytometry.

Exemplary detectable labels, optionally and preferably for use with immunoassays, include but are not limited to magnetic beads, fluorescent dyes, radiolabels, enzymes (e.g., horse radish peroxidase, alkaline phosphatase and others commonly used in an ELISA), and calorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

"Immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide (or other epitope), refers to a binding reaction that is determinative of the presence of the protein in a heterogeneous population of proteins and other biologics. Thus, under designated immunoassay conditions, the specified antibodies bind to a particular protein at least two times greater than the background (non-specific signal) and do not substantially bind in a significant amount to other proteins present in the sample. Specific binding to an antibody under such conditions may require an antibody that is selected for its specificity for a particular protein. For example, polyclonal antibodies raised to seminal basic protein from specific species such as rat, mouse, or human can be selected to obtain only those polyclonal antibodies that are specifically immunoreactive with seminal basic protein and not with other proteins, except for polymorphic variants and alleles of seminal basic protein. This selection may be achieved by subtracting out antibodies that cross-react with seminal basic protein molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

According to preferred embodiments of the present invention, preferably any of the above nucleic acid and/or amino acid sequences further comprises any sequence having at least about 70%, preferably at least about 80%, more preferably at least about 90%, most preferably at least about 95% homology thereto.

All nucleic acid sequences and/or amino acid sequences shown herein as embodiments of the present invention relate to their isolated form, as isolated polynucleotides (including for all transcripts), oligonucleotides (including for all segments, amplicons and primers), peptides (including for all tails, bridges, insertions or heads, optionally including other antibody epitopes as described herein) and/or polypeptides (including for all proteins). It should be noted that oligonucleotide and polynucleotide, or peptide and polypeptide, may optionally be used interchangeably.

Unless otherwise noted, all experimental data relates to variants of the present invention, named according to the segment being tested (as expression was tested through RT-PCR as described).

According to preferred embodiments of the present invention, there is provided an isolated polynucleotide comprising a nucleic acid sequence selected from the group consisting of: HUMNATPEP_PEA_1_T1 (SEQ ID NO: 1), HUMNATPEP_PEA_1_T2 (SEQ ID NO: 2), HUMNATPEP_PEA_1_T3 (SEQ ID NO: 3) or HUMNATPEP_PEA_1_T4 (SEQ ID NO: 4).

According to preferred embodiments of the present invention, there is provided an isolated polynucleotide segment comprising a nucleic acid sequence selected from the group consisting of: HUMNATPEP_PEA_1_node_0 (SEQ ID NO: 5), HUMNATPEP_PEA_1_node_1 (SEQ ID NO: 6), HUMNATPEP_PEA_1_node_2 (SEQ ID NO: 7), HUMNATPEP_PEA_1_node_3 (SEQ ID NO: 8), HUMNATPEP_PEA_1_node_4 (SEQ ID NO: 9), HUMNATPEP_PEA_1_node_5 (SEQ ID NO: 10), or HUMNATPEP_PEA_1_node_6 (SEQ ID NO: 11).

According to preferred embodiments of the present invention, there is provided an isolated polypeptide comprising an amino acid sequence selected from the group consisting of: HUMNATPEP_PEA_1_P2 (SEQ ID NO: 13), HUMNATPEP_PEA_1_P3 (SEQ ID NO: 14) or HUMNATPEP_PEA_1_P7 (SEQ ID NO: 15).

According to preferred embodiments of the present invention, there is provided an isolated chimeric polypeptide encoding for HUMNATPEP_PEA_1_P2 (SEQ ID NO: 13), comprising a first amino acid sequence being at least 90% homologous to MDPQTAPSRALLLLLFLHLAFLGGRSHPLGSPGSASDLETS- GLQEQRNHLQGKLSELQVEQTSLEPLQE-
SPRPTGVWKSREVATEGIRGHRKMVLYTLRAPRSP
KMVQGSGCFGRKMDRISSSSGLGCK corresponding to amino acids 1-129 of ANFB_HUMAN, which also corresponds to amino acids 1-129 of HUMNATPEP_PEA__1_P2 (SEQ ID NO: 13), and a second amino acid sequence being at least 70%, optionally at least 80%, preferably at least 85%, more preferably at least 90% and most preferably at least 95% homologous to a polypeptide having the sequence GKHPLPPRPPSPIPVCDTVRVTLGFVVSGNIHTL corresponding to amino acids 130-162 of HUMNATPEP_PEA__1_P2 (SEQ ID NO: 13), wherein said first and second amino acid sequences are contiguous and in a sequential order.

According to preferred embodiments of the present invention, there is provided an isolated polypeptide encoding for a tail of HUMNATPEP_PEA__1_P2 (SEQ ID NO: 13), comprising a polypeptide being at least 70%, optionally at least about 80%, preferably at least about 85%, more preferably at least about 90% and most preferably at least about 95% homologous to the sequence GKHPLP-PRPPSPIPVCDTVRVTLGFVVSGN (SEQ ID NO: 42) TL in HUMNATPEP_PEA__1_P2 (SEQ ID NO: 13).

According to preferred embodiments of the present invention, there is provided an isolated chimeric polypeptide encoding for HUMNATPEP_PEA__1_P3 (SEQ ID NO: 14), comprising a first amino acid sequence being at least 90% homologous to MDPQTAPSRALLLLLFLHLAFLGGRSH-PLGSPGSASDLETSGLQ corresponding to amino acids 1-44 of ANFB_HUMAN, which also corresponds to amino acids 1-44 of HUMNATPEP_PEA__1_P3 (SEQ ID NO: 14), and a second amino acid sequence being at least 70%, optionally at least 80%, preferably at least 85%, more preferably at least 90% and most preferably at least 95% homologous to a polypeptide having the sequence VRAE-GSSGGLDSSNERVLTCCPKRPSSFLWN (SEQ ID NO: 43) corresponding to amino acids 45-75 of HUMNATPEP_PEA__1_P3 (SEQ ID NO: 14), wherein said first and second amino acid sequences are contiguous and in a sequential order.

According to preferred embodiments of the present invention, there is provided an isolated polypeptide encoding for a tail of HUMNATPEP_PEA__1_P3 (SEQ ID NO: 14), comprising a polypeptide being at least 70%, optionally at least about 80%, preferably at least about 85%, more preferably at least about 90% and most preferably at least about 95% homologous to the sequence VRAEGSSGGLDSS-NERVLTCCPKRPSSFLWN (SEQ ID NO: 43) in HUM-NATPEP_PEA__1_P3 (SEQ ID NO: 14).

According to preferred embodiments of the present invention, there is provided an isolated chimeric polypeptide encoding for HfUMNATPEP_PEA__1_P7 (SEQ ID NO: 15), comprising a first amino acid sequence being at least 90% homologous to MVLYTLRAPRSPKMVQGSGCF-GRKMDRISSSSGLGCKVLRRH corresponding to amino acids 93-134 of ANFB_HUMAN, which also corresponds to amino acids 1-42 of HUMNATPEP_PEA__1_P7 (SEQ ID NO: 15).

According to preferred embodiments of the present invention, there is provided an antibody capable of specifically binding to an epitope of an amino acid sequence as described herein.

Optionally amino acid sequence corresponds to a tail as described herein. Also optionally, the antibody is capable of differentiating between a splice variant having said epitope and a corresponding known protein.

According to preferred embodiments of the present invention, there is provided a kit for detecting heart disorders, comprising a kit detecting overexpression of a splice variant as described herein. Optionally, the kit comprises a NAT-based technology. Also optionally, the kit further comprises at least one primer pair capable of selectively hybridizing to a nucleic acid sequence as described herein.

Optionally, the kit further comprises at least one oligonucleotide capable of selectively hybridizing to a nucleic acid sequence as described herein. Also optionally, the kit comprises an antibody as described herein. Preferably, the kit further comprises at least one reagent for performing an ELISA or a Western blot.

According to preferred embodiments of the present invention, there is provided a method for detecting heart disorders, comprising detecting overexpression of a splice variant according to any of the above claims. Optionally, detecting overexpression is performed with a NAT-based technology. Also optionally, detecting overexpression is performed with an immunoassay. Preferably, the immunoassay comprises an antibody as described herein.

According to preferred embodiments of the present invention, there is provided a biomarker capable of detecting a BNP variant-detectable disease, comprising any of the above nucleic acid sequences or a fragment thereof, or any of the above amino acid sequences or a fragment thereof.

According to preferred embodiments of the present invention, there is provided a method for screening for variant-detectable disease, comprising detecting cells affected by a BNP variant-detectable disease with a biomarker or an antibody or a method or assay as described herein.

According to preferred embodiments of the present invention, there is provided a method for diagnosing a BNP variant detectable disease, comprising detecting cells affected by a BNP variant-detectable disease with a biomarker or an antibody or a method or assay as described herein.

According to preferred embodiments of the present invention, there is provided a method for monitoring disease progression and/or treatment efficacy and/or detection of acute over chronic exacerbation of a BNP variant-detectable disease, comprising detecting cells affected by a BNP variant-detectable disease with a biomarker or an antibody or a method or assay as described herein.

According to preferred embodiments of the present invention, there is provided a method of selecting a therapy for a BNP variant-detectable disease, comprising detecting cells affected by a BNP variant-detectable disease with a biomarker or an antibody or a method or assay as described herein and selecting a therapy according to said detection.

Optionally, the BNP variant-detectable disease comprises heart failure and/or left ventricular disfunction.

According to preferred embodiments of the present invention, there is provided a nucleic acid construct comprising the isolated polynucleotide as described herein.

Optionally, the nucleic acid construct further comprises a promoter for regulating transcription of the isolated polynucleotide in sense or antisense orientation.

Optionally, the nucleic acid construct further comprises a positive and a negative selection marker for selecting for homologous recombination events.

According to preferred embodiments of the present invention, there is provided a host cell comprising the nucleic acid construct as described herein.

According to preferred embodiments of the present invention, there is provided an isolated polypeptide comprising an amino acid sequence at least 70% identical to a polypeptide as described herein, as determined using the LALIGN software of EMBnet Switzerland dotchdotembnetdotorg/ indexdothtml) using default parameters or an active portion thereof.

According to preferred embodiments of the present invention, there is provided an oligonucleotide specifically hybridizable with a nucleic acid sequence encoding a polypeptide as described herein.

According to preferred embodiments of the present invention, there is provided a pharmaceutical composition comprising a therapeutically effective amount of a polypeptide as described herein and a pharmaceutically acceptable carrier or diluent.

According to preferred embodiments of the present invention, there is provided a method of treating BNP-related disease in a subject, the method comprising upregulating in the subject expression of a polypeptide as described herein, thereby treating the BNP-related disease in a subject. Optionally, upregulating expression of said polypeptide is effected by:

(i) administering said polypeptide to the subject; and/or
(ii) administering an expressible polynucleotide encoding said polypeptide to the subject.

According to preferred embodiments of the present invention, there is provided an isolated oligonucleotide, comprising an amplicon selected from the group consisting of SEQ ID NOs: 20, 23 or 26.

According to preferred embodiments of the present invention, there is provided a primer pair, comprising a pair of isolated oligonucleotides capable of amplifying an amplicon or segment as described herein. Optionally, the primer pair comprises a pair of isolated oligonucleotides selected from the group consisting of: SEQ NOs 18 and 19; 21 and 22; 24 and 25; or 27 and 28.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). All of these are hereby incorporated by reference as if fully set forth herein. As used herein, the following terms have the meanings ascribed to them unless specified otherwise.

BRIEF DESCRIPTION OF THE DRAWINGS

This patent or application file contains at least one drawing executed in color. Copies of this patent or patent application with color drawing(s) will be provided by the U.S. Patent and Trademark Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 shows a schematic summary of quantitative real-time PCR analysis.

FIG. 2 shows expression of ESTs in each category, as "parts per million".

FIG. 3A shows a comparison of the genomic structure for the variant transcript HUMNATPEP_PEA_1_T1 (SEQ ID NO: 1) and the known or "WT" transcript. FIG. 3B shows a comparison of the structure of the variant protein HUMNATPEP_PEA_1_P2 (SEQ ID NO: 13) in comparison to the structure of the known or "WT" protein.

FIG. 4 shows the expression of ANFB_HUMAN Natriuretic peptide transcripts detectable by HUMNATPEP seg5 amplicon (SEQ ID NO:20) in heart tissue samples as opposed to other tissues.

FIG. 5 is a histogram showing specific expression of HUMNATPEP seg2 (SEQ ID NO:23) transcripts in heart tissue samples as opposed to other tissues.

FIG. 6 is a histogram showing relative expression of the above-indicated Homo sapiens natriuretic peptide precursor B (NPPB) known protein transcripts in heart tissue samples as opposed to other tissues.

Figure 7:
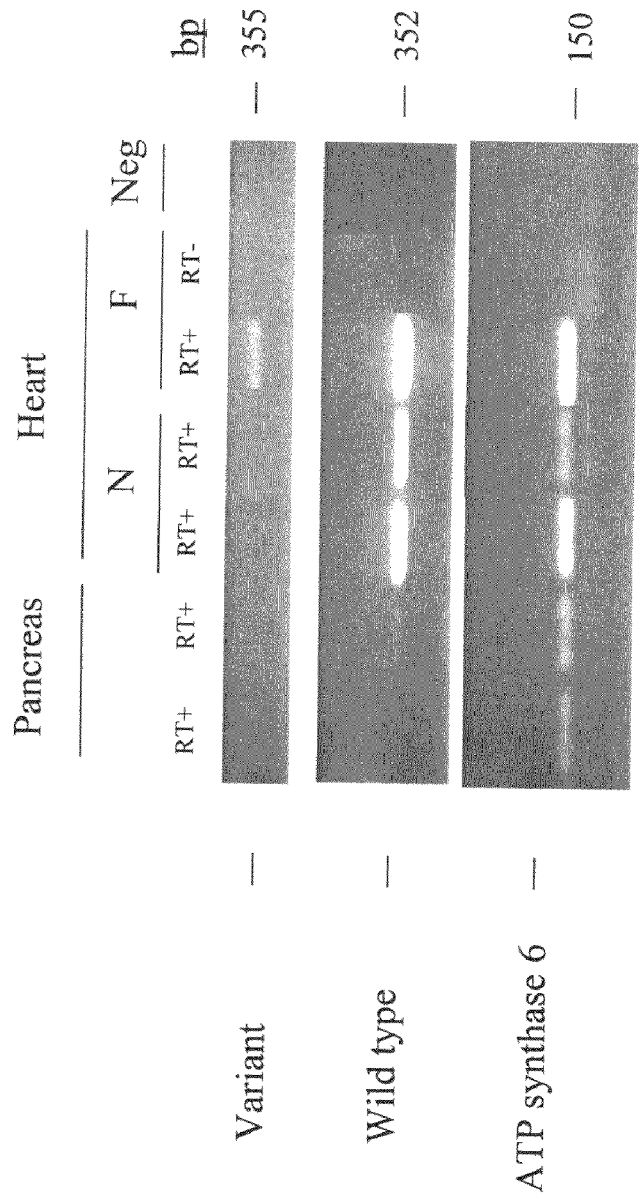

FIG. 7: presents RT_PCR results of known BNP transcript and the HUMNATPEP_PEA_1_T1 (SEQ ID NO: 1) splice variant, as described above. The expression of known BNP transcript was found to occur in normal heart tissue, while no expression of HUMNATPEP_PEA_1_T1 (SEQ ID NO: 1) variant was detected in this tissue panel. Specific expression of the HUMNATPEP_PEA_1_T1 (SEQ ID NO: 1) variant in focal fibrosis heart tissue was demonstrated. "N" means normal heart tissue; "F" means fibrotic heart tissue; "Neg" means negative control, without reverse transcriptase.

DESCRIPTION OF PREFERRED EMBODIMENTS

The present invention overcomes these deficiencies of the background art by providing BNP variants, which may optionally be used as diagnostic markers.

Preferably these BNP variants are useful as diagnostic markers for cardiac diseases and/or pathology, including but not limited to heart failure and left ventricular disfunction. The variants of the present invention may optionally be used, additionally or alternatively, for therapeutic uses, including but not limited to, diuretic, natriuretic, vascular smooth muscle relaxing and vasodilation actions, and lowering blood volume and blood pressure. These variants may optionally be used for therapeutic treatment of heart failure.

The present invention is of novel markers for cardiac disease that are both sensitive and accurate. Biomolecular sequences (amino acid and/or nucleic acid sequences) uncovered using the methodology of the present invention and described herein can be efficiently utilized as tissue or pathological markers and/or as drugs or drug targets for treating or preventing a disease.

These markers are specifically released to the bloodstream under conditions of cardiac disease and/or cardiac pathology, including but not limited to cardiac damage, and/or are otherwise expressed at a much higher level and/or specifically expressed in heart. The method of the present invention identifies clusters (genes) which are characterized in that the transcripts are differentially expressed in heart muscle tissue compared with other normal tissues, preferably in comparison to skeletal muscle tissue. In acute conditions under which heart muscle tissue experiences hypoxia (with or without necrosis), intracellular proteins that are not normally secreted can leak through the cell membrane to the extracellular space. Therefore, heart muscle tissue differentially expressed proteins, as through analysis of EST expression, are potential acute heart damage markers.

Leakage of intracellular content can also occur in chronic damage to the heart muscle, therefore proteins selected according to this method are potential markers for chronic heart conditions. When a protein that is differentially expressed in heart muscle is secreted, it is even more likely to be useful as a chronic heart damage marker, since secretion implies that the protein has a physiological role exterior to the cell, and therefore may be used by the heart muscle to respond to the chronic damage. This rationale is empirically supported by the non-limiting examples of the proteins BNP (brain natriuretic peptide) and ANF (atrial natriuretic factor), which are differentially expressed heart muscle proteins that are secreted and which were shown to be markers for congestive heart failure. In addition, BNP and ANF are not only differentially expressed in heart tissue, they are also overexpressed dramatically (hundreds of times greater expression) when heart failure occurs. Other heart specific secreted proteins might present similar overexpression in chronic damage.

Optionally and preferably, the markers described herein are overexpressed in heart as opposed to muscle, as described in greater detail below. The measurement of these markers, alone or in combination, in patient samples provides information that the diagnostician can correlate with a probable diagnosis of cardiac disease and/or cardiac pathology, including but not limited to cardiac damage.

The present invention therefore also relates to diagnostic assays for cardiac disease and/or cardiac pathology, including but not limited to cardiac damage, and methods of use of such markers for detection of cardiac disease and/or cardiac pathology, including but not limited to cardiac damage (alone or in combination), optionally and preferably in a sample taken from a subject (patient), which is more preferably some type of blood sample.

The present invention therefore also relates to diagnostic assays for cardiac disease and/or cardiac pathology, including but not limited to cardiac damage, and methods of use of such markers for detection of cardiac disease and/or cardiac pathology, including but not limited to cardiac damage (alone or in combination), optionally and preferably in a sample taken from a subject (patient), which is more preferably some type of blood sample.

In another embodiment, the present invention relates to bridges, tails, heads and/or insertions, and/or analogs, homologs and derivatives of such peptides. Such bridges, tails, heads and/or insertions are described in greater detail below with regard to the Examples.

As used herein a "tail" refers to a peptide sequence at the end of an amino acid sequence that is unique to a splice variant according to the present invention. Therefore, a splice variant having such a tail may optionally be considered as a chimera, in that at least a first portion of the splice variant is typically highly homologous (often 100% identical) to a portion of the corresponding known protein, while at least a second portion of the variant comprises the tail.

As used herein a "head" refers to a peptide sequence at the beginning of an amino acid sequence that is unique to a splice variant according to the present invention. Therefore, a splice variant having such a head may optionally be considered as a chimera, in that at least a first portion of the splice variant comprises the head, while at least a second portion is typically highly homologous (often 100% identical) to a portion of the corresponding known protein.

As used herein "an edge portion" refers to a connection between two portions of a splice variant according to the present invention that were not joined in the wild type or known protein. An edge may optionally arise due to a join between the above "known protein" portion of a variant and the tail, for example, and/or may occur if an internal portion of the wild type sequence is no longer present, such that two portions of the sequence are now contiguous in the splice variant that were not contiguous in the known protein. A "bridge" may optionally be an edge portion as described above, but may also include a join between a head and a "known protein" portion of a variant, or a join between a tail and a "known protein" portion of a variant, or a join between an insertion and a "known protein" portion of a variant.

Optionally and preferably, a bridge between a tail or a head or a unique insertion, and a "known protein" portion of a variant, comprises at least about 10 amino acids, more preferably at least about 20 amino acids, most preferably at least about 30 amino acids, and even more preferably at least about 40 amino acids, in which at least one amino acid is from the tail/head/insertion and at least one amino acid is from the "known protein" portion of a variant. Also optionally, the bridge may comprise any number of amino acids from about 10 to about 40 amino acids (for example, 10, 11, 12, 13 . . . 37, 38, 39, 40 amino acids in length, or any number in between).

It should be noted that a bridge cannot be extended beyond the length of the sequence in either direction, and it should be assumed that every bridge description is to be read in such manner that the bridge length does not extend beyond the sequence itself.

Furthermore, bridges are described with regard to a sliding window in certain contexts below. For example, certain descriptions of the bridges feature the following format: a bridge between two edges (in which a portion of the known protein is not present in the variant) may optionally be described as follows: a bridge portion of CONTIG-NAME_P1 (representing the name of the protein), comprising a polypeptide having a length "n", wherein n is at least about 10 amino acids in length, optionally at least about 20 amino acids in length, preferably at least about 30 amino acids in length, more preferably at least about 40 amino acids in length and most preferably at least about 50 amino acids in length, wherein at least two amino acids comprise XX (2 amino acids in the center of the bridge, one from each end of the edge), having a structure as follows (numbering according to the sequence of CONTIG-NAME_P1): a sequence starting from any of amino acid numbers 49−x to 49 (for example); and ending at any of amino acid numbers 50+((n−2)−x) (for example), in which x varies from 0 to n−2. In this example, it should also be read as including bridges in which n is any number of amino acids between 10-50 amino acids in length. Furthermore, the bridge polypeptide cannot extend beyond the sequence, so it should be read such that 49−x (for example) is not less than 1, nor 50+((n−2)−x) (for example) greater than the total sequence length.

In another embodiment, this invention provides antibodies specifically recognizing the splice variants and polypeptide fragments thereof of this invention. Preferably such antibodies differentially recognize splice variants of the present invention but do not recognize a corresponding known protein (such known proteins are discussed with regard to their splice variants in the Examples below).

In another embodiment, this invention provides an isolated nucleic acid molecule encoding for a splice variant according to the present invention, having a nucleotide sequence as set forth in any one of the sequences listed herein, or a sequence complementary thereto. In another embodiment, this invention provides an isolated nucleic acid molecule, having a nucleotide sequence as set forth in any one of the sequences listed herein, or a sequence complementary thereto. In another embodiment, this invention provides an oligonucleotide of at least about 12 nucleotides, specifically hybridizable with the nucleic acid molecules of this invention. In another embodiment, this invention provides vectors, cells, liposomes and compositions comprising the isolated nucleic acids of this invention.

In another embodiment, this invention provides a method for detecting a splice variant according to the present invention in a biological sample, comprising: contacting a biological sample with an antibody specifically recognizing a splice variant according to the present invention under conditions whereby the antibody specifically interacts with the splice variant in the biological sample but do not recognize known corresponding proteins (wherein the known protein is discussed with regard to its splice variant(s) in the Examples below), and detecting said interaction; wherein the presence of an interaction correlates with the presence of a splice variant in the biological sample.

In another embodiment, this invention provides a method for detecting a splice variant nucleic acid sequences in a biological sample, comprising: hybridizing the isolated nucleic acid molecules or oligonucleotide fragments of at least about a minimum length to a nucleic acid material of a biological sample and detecting a hybridization complex; wherein the presence of a hybridization complex correlates with the presence of a splice variant nucleic acid sequence in the biological sample.

According to the present invention, the splice variants described herein are non-limiting examples of markers for diagnosing cardiac disease and/or cardiac pathology, including but not limited to cardiac damage. Each splice variant marker of the present invention can be used alone or in combination, for various uses, including but not limited to, prognosis, prediction, screening, early diagnosis, determination of progression, therapy selection and treatment monitoring of cardiac disease and/or cardiac pathology, including but not limited to cardiac damage.

According to optional but preferred embodiments of the present invention, any marker according to the present invention may optionally be used alone or combination. Such a combination may optionally comprise a plurality of markers described herein, optionally including any subcombination of markers, and/or a combination featuring at least one other marker, for example a known marker. Furthermore, such a combination may optionally and preferably be used as described above with regard to determining a ratio between a quantitative or semi-quantitative measurement of any marker described herein to any other marker described herein, and/or any other known marker, and/or any other marker. With regard to such a ratio between any marker described herein (or a combination thereof) and a known marker, more preferably the known marker comprises the "known protein" as described in greater detail below with regard to each cluster or gene.

According to other preferred embodiments of the present invention, a splice variant protein or a fragment thereof, or a splice variant nucleic acid sequence or a fragment thereof, may be featured as a biomarker for detecting cardiac disease and/or cardiac pathology, including but not limited to cardiac damage, such that a biomarker may optionally comprise any of the above. According to still other preferred embodiments, the present invention optionally and preferably encompasses any amino acid sequence or fragment thereof encoded by a nucleic acid sequence corresponding to a splice variant protein as described herein. Any oligopeptide or peptide relating to such an amino acid sequence or fragment thereof may optionally also (additionally or alternatively) be used as a biomarker, including but not limited to the unique amino acid sequences of these proteins that are depicted as tails, heads, insertions, edges or bridges. The present invention also optionally encompasses antibodies capable of recognizing, and/or being elicited by, such oligopeptides or peptides.

The present invention also optionally and preferably encompasses any nucleic acid sequence or fragment thereof, or amino acid sequence or fragment thereof, corresponding to a splice variant of the present invention as described above, optionally for any application.

Non-limiting examples of methods or assays are described below.

The present invention also relates to kits based upon such diagnostic methods or assays.

Nucleic Acid Sequences and Oligonucleotides

Various embodiments of the present invention encompass nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or artificially induced, either randomly or in a targeted fashion.

The present invention encompasses nucleic acid sequences described herein; fragments thereof, sequences hybridizable therewith, sequences homologous thereto [e.g., at least 50%, at least 55%, at least 60%, at least 65%, at least 70%, at least 75%, at least 80%, at least 85%, at least 95% or more say 100% identical to the nucleic acid sequences set forth below], sequences encoding similar polypeptides with different codon usage, altered sequences characterized by mutations, such as deletion, insertion or substitution of one or more nucleotides, either naturally occurring or man induced, either randomly or in a targeted fashion. The present invention also encompasses homologous nucleic acid sequences (i.e., which form a part of a polynucleotide sequence of the present invention) which include sequence regions unique to the polynucleotides of the present invention.

In cases where the polynucleotide sequences of the present invention encode previously unidentified polypeptides, the present invention also encompasses novel polypeptides or portions thereof, which are encoded by the isolated polynucleotide and respective nucleic acid fragments thereof described hereinabove.

A "nucleic acid fragment" or an "oligonucleotide" or a "polynucleotide" are used herein interchangeably to refer to a polymer of nucleic acids. A polynucleotide sequence of the present invention refers to a single or double stranded nucleic acid sequences which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is composed of genomic and cDNA sequences. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

Preferred embodiments of the present invention encompass oligonucleotide probes.

An example of an oligonucleotide probe which can be utilized by the present invention is a single stranded polynucleotide which includes a sequence complementary to the unique sequence region of any variant according to the present invention, including but not limited to a nucleotide sequence coding for an amino sequence of a bridge, tail, head and/or insertion according to the present invention, and/or the equivalent portions of any nucleotide sequence given herein (including but not limited to a nucleotide sequence of a node, segment or amplicon described herein).

Alternatively, an oligonucleotide probe of the present invention can be designed to hybridize with a nucleic acid sequence encompassed by any of the above nucleic acid sequences, particularly the portions specified above, including but not limited to a nucleotide sequence coding for an amino sequence of a bridge, tail, head and/or insertion according to the present invention, and/or the equivalent portions of any nucleotide sequence given herein (including but not limited to a nucleotide sequence of a node, segment or amplicon described herein).

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

Oligonucleotides used according to this aspect of the present invention are those having a length selected from a range of about 10 to about 200 bases preferably about 15 to about 150 bases, more preferably about 20 to about 100 bases, most preferably about 20 to about 50 bases. Preferably, the oligonucleotide of the present invention features at least 17, at least 18, at least 19, at least 20, at least 22, at least 25, at least 30 or at least 40, bases specifically hybridizable with the biomarkers of the present invention.

The oligonucleotides of the present invention may comprise heterocylic nucleosides consisting of purines and the pyrimidines bases, bonded in a 3' to 5' phosphodiester linkage.

Preferably used oligonucleotides are those modified at one or more of the backbone, internucleoside linkages or bases, as is broadly described hereinunder.

Specific examples of preferred oligonucleotides useful according to this aspect of the present invention include oligonucleotides containing modified backbones or non-natural internucleoside linkages. Oligonucleotides having modified backbones include those that retain a phosphorus atom in the backbone, as disclosed in U.S. Pat. Nos: 4,469, 863; 4,476,301; 5,023,243; 5,177,196; 5,188,897; 5,264, 423; 5,276,019; 5,278,302; 5,286,717; 5,321,131; 5,399, 676; 5,405,939; 5,453,496; 5,455,233; 5,466,677; 5,476, 925; 5,519,126; 5,536,821; 5,541,306; 5,550,111; 5,563, 253; 5,571,799; 5,587,361; and 5,625,050.

Preferred modified oligonucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides which can be used according to the present invention, are those modified in both sugar and the internucleoside linkage, i.e., the backbone, of the nucleotide units are replaced with novel groups. The base units are maintained for complementation with the appropriate polynucleotide target. An example for such an oligonucleotide mimetic, includes peptide nucleic acid (PNA). United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present invention are disclosed in U.S. Pat. No: 6,303,374.

Oligonucleotides of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases particularly useful for increasing the binding affinity of the oligomeric compounds of the invention include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Another modification of the oligonucleotides of the invention involves chemically linking to the oligonucleotide one or more moieties or conjugates, which enhance the activity, cellular distribution or cellular uptake of the oligonucleotide. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety, as disclosed in U.S. Pat. No: 6,303,374.

It is not necessary for all positions in a given oligonucleotide molecule to be uniformly modified, and in fact more than one of the aforementioned modifications may be incorporated in a single compound or even at a single nucleoside within an oligonucleotide.

It will be appreciated that oligonucleotides of the present invention may include further modifications for more efficient use as diagnostic agents and/or to increase bioavailability, therapeutic efficacy and reduce cytotoxicity.

To enable cellular expression of the polynucleotides of the present invention, a nucleic acid construct according to the present invention may be used, which includes at least a coding region of one of the above nucleic acid sequences, and further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any suitable promoter sequence can be used by the nucleic acid construct of the present invention.

Preferably, the promoter utilized by the nucleic acid construct of the present invention is active in the specific cell population transformed. Examples of cell type-specific and/or tissue-specific promoters include promoters such as albumin that is liver specific, lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166). The nucleic acid construct of the present invention can further include an enhancer, which can be adjacent or distant to the promoter sequence and can function in up regulating the transcription therefrom.

The nucleic acid construct of the present invention preferably further includes an appropriate selectable marker and/or an origin of replication. Preferably, the nucleic acid construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (dot invitrogen dot com). Examples of retroviral vector and packaging systems are those sold by Clontech, San Diego, Calif., including Retro-X vectors pLNCX and pLXSN, which permit cloning into multiple cloning sites and the trasgene is transcribed from CMV promoter. Vectors derived from Mo-MuLV are also included such as pBabe, where the transgene will be transcribed from the 5' LTR promoter.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of the present invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Hybridization Assays

Detection of a nucleic acid of interest in a biological sample may optionally be effected by hybridization-based assays using an oligonucleotide probe (non-limiting examples of probes according to the present invention were previously described).

Traditional hybridization assays include PCR, RT-PCR, Real-time PCR, RNase protection, in-situ hybridization, primer extension, Southern blots (DNA detection), dot or slot blots (DNA, RNA), and Northern blots (RNA detection) (NAT type assays are described in greater detail below). More recently, PNAs have been described (Nielsen et al. 1999, Current Opin. Biotechnol. 10:71-75). Other detection methods include kits containing probes on a dipstick setup and the like.

Hybridization based assays which allow the detection of a variant of interest (i.e., DNA or RNA) in a biological sample rely on the use of oligonucleotides which can be 10, 15, 20, or 30 to 100 nucleotides long preferably from 10 to 50, more preferably from 40 to 50 nucleotides long.

Thus, the isolated polynucleotides (oligonucleotides) of the present invention are preferably hybridizable with any of the herein described nucleic acid sequences under moderate to stringent hybridization conditions.

Moderate to stringent hybridization conditions are characterized by a hybridization solution such as containing 10% dextrane sulfate, 1 M NaCl, 1% SDS and $5 \times 10^6$ cpm $^{32}$P labeled probe, at 65° C., with a final wash solution of 0.2×SSC and 0.1% SDS and final wash at 65° C. and whereas moderate hybridization is effected using a hybridization solution containing 10% dextrane sulfate, 1 M NaCl, 1% SDS and $5 \times 10^6$ cpm $^{32}$P labeled probe, at 65° C., with a final wash solution of 1×SSC and 0.1% SDS and final wash at 50° C.

More generally, hybridization of short nucleic acids (below 200 bp in length, e.g. 17-40 bp in length) can be effected using the following exemplary hybridization protocols which can be modified according to the desired stringency; (i) hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 1-1.5° C. below the $T_m$, final wash solution of 3 M TMACl, 0.01 M sodium phosphate (pH 6.8), 1 mM EDTA (pH 7.6), 0.5% SDS at 1-1.5° C. below the $T_m$; (ii) hybridization solution of 6×SSC and 0.1% SDS or 3 M TMACl, 0.01 M sodium phosphate (pH 6.8), 1 mM EDTA (pH 7.6), 0.5% SDS, 100 µml denatured salmon sperm DNA and 0.1% nonfat dried milk, hybridization temperature of 2-2.5° C. below the $T_m$, final wash solution of 3 M TMACl, 0.01 M sodium phosphate (pH 6.8), 1 mM EDTA (pH 7.6), 0.5% SDS at 1-1.5° C. below the $T_m$, final wash solution of 6×SSC, and final wash at 22° C.; (iii) hybridization solution of 6×SSC and 1% SDS or 3 M TMACl, 0.01 M sodium phosphate (pH 6.8), 1 mM EDTA (pH 7.6), 0.5% SDS, 100 µ/ml denatured salmon sperm DNA and 0.1% nonfat dried milk, hybridization temperature.

The detection of hybrid duplexes can be carried out by a number of methods. Typically, hybridization duplexes are separated from unhybridized nucleic acids and the labels bound to the duplexes are then detected. Such labels refer to radioactive, fluorescent, biological or enzymatic tags or labels of standard use in the art. A label can be conjugated to either the oligonucleotide probes or the nucleic acids derived from the biological sample.

Probes can be labeled according to numerous well known methods. Non-limiting examples of radioactive labels include 3H, 14C, 32P, and 35S. Non-limiting examples of detectable markers include ligands, fluorophores, chemiluminescent agents, enzymes, and antibodies. Other detectable markers for use with probes, which can enable an increase in sensitivity of the method of the invention, include biotin and radio-nucleotides. It will become evident to the person of ordinary skill that the choice of a particular label dictates the manner in which it is bound to the probe.

For example, oligonucleotides of the present invention can be labeled subsequent to synthesis, by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. Alternatively, when fluorescently-labeled oligonucleotide probes are used, fluorescein, lissamine, phycoerythrin, rhodamine (Perkin Elmer Cetus), Cy2, Cy3, Cy3.5, Cy5, Cy5.5, Cy7, FluorX (Amersham) and others [e.g., Kricka et al. (1992), Academic Press San Diego, Calif.] can be attached to the oligonucleotides.

Those skilled in the art will appreciate that wash steps may be employed to wash away excess target DNA or probe as well as unbound conjugate. Further, standard heterogeneous assay formats are suitable for detecting the hybrids using the labels present on the oligonucleotide primers and probes.

It will be appreciated that a variety of controls may be usefully employed to improve accuracy of hybridization assays. For instance, samples may be hybridized to an irrelevant probe and treated with RNAse A prior to hybridization, to assess false hybridization.

Although the present invention is not specifically dependent on the use of a label for the detection of a particular nucleic acid sequence, such a label might be beneficial, by increasing the sensitivity of the detection. Furthermore, it enables automation. Probes can be labeled according to numerous well known methods.

As commonly known, radioactive nucleotides can be incorporated into probes of the invention by several methods. Non-limiting examples of radioactive labels include $^3$H, $^{14}$C, $^{32}$P, and $^{35}$S.

Those skilled in the art will appreciate that wash steps may be employed to wash away excess target DNA or probe as well as unbound conjugate. Further, standard heterogeneous assay formats are suitable for detecting the hybrids using the labels present on the oligonucleotide primers and probes.

It will be appreciated that a variety of controls may be usefully employed to improve accuracy of hybridization assays.

Probes of the invention can be utilized with naturally occurring sugar-phosphate backbones as well as modified backbones including phosphorothioates, dithionates, alkyl phosphonates and a-nucleotides and the like. Probes of the invention can be constructed of either ribonucleic acid (RNA) or deoxyribonucleic acid (DNA), and preferably of DNA.

NAT Assays

Detection of a nucleic acid of interest in a biological sample may also optionally be effected by NAT-based assays, which involve nucleic acid amplification technology, such as PCR for example (or variations thereof such as real-time PCR for example).

As used herein, a "primer" defines an oligonucleotide which is capable of annealing to (hybridizing with) a target sequence, thereby creating a double stranded region which can serve as an initiation point for DNA synthesis under suitable conditions.

Amplification of a selected, or target, nucleic acid sequence may be carried out by a number of suitable methods. See generally Kwoh et al., 1990, Am. Biotechnol. Lab. 8:14 Numerous amplification techniques have been described and can be readily adapted to suit particular needs of a person of ordinary skill. Non-limiting examples of amplification techniques include polymerase chain reaction (PCR), ligase chain reaction (LCR), strand displacement amplification (SDA), transcription-based amplification, the q3 replicase system and NASBA (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 1989, supra).

The terminology "amplification pair" (or "primer pair") refers herein to a pair of oligonucleotides (oligos) of the present invention, which are selected to be used together in amplifying a selected nucleic acid sequence by one of a number of types of amplification processes, preferably a polymerase chain reaction. Other types of amplification processes include ligase chain reaction, strand displacement amplification, or nucleic acid sequence-based amplification, as explained in greater detail below. As commonly known in the art, the oligos are designed to bind to a complementary sequence under selected conditions.

In one particular embodiment, amplification of a nucleic acid sample from a patient is amplified under conditions which favor the amplification of the most abundant differentially expressed nucleic acid. In one preferred embodiment, RT-PCR is carried out on an mRNA sample from a patient under conditions which favor the amplification of the most abundant mRNA. In another preferred embodiment, the amplification of the differentially expressed nucleic acids is carried out simultaneously. It will be realized by a person skilled in the art that such methods could be adapted for the detection of differentially expressed proteins instead of differentially expressed nucleic acid sequences.

The nucleic acid (i.e. DNA or RNA) for practicing the present invention may be obtained according to well known methods.

Oligonucleotide primers of the present invention may be of any suitable length, depending on the particular assay format and the particular needs and targeted genomes employed. Optionally, the oligonucleotide primers are at least 12 nucleotides in length, preferably between 15 and 24 molecules, and they may be adapted to be especially suited to a chosen nucleic acid amplification system. As commonly known in the art, the oligonucleotide primers can be designed by taking into consideration the melting point of hybridization thereof with its targeted sequence (Sambrook et al., 1989, Molecular Cloning—A Laboratory Manual, 2nd Edition, CSH Laboratories; Ausubel et al., 1989, in Current Protocols in Molecular Biology, John Wiley & Sons Inc., N.Y.).

It will be appreciated that antisense oligonucleotides may be employed to quantify expression of a splice isoform of interest. Such detection is effected at the pre-mRNA level. Essentially the ability to quantitate transcription from a splice site of interest can be effected based on splice site accessibility. Oligonucleotides may compete with splicing factors for the splice site sequences. Thus, low activity of the antisense oligonucleotide is indicative of splicing activity.

The polymerase chain reaction and other nucleic acid amplification reactions are well known in the art (various non-limiting examples of these reactions are described in greater detail below). The pair of oligonucleotides according to this aspect of the present invention are preferably selected to have compatible melting temperatures (Tm), e.g., melting temperatures which differ by less than that 7° C., preferably less than 5° C., more preferably less than 4° C., most preferably less than 3° C., ideally between 3° C. and 0° C.

Polymerase Chain Reaction (PCR): The polymerase chain reaction (PCR), as described in U.S. Pat. Nos. 4,683,195 and 4,683,202 to Mullis and Mullis et al., is a method of increasing the concentration of a segment of target sequence in a mixture of genomic DNA without cloning or purification. This technology provides one approach to the problems of low target sequence concentration. PCR can be used to directly increase the concentration of the target to an easily detectable level. This process for amplifying the target sequence involves the introduction of a molar excess of two oligonucleotide primers which are complementary to their respective strands of the double-stranded target sequence to the DNA mixture containing the desired target sequence. The mixture is denatured and then allowed to hybridize. Following hybridization, the primers are extended with polymerase so as to form complementary strands. The steps of denaturation, hybridization (annealing), and polymerase extension (elongation) can be repeated as often as needed, in order to obtain relatively high concentrations of a segment of the desired target sequence.

The length of the segment of the desired target sequence is determined by the relative positions of the primers with respect to each other, and, therefore, this length is a controllable parameter. Because the desired segments of the target sequence become the dominant sequences (in terms of concentration) in the mixture, they are said to be "PCR-amplified."

Ligase Chain Reaction (LCR or LAR): The ligase chain reaction [LCR; sometimes referred to as "Ligase Amplification Reaction" (LAR)] has developed into a well-recognized alternative method of amplifying nucleic acids. In LCR, four oligonucleotides, two adjacent oligonucleotides which uniquely hybridize to one strand of target DNA, and a complementary set of adjacent oligonucleotides, which hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, and ligation amplify a short segment of DNA. LCR has also been used in combination with PCR to achieve enhanced detection of single-base changes: see for example Segev, PCT Publication No. W09001069 Al (1990). However, because the four oligonucleotides used in this assay can pair to form two short ligatable fragments, there is the potential for the generation of target-independent background signal. The use of LCR for mutant screening is limited to the examination of specific nucleic acid positions.

Self-Sustained Synthetic Reaction (3SR/NASBA): The self-sustained sequence replication reaction (3SR) is a transcription-based in vitro amplification system that can exponentially amplify RNA sequences at a uniform temperature. The amplified RNA can then be utilized for mutation detection. In this method, an oligonucleotide primer is used to add a phage RNA polymerase promoter to the 5' end of the sequence of interest. In a cocktail of enzymes and substrates that includes a second primer, reverse transcriptase, RNase H, RNA polymerase and ribo-and deoxyribonucleoside triphosphates, the target sequence undergoes repeated rounds of transcription, cDNA synthesis and second-strand synthesis to amplify the area of interest. The use of 3SR to detect mutations is kinetically limited to screening small segments of DNA (e.g., 200-300 base pairs).

Q-Beta (Qβ) Replicase: In this method, a probe which recognizes the sequence of interest is attached to the replicatable RNA template for Qβ replicase. A previously identified major problem with false positives resulting from the replication of unhybridized probes has been addressed through use of a sequence-specific ligation step. However, available thermnostable DNA ligases are not effective on this RNA substrate, so the ligation must be performed by T4 DNA ligase at low temperatures (37 degrees C.). This prevents the use of high temperature as a means of achieving specificity as in the LCR, the ligation event can be used to detect a mutation at the junction site, but not elsewhere.

A successful diagnostic method must be very specific. A straight-forward method of controlling the specificity of nucleic acid hybridization is by controlling the temperature of the reaction. While the 3SR/NASBA, and Qβ systems are all able to generate a large quantity of signal, one or more of the enzymes involved in each cannot be used at high temperature (i.e., >55 degrees C). Therefore the reaction temperatures cannot be raised to prevent non-specific hybridization of the probes. If probes are shortened in order to make them melt more easily at low temperatures, the likelihood of having more than one perfect match in a complex genome increases. For these reasons, PCR and LCR currently dominate the research field in detection technologies.

The basis of the amplification procedure in the PCR and LCR is the fact that the products of one cycle become usable templates in all subsequent cycles, consequently doubling the population with each cycle. The final yield of any such doubling system can be expressed as: $(1+X)^n = y$, where "X" is the mean efficiency (percent copied in each cycle), "n" is the number of cycles, and "y" is the overall efficiency, or yield of the reaction. If every copy of a target DNA is utilized as a template in every cycle of a polymerase chain reaction, then the mean efficiency is 100%. If 20 cycles of PCR are performed, then the yield will be $2^{20}$, or 1,048,576 copies of the starting material. If the reaction conditions reduce the mean efficiency to 85%, then the yield in those 20 cycles will be only $1.85^{20}$, or 220, 513 copies of the starting material. In other words, a PCR running at 85% efficiency will yield only 21% as much final product, compared to a reaction running at 100% efficiency. A reaction that is reduced to 50% mean efficiency will yield less than 1% of the possible product.

In practice, routine polymerase chain reactions rarely achieve the theoretical maximum yield, and PCRs are usually run for more than 20 cycles to compensate for the lower yield. At 50% mean efficiency, it would take 34 cycles to achieve the million-fold amplification theoretically possible in 20, and at lower efficiencies, the number of cycles required becomes prohibitive. In addition, any background products that amplify with a better mean efficiency than the intended target will become the dominant products.

Also, many variables can influence the mean efficiency of PCR, including target DNA length and secondary structure, primer length and design, primer and dNTP concentrations, and buffer composition, to name but a few. Contamination of the reaction with exogenous DNA (e.g., DNA spilled onto lab surfaces) or cross-contamination is also a major consideration. Reaction conditions must be carefully optimized for each different primer pair and target sequence, and the process can take days, even for an experienced investigator.

The laboriousness of this process, including numerous technical considerations and other factors, presents a significant drawback to using PCR in the clinical setting. Indeed, PCR has yet to penetrate the clinical market in a significant way. The same concerns arise with LCR, as LCR must also be optimized to use different oligonucleotide sequences for each target sequence. In addition, both methods require expensive equipment, capable of precise temperature cycling.

Many applications of nucleic acid detection technologies, such as in studies of allelic variation, involve not only detection of a specific sequence in a complex background, but also the discrimination between sequences with few, or single, nucleotide differences. One method of the detection of allele-specific variants by PCR is based upon the fact that it is difficult for Taq polymerase to synthesize a DNA strand when there is a mismatch between the template strand and the 3' end of the primer. An allele-specific variant may be detected by the use of a primer that is perfectly matched with only one of the possible alleles; the mismatch to the other allele acts to prevent the extension of the primer, thereby preventing the amplification of that sequence. This method has a substantial limitation in that the base composition of the mismatch influences the ability to prevent extension across the mismatch, and certain mismatches do not prevent extension or have only a minimal effect.

A similar 3'-mismatch strategy is used with greater effect to prevent ligation in the LCR. Any mismatch effectively blocks the action of the thermostable ligase, but LCR still has the drawback of target-independent background ligation products initiating the amplification. Moreover, the combination of PCR with subsequent LCR to identify the nucleotides at individual positions is also a clearly cumbersome proposition for the clinical laboratory.

The direct detection method according to various preferred embodiments of the present invention may be, for example a cycling probe reaction (CPR) or a branched DNA analysis.

When a sufficient amount of a nucleic acid to be detected is available, there are advantages to detecting that sequence directly, instead of making more copies of that target, (e.g., as in PCR and LCR). Most notably, a method that does not amplify the signal exponentially is more amenable to quantitative analysis. Even if the signal is enhanced by attaching multiple dyes to a single oligonucleotide, the correlation between the final signal intensity and amount of target is direct. Such a system has an additional advantage that the products of the reaction will not themselves promote further reaction, so contamination of lab surfaces by the products is not as much of a concern. Recently devised techniques have sought to eliminate the use of radioactivity and/or improve the sensitivity in automatable formats. Two examples are the "Cycling Probe Reaction" (CPR), and "Branched DNA" (bDNA).

Cycling probe reaction (CPR): The cycling probe reaction (CPR), uses a long chimeric oligonucleotide in which a central portion is made of RNA while the two termini are made of DNA. Hybridization of the probe to a target DNA and exposure to a thermostable RNase H causes the RNA portion to be digested. This destabilizes the remaining DNA portions of the duplex, releasing the remainder of the probe from the target DNA and allowing another probe molecule to repeat the process. The signal, in the form of cleaved probe molecules, accumulates at a linear rate. While the repeating process increases the signal, the RNA portion of the oligonucleotide is vulnerable to RNases that may carried through sample preparation.

Branched DNA: Branched DNA (bDNA), involves oligonucleotides with branched structures that allow each individual oligonucleotide to carry 35 to 40 labels (e.g., alkaline phosphatase enzymes). While this enhances the signal from a hybridization event, signal from non-specific binding is similarly increased.

The detection of at least one sequence change according to various preferred embodiments of the present invention may be accomplished by, for example restriction fragment length polymorphism (RFLP analysis), allele specific oligonucleotide (ASO) analysis, Denaturing/Temperature Gradient Gel Electrophoresis (DGGE/TGGE), Single-Strand Conformation Polymorphism (SSCP) analysis or Dideoxy fingerprinting (ddF).

The demand for tests which allow the detection of specific nucleic acid sequences and sequence changes is growing rapidly in clinical diagnostics. As nucleic acid sequence data for genes from humans and pathogenic organisms accumulates, the demand for fast, cost-effective, and easy-to-use tests for as yet mutations within specific sequences is rapidly increasing.

A handful of methods have been devised to scan nucleic acid segments for mutations. One option is to determine the entire gene sequence of each test sample (e.g., a bacterial isolate). For sequences under approximately 600 nucleotides, this may be accomplished using amplified material (e.g., PCR reaction products). This avoids the time and expense associated with cloning the segment of interest. However, specialized equipment and highly trained personnel are required, and the method is too labor-intense and expensive to be practical and effective in the clinical setting.

In view of the difficulties associated with sequencing, a given segment of nucleic acid may be characterized on several other levels. At the lowest resolution, the size of the molecule can be determined by electrophoresis by comparison to a known standard run on the same gel. A more detailed picture of the molecule may be achieved by cleavage with combinations of restriction enzymes prior to electrophoresis, to allow construction of an ordered map. The presence of specific sequences within the fragment can be detected by hybridization of a labeled probe, or the precise nucleotide sequence can be determined by partial chemical degradation or by primer extension in the presence of chain-terminating nucleotide analogs.

Restrictionfragment length polymorphism (RFLP): For detection of single-base differences between like sequences, the requirements of the analysis are often at the highest level of resolution. For cases in which the position of the nucleotide in question is known in advance, several methods have been developed for examining single base changes without direct sequencing. For example, if a mutation of interest happens to fall within a restriction recognition sequence, a change in the pattern of digestion can be used as a diagnostic tool (e.g., restriction fragment length polymorphism [RFLP] analysis).

Single point mutations have been also detected by the creation or destruction of RFLPs. Mutations are detected and localized by the presence and size of the RNA fragments generated by cleavage at the mismatches. Single nucleotide mismatches in DNA heteroduplexes are also recognized and cleaved by some chemicals, providing an alternative strategy to detect single base substitutions, generically named the "Mismatch Chemical Cleavage" (MCC). However, this method requires the use of osmium tetroxide and piperidine, two highly noxious chemicals which are not suited for use in a clinical laboratory.

RFLP analysis suffers from low sensitivity and requires a large amount of sample. When RFLP analysis is used for the detection of point mutations, it is, by its nature, limited to the detection of only those single base changes which fall within a restriction sequence of a known restriction endonuclease. Moreover, the majority of the available enzymes have 4 to 6 base-pair recognition sequences, and cleave too frequently for many large-scale DNA manipulations. Thus, it is applicable only in a small fraction of cases, as most mutations do not fall within such sites.

A handful of rare-cutting restriction enzymes with 8 base-pair specificities have been isolated and these are widely used in genetic mapping, but these enzymes are few in number, are limited to the recognition of G+C-rich sequences, and cleave at sites that tend to be highly clustered. Recently, endonucleases encoded by group I introns have been discovered that might have greater than 12 base-pair specificity, but again, these are few in number.

Allele specific oligonucleotide (ASO): If the change is not in a recognition sequence, then allele-specific oligonucleotides (ASOs), can be designed to hybridize in proximity to the mutated nucleotide, such that a primer extension or ligation event can bused as the indicator of a match or a mis-match. Hybridization with radioactively labeled allelic specific oligonucleotides (ASO) also has been applied to the detection of specific point mutations. The method is based on the differences in the melting temperature of short DNA fragments differing by a single nucleotide. Stringent hybridization and washing conditions can differentiate between mutant and wild-type alleles. The ASO approach applied to PCR products also has been extensively utilized by various researchers to detect and characterize point mutations in ras genes and gsp/gip oncogenes. Because of the presence of various nucleotide changes in multiple positions, the ASO method requires the use of many oligonucleotides to cover all possible oncogenic mutations.

With either of the techniques described above (i.e., RFLP and ASO), the precise location of the suspected mutation must be known in advance of the test. That is to say, they are inapplicable when one needs to detect the presence of a mutation within a gene or sequence of interest.

Denaturing/Temperature Gradient Gel Electrophoresis (DGGE/TGGE): Two other methods rely on detecting changes in electrophoretic mobility in response to minor sequence changes. One of these methods, termed "Denaturing Gradient Gel Electrophoresis" (DGGE) is based on the observation that slightly different sequences will display different patterns of local melting when electrophoretically resolved on a gradient gel. In this manner, variants can be distinguished, as differences in melting properties of homoduplexes versus heteroduplexes differing in a single nucleotide can detect the presence of mutations in the target sequences because of the corresponding changes in their electrophoretic mobilities. The fragments to be analyzed, usually PCR products, are "clamped" at one end by a long stretch of G-C base pairs (30-80) to allow complete denaturation of the sequence of interest without complete dissociation of the strands. The attachment of a GC "clamp" to the DNA fragments increases the fraction of mutations that can be recognized by DGGE. Attaching a GC clamp to one primer is critical to ensure that the amplified sequence has a low dissociation temperature. Modifications of the technique have been developed, using temperature gradients, and the method can be also applied to RNA:RNA duplexes.

Limitations on the utility of DGGE include the requirement that the denaturing conditions must be optimized for each type of DNA to be tested. Furthermore, the method requires specialized equipment to prepare the gels and maintain the needed high temperatures during electrophoresis. The expense associated with the synthesis of the clamping tail on one oligonucleotide for each sequence to be tested is also a major consideration. In addition, long running times are required for DGGE. The long running time of DGGE was shortened in a modification of DGGE called constant denaturant gel electrophoresis (CDGE). CDGE requires that gels be performed under different denaturant conditions in order to reach high efficiency for the detection of mutations.

A technique analogous to DGGE, termed temperature gradient gel electrophoresis (TGGE), uses a thermal gradient rather than a chemical denaturant gradient. TGGE requires the use of specialized equipment which can generate a temperature gradient perpendicularly oriented relative to the electrical field. TGGE can detect mutations in relatively small fragments of DNA therefore scanning of large gene segments requires the use of multiple PCR products prior to running the gel.

Single-Strand Conformation Polymorphism (SSCP): Another common method, called "Single-Strand Conformation Polymorphism" (SSCP) was developed by Hayashi, Sekya and colleagues and is based on the observation that single strands of nucleic acid can take on characteristic conformations in non-denaturing conditions, and these conformations influence electrophoretic mobility. The complementary strands assume sufficiently different structures that one strand may be resolved from the other. Changes in sequences within the fragment will also change the conformation, consequently altering the mobility and allowing this to be used as an assay for sequence variations.

The SSCP process involves denaturing a DNA segment (e.g., a PCR product) that is labeled on both strands, followed by slow electrophoretic separation on a nondenaturing polyacrylamide gel, so that intra-molecular interactions can form and not be disturbed during the run. This technique is extremely sensitive to variations in gel composition and temperature. A serious limitation of this method is the relative difficulty encountered in comparing data generated in different laboratories, under apparently similar conditions.

Dideoxy fingerprinting (ddF): The dideoxy fingerprinting (ddF) is another technique developed to scan genes for the presence of mutations. The ddF technique combines components of Sanger dideoxy sequencing with SSCP. A dideoxy sequencing reaction is performed using one dideoxy terminator and then the reaction products are electrophoresed on nondenaturing polyacrylamide gels to detect alterations in mobility of the termination segments as in SSCP analysis. While ddF is an improvement over SSCP in terms of increased sensitivity, ddF requires the use of expensive dideoxynucleotides and this technique is still limited to the analysis of fragments of the size suitable for SSCP (i.e., fragments of 200-300 bases for optimal detection of mutations).

In addition to the above limitations, all of these methods are limited as to the size of the nucleic acid fragment that can be analyzed. For the direct sequencing approach, sequences of greater than 600 base pairs require cloning, with the consequent delays and expense of either deletion sub-cloning or primer walking, in order to cover the entire fragment. SSCP and DGGE have even more severe size limitations. Because of reduced sensitivity to sequence changes, these methods are not considered suitable for larger fragments. Although SSCP is reportedly able to detect 90% of single-base substitutions within a 200 base-pair fragment, the detection drops to less than 50% for 400 base pair fragments. Similarly, the sensitivity of DGGE decreases as the length of the fragment reaches 500 base-pairs. The ddF technique, as a combination of direct sequencing and SSCP, is also limited by the relatively small size of the DNA that can be screened.

According to a presently preferred embodiment of the present invention the step of searching for any of the nucleic acid sequences described here, in tumor cells or in cells derived from a cancer patient is effected by any suitable technique, including, but not limited to, nucleic acid sequencing, polymerase chain reaction, ligase chain reaction, self-sustained synthetic reaction, Qβ-Replicase, cycling probe reaction, branched DNA, restriction fragment length polymorphism analysis, mismatch chemical cleavage, heteroduplex analysis, allele-specific oligonucleotides, denaturing gradient gel electrophoresis, constant denaturant gel electrophoresis, temperature gradient gel electrophoresis and dideoxy fingerprinting.

Detection may also optionally be performed with a chip or other such device. The nucleic acid sample which includes the candidate region to be analyzed is preferably isolated, amplified and labeled with a reporter group. This reporter group can be a fluorescent group such as phycoerythrin. The labeled nucleic acid is then incubated with the probes immobilized on the chip using a fluidics station. describe the fabrication of fluidics devices and particularly microcapillary devices, in silicon and glass substrates.

Once the reaction is completed, the chip is inserted into a scanner and patterns of hybridization are detected. The hybridization data is collected, as a signal emitted from the reporter groups already incorporated into the nucleic acid, which is now bound to the probes attached to the chip. Since the sequence and position of each probe immobilized on the chip is known, the identity of the nucleic acid hybridized to a given probe can be determined.

It will be appreciated that when utilized along with automated equipment, the above described detection methods can be used to screen multiple samples for a disease and/or pathological condition both rapidly and easily.

Amino Acid Sequences and Peptides

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

Polypeptide products can be biochemically synthesized such as by employing standard solid phase techniques. Such methods include but are not limited to exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry.

Solid phase polypeptide synthesis procedures are well known in the art and further described by John Morrow Stewart and Janis Dillaha Young, Solid Phase Peptide Syntheses (2nd Ed., Pierce Chemical Company, 1984).

Synthetic polypeptides can optionally be purified by preparative high performance liquid chromatography [Creighton T. (1983) Proteins, structures and molecular principles.

W H Freeman and Co. N.Y.], after which their composition can be confirmed via amino acid sequencing.

In cases where large amounts of a polypeptide are desired, it can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

The present invention also encompasses polypeptides encoded by the polynucleotide sequences of the present invention, as well as polypeptides according to the amino acid sequences described herein. The present invention also encompasses homologues of these polypeptides, such homologues can be at least 50%, at least 55%, at least 60%, at least 65%, at least 70%, at least 75%, at least 80%, at least 85%, at least 95% or more say 100% homologous to the amino acid sequences set forth below, as can be determined using BlastP software of the National Center of Biotechnology Information (NCBI) using default parameters, optionally and preferably including the following: filtering on (this option filters repetitive or low-complexity sequences from the query using the Seg (protein) program), scoring matrix is BLOSUM62 for proteins, word size is 3, E value is 10, gap costs are 11, 1 (initialization and extension), and number of alignments shown is 50. Optionally and preferably, nucleic acid sequence homology (identity) is determined using BlastN software of the National Center of Biotechnology Information (NCBI) using default parameters, which preferably include using the DUST filter program, and also preferably include having an E value of 10, filtering low complexity sequences and a word size of 11. Finally, the present invention also encompasses fragments of the above described polypeptides and polypeptides having mutations, such as deletions, insertions or substitutions of one or more amino acids, either naturally occurring or artificially induced, either randomly or in a targeted fashion.

It will be appreciated that peptides identified according the present invention may be degradation products, synthetic peptides or recombinant peptides as well as peptidomimetics, typically, synthetic peptides and peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2—NH, CH2—S, CH2—S═O, O═C—NH, CH2—O, CH2—CH2, S═C—NH, CH═CH or CF═CH, backbone modifications, and residue modification. Methods for preparing peptidomimetic compounds are well known in the art and are specified. Further details in this respect are provided hereinunder.

Peptide bonds (—CO—NH—) within the peptide may be substituted, for example, by N-methylated bonds (—N(CH3)—CO—), ester bonds (—C(R)H—C—O—O—C(R)—N—), ketomethylen bonds (—CO—CH2—), α-aza bonds (—NH—N(R)—CO—), wherein R is any alkyl, e.g., methyl, carba bonds (—CH2—NH—), hydroxyethylene bonds (—CH(OH)—CH2—), thioamide bonds (—CS—NH—), olefinic double bonds (—CH═CH—), retro amide bonds (—NH—CO—), peptide derivatives (—N(R)—CH2—CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Table 1 non-conventional or modified amino acids which can be used with the present invention.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-Carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl- | Norb | L-N-methylglutamine | Nmgln |
| Carboxylate |  | L-N-methylglutamic acid | Nmglu |
| Cyclohexylalanine | Chexa | L-N-methylhistidine | Nmhis |
| Cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |

TABLE 1-continued

| Non-conventional amino acid | Code | Non-conventional amino acid | Code |
|---|---|---|---|
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | Penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | Penicillamine | Pen |

TABLE 1-continued

| Non-conventional amino acid | Code | Non-conventional amino acid | Code |
|---|---|---|---|
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

Since the peptides of the present invention are preferably utilized in diagnostics which require the peptides to be in soluble form, the peptides of the present invention preferably include one or more non-natural or natural polar amino acids, including but not limited to serine and threonine which are capable of increasing peptide solubility due to their hydroxyl-containing side chain.

The peptides of the present invention are preferably utilized in a linear form, although it will be appreciated that in cases where cyclicization does not severely interfere with peptide characteristics, cyclic forms of the peptide can also be utilized.

The peptides of present invention can be biochemically synthesized such as by using standard solid phase techniques. These methods include exclusive solid phase synthesis well known in the art, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry.

Synthetic peptides can be purified by preparative high performance liquid chromatography and the composition of which can be confirmed via amino acid sequencing.

In cases where large amounts of the peptides of the present invention are desired, the peptides of the present invention can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463 and also as described above.

Antibodies

"Antibody" refers to a polypeptide ligand that is preferably substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad-immunoglobulin variable region genes. Antibodies exist, e.g., as intact immunoglobulins or as a number of well characterized fragments produced by digestion with various peptidases. This includes, e.g., Fab' and F(ab)$'_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, CH1, CH2 and CH3, but does not include the heavy chain variable region.

The functional fragments of antibodies, such as Fab, F(ab')2, and Fv that are capable of binding to macrophages, are described as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab'fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5 S fragment denoted F(ab')2. This fragment can be further cleaved using a thiol reducing agent, and optionally a blocking group for the sulfhydryl groups resulting from cleavage of disulfide linkages, to produce 3.5 S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab') or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10,: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Preferably, the antibody of this aspect of the present invention specifically binds at least one epitope of the polypeptide variants of the present invention. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

Optionally, a unique epitope may be created in a variant due to a change in one or more post-translational modifications, including but not limited to glycosylation and/or phosphorylation, as described below. Such a change may also cause a new epitope to be created, for example through removal of glycosylation at a particular site.

An epitope according to the present invention may also optionally comprise part or all of a unique sequence portion of a variant according to the present invention in combination with at least one other portion of the variant which is not contiguous to the unique sequence portion in the linear polypeptide itself, yet which are able to form an epitope in combination. One or more unique sequence portions may optionally combine with one or more other non-contiguous portions of the variant (including a portion which may have high homology to a portion of the known protein) to form an epitope.

Immunoassays

In another embodiment of the present invention, an immunoassay can be used to qualitatively or quantitatively detect and analyze markers in a sample. This method comprises: providing an antibody that specifically binds to a marker; contacting a sample with the antibody; and detecting the presence of a complex of the antibody bound to the marker in the sample.

To prepare an antibody that specifically binds to a marker, purified protein markers can be used. Antibodies that specifically bind to a protein marker can be prepared using any suitable methods known in the art.

After the antibody is provided, a marker can be detected and/or quantified using any of a number of well recognized immunological binding assays. Useful assays include, for example, an enzyme immune assay (EIA) such as enzyme-linked immunosorbent assay (ELISA), a radioimmune assay (RIA), a Western blot assay, or a slot blot assay see, e.g., U.S. Pat. Nos. 4,366,241; 4,376,110; 4,517,288; and 4,837,168). Generally, a sample obtained from a subject can be contacted with the antibody that specifically binds the marker.

Optionally, the antibody can be fixed to a solid support to facilitate washing and subsequent isolation of the complex, prior to contacting the antibody with a sample. Examples of solid supports include but are not limited to glass or plastic in the form of, e.g., a microtiter plate, a stick, a bead, or a microbead. Antibodies can also be attached to a solid support.

After incubating the sample with antibodies, the mixture is washed and the antibody-marker complex formed can be detected. This can be accomplished by incubating the washed mixture with a detection reagent. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations and the like.

Usually the assays will be carried out at ambient temperature, although they can be conducted over a range of temperatures, such as 10° C. to 40° C.

The immunoassay can be used to determine a test amount of a marker in a sample from a subject. First, a test amount of a marker in a sample can be detected using the immunoassay methods described above. If a marker is present in the sample, it will form an antibody-marker complex with an antibody that specifically binds the marker under suitable incubation conditions described above. The amount of an antibody-marker complex can optionally be determined by comparing to a standard. As noted above, the test amount of marker need not be measured in absolute units, as long as the unit of measurement can be compared to a control amount and/or signal.

Preferably used are antibodies which specifically interact with the polypeptides of the present invention and not with wild type proteins or other isoforms thereof, for example. Such antibodies are directed, for example, to the unique sequence portions of the polypeptide variants of the present invention, including but not limited to bridges, heads, tails and insertions described in greater detail below. Preferred embodiments of antibodies according to the present invention are described in greater detail with regard to the section entitled "Antibodies".

Radio-immunoassay (RIA): In one version, this method involves precipitation of the desired substrate and in the methods detailed hereinbelow, with a specific antibody and radiolabelled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Enzyme linked immunosorbent assay (ELISA): This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a calorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabelled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Immunohistochemical analysis: This method involves detection of a substrate in situ in fixed cells by substrate specific antibodies. The substrate specific antibodies may be enzyme linked or linked to fluorophores. Detection is by microscopy and subjective evaluation. If enzyme linked antibodies are employed, a calorimetric reaction may be required.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Radio-imaging Methods

These methods include but are not limited to, positron emission tomography (PET) single photon emission computed tomography (SPECT). Both of these techniques are non-invasive, and can be used to detect and/or measure a wide variety of tissue events and/or functions, such as detecting cancerous cells for example. Unlike PET, SPECT can optionally be used with two labels simultaneously. SPECT has some other advantages as well, for example with regard to cost and the types of labels that can be used. For example, U.S. Pat. No. 6,696,686 describes the use of SPECT for detection of breast cancer, and is hereby incorporated by reference as if fully set forth herein.

Display Libraries

According to still another aspect of the present invention there is provided a display library comprising a plurality of display vehicles (such as phages, viruses or bacteria) each displaying at least 6, at least 7, at least 8, at least 9, at least 10, 10-15, 12-17, 15-20, 15-30 or 20-50 consecutive amino acids derived from the polypeptide sequences of the present invention.

Methods of constructing such display libraries are well known in the art. Such methods are described in, for example, Young A C, et al., "The three-dimensional structures of a polysaccharide binding antibody to Cryptococcus neoformans and its complex with a peptide from a phage display library: implications for the identification of peptide mimotopes" J Mol Biol 1997 Dec. 12; 274(4):622-34; Giebel L B et al. "Screening of cyclic peptide phage libraries identifies ligands that bind streptavidin with high affinities" Biochemistry 1995 Nov. 28; 34(47):15430-5; Davies E L et al., "Selection of specific phage-display antibodies using libraries derived from chicken immunoglobulin genes" J Immunol Methods 1995 Oct. 12; 186(1):125-35; Jones C R T al. "Current trends in molecular recognition and bioseparation" J Chromatogr A 1995 Jul. 14; 707(1):3-22; Deng S J et al. "Basis for selection of improved carbohydrate-binding single-chain antibodies from synthetic gene libraries" Proc Natl Acad Sci USA 1995 May 23; 92(11):4992-6; and Deng S J et al. "Selection of antibody single-chain variable fragments with improved carbohydrate binding by phage display" J Biol Chem 1994 Apr. 1; 269(13):9533-8, which are incorporated herein by reference.

Treatment

As mentioned hereinabove the BNP variants of the present invention and compositions derived therefrom (i.e., peptides, oligonucleotides) can be used to treat a subject having, being diagnosed with or predisposed to a BNP-related disease, such as cardiac disease.

The subject according to the present invention is a mammal, preferably a human which is diagnosed with one of the diseases described hereinabove, or alternatively is predisposed to having one of the diseases described hereinabove.

As used herein the term "treating" refers to preventing, curing, reversing, attenuating, alleviating, minimizing, suppressing or halting the deleterious effects of the BNP-related disease.

Treating according to the present invention is effected by specifically upregulating the expression in the subject of at least one of the polypeptides of the present invention.

As used hereinabove the phrase "active portion" refers to an amino acid sequence portion which is capable of displaying one or more functions of the BNP polypeptides of the present invention.

Upregulating Methods and Agents

Upregulating expression of the BNP variants of the present invention may be effected via the administration of at least one of the exogenous polynucleotide sequences of the present invention (e.g., SEQ ID NOs: 1-3, 9-10 and/or 12-14) ligated into a nucleic acid expression construct designed for expression of coding sequences in eukaryotic cells (e.g., mammalian cells). Accordingly, the exogenous polynucleotide sequence may be a DNA or RNA sequence encoding the variants of the present invention or active portions thereof.

It will be appreciated that the nucleic acid construct can be administered to the individual employing any suitable mode of administration, described hereinbelow (i.e., in-vivo gene therapy). Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (ie., ex-vivo gene therapy).

To enable cellular expression of the polynucleotides of the present invention, the nucleic acid construct of the present invention further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any suitable promoter sequence can be used by the nucleic acid construct of the present invention.

Preferably, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166). The nucleic acid construct of the present invention can further include an enhancer, which can be adjacent or distant to the promoter sequence and can function in up regulating the transcription therefrom.

The nucleic acid construct of the present invention preferably further includes an appropriate selectable marker and/or an origin of replication. Preferably, the nucleic acid construct utilized is a shuttle vector, which can propagate both in *E. coli* (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (dot invitrogen dot com). Examples of retroviral vector and packaging systems are those sold by-Clontech, San Diego, Calif., including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5' LTR promoter.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of the present invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

It will be appreciated that the present methodology may also be effected by specifically upregulating the expression of the variants of the present invention endogenously in the subject. Agents for upregulating endogenous expression of specific splice variants of a given gene include antisense oligonucleotides, which are directed at splice sites of interest, thereby altering the splicing pattern of the gene. This approach has been successfully used for shifting the balance of expression of the two isoforms of Bcl-x [Taylor (1999) Nat. Biotechnol. 17:1097-1100; and Mercatante (2001) J. Biol. Chem. 276:16411-16417]; IL-5R [Karras (2000) Mol. Pharmacol. 58:380-387]; and c-myc [Giles (1999) Antisense Acid Drug Dev. 9:213-220].

For example, interleukin 5 and its receptor play a critical role as regulators of hematopoiesis and as mediators in some inflammatory diseases such as allergy and asthma. Two alternatively spliced isoforms are generated from the IL-5R gene, which include (i.e., long form) or exclude (i.e., short form) exon 9. The long form encodes for the intact membrane-bound receptor, while the shorter form encodes for a secreted soluble non-functional receptor. Using 2'-O-MOE-oligonucleotides specific to regions of exon 9, Karras and co-workers (supra) were able to significantly decrease the expression of the wild type receptor and increase the expression of the shorter isoforms. Design and synthesis of oligonucleotides which can be used according to the present invention are described hereinbelow and by Sazani and Kole (2003) Progress in Molecular and Subcellular Biology 31:217-239.

Alternatively or additionally, upregulation may be effected by administering to the subject at least one polypeptide agent of the polypeptides of the present invention or an active portion thereof, as described hereinabove. However, since the bioavailability of large polypeptides is relatively small due to high degradation rate and low penetration rate, administration of polypeptides is preferably confined to small peptide fragments (e.g., about 100 amino acids).

An agent capable of upregulating a BNP polypeptide may also be any compound which is capable of increasing the transcription and/or translation of an endogenous DNA or mRNA encoding the BNP polypeptide and thus increasing endogenous BNP activity.

An agent capable of upregulating a BNP may also be an exogenous polypeptide including at least a functional portion (as described hereinabove) of the BNP.

Upregulation of BNP can be also achieved by introducing at least one BNP substrate. Non-limiting examples of such agents include HOXC10 (Gabellini D, et al., 2003; EMBO J. 22: 3715-24), human securin and cyclin B1 (Tang Z, et al., 2001; Mol. Biol. Cell. 12: 3839-51 ), cyclins A, geminin H, and Cut2p (Bastians H, et al., 1999; Mol. Biol. Cell. 10: 3927-3941).

It will be appreciated that upregulation of BNP can be also effected by administration of BNP-expressing cells into the individual.

BNP-expressing cells can be any suitable cells, such as lung, ovary, bone marrow which are derived from the individual and are transfected ex vivo with an expression vector containing the polynucleotide designed to express BNP as described hereinabove.

Administration of the BNP-expressing cells of the present invention can be effected using any suitable route such as intravenous, intra peritoneal, and intra ovary. According to presently preferred embodiments, the BNP-expressing cells of the present invention are introduced to the individual using intravenous and/or intra organ administrations.

BNP-expressing cells of the present invention can be derived from either autologous sources such as self bone marrow cells or from allogeneic sources such as bone marrow or other cells derived from non-autologous sources. Since non-autologous cells are likely to induce an immune reaction when administered to the body several approaches have been developed to reduce the likelihood of rejection of non-autologous cells. These include either suppressing the recipient immune system or encapsulating the non-autologous cells or tissues in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu MZ, et al., Cell encapsulation with alginate and alpha-phenoxycinnamylidene-acetylated poly(allylamine). Biotechnol Bioeng. 2000, 70: 479-83, Chang TM and Prakash S. Procedures for microencapsulation of enzymes, cells and genetically engineered microorganisms. Mol Biotechnol. 2001, 17: 249-60, and Lu MZ, et al., A novel cell encapsulation method using photosensitive poly(allylamine alpha-cyanocinnamylideneacetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S.M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Thechnol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002; 13: 783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T.A. Microfabrication technology for pancreatic cell encapsulation. Expert Opin Biol Ther. 2002, 2: 633-46).

Downregulating Methods and Agents

Downregulation of BNP can be effected on the genomic and/or the transcript level using a variety of molecules which interfere with transcription and/or translation (e.g., antisense, siRNA, Ribozyme, DNAzyme), or on the protein level using e.g., antagonists, enzymes that cleave the polypeptide and the like.

Following is a list of agents capable of downregulating expression level and/or activity of BNP.

One example, of an agent capable of downregulating a BNP polypeptide is an antibody or antibody fragment capable of specifically binding BNP. Preferably, the antibody specifically binds at least one epitope of a BNP as described hereinabove.

An agent capable of downregulating a BNP transcript is a small interfering RNA (siRNA) molecule. RNA interference is a two step process. The first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 bp duplexes (siRNA), each with 2-nucleotide 3' overhangs [Hutvagner and Zamore Curr. Opin. Genetics and Development 12:225-232 (2002); and Bernstein Nature 409:363-366 (2001)].

In the effector step, the siRNA duplexes bind to a nuclease complex to from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al. (2001) Nat. Rev. Gen. 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al. Nat. Rev. Gen. 2:110-119 (2001), Sharp Genes. Dev. 15:485-90 (2001); Hutvagner and Zamore Curr. Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be effected as follows. First, the BNP transcript mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins andlor translation initiation complexes may interfere with binding of the siRNAendonuclease complex [Tuschl, T. 2001, ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (dot ambion dot com/techlib/tn/91/912 dot html).

Second, potential target sites are compared to an appropriate genomic database (e.g., human, mouse, rat etc.) using any sequence alignment software, such as the BLAST software available from the NCBI server (dot ncbidot nlmdot nihdot gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome.

Thus, a scrambled nucleotide sequence of the siRNA is preferably used, provided it does not display any significant homology to any other gene.

Another agent capable of downregulating a BNP transcript is a DNAzyme molecule capable of specifically cleaving an mRNA transcript or DNA sequence of the BNP. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262). A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther. dot asgtdot org). In another application, DNAzymes complementary to bcr-abl oncogenes were successful in inhibiting the oncogenes expression in leukemia cells, and lessening relapse rates in autologous bone marrow transplant in cases of CML and ALL.

Downregulation of a BNP transcript can also be effected by using an antisense polynucleotide capable of specifically hybridizing with an mRNA transcript encoding the BNP.

Design of antisense molecules which can be used to efficiently downregulate a BNP must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)].

More recently, antisense-mediated suppression of human heparanase gene expression has been reported to inhibit pleural dissemination of human cancer cells in a mouse model [Uno et al., Cancer Res 61:7855-60 (2001)].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another agent capable of downregulating a BNP transcript is a ribozyme molecule capable of specifically cleaving an mRNA transcript encoding a BNP. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Another agent capable of downregulating BNP would be any molecule which binds to and/or cleaves BNP. Such molecules can be BNP antagonists, or BNP inhibitory peptide.

It will be appreciated that a non-functional analogue of at least a catalytic or binding portion of BNP can be also used as an agent which downregulates BNP.

Another agent which can be used along with the present invention to downregulate BNP is a molecule which prevents BNP activation or substrate binding.

Each of the upregulating or downregulating agents described hereinabove or the expression vector encoding BNP can be administered to the individual per se or as part of a pharmaceutical composition which also includes a physiologically acceptable carrier. The purpose of a pharmaceutical composition is to facilitate administration of the active ingredient to an organism.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the preparation accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections. Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated. Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Pharmaceutical compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It will be appreciated that treatment of BNP related disease according to the present invention may be combined with other treatment methods known in the art (i.e., combination therapy).

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed.

(1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

The following sections relate to Candidate Marker Examples (first section).

Candidate Marker Examples Section

This Section relates to Examples of sequences according to the present invention.

Description of the Methodology Undertaken to Uncover the Biomolecular Sequences of the Present Invention Human ESTs and cDNAs were obtained from GenBank versions 136 (Jun. 15, 2003 ftp dot ncbidot nihdot gov/genbank/release dot notes/gb 136 dot release dot notes); NCBI genome assembly of April 2003; RefSeq sequences from June 2003; Genbank version 139 (December 2003); Human Genome from NCBI (Build 34) (from October 2003); and RefSeq sequences from December 2003; and from Incyte LifeSeq library (ESTs only; Incyte Corporation (Wilmington, Del., USA)). With regard to GenBank sequences, the human EST sequences from the EST (GBEST) section and the human mRNA sequences from the primate (GBPRI) section were used; also the human nucleotide RefSeq mRNA sequences were used (see for example dot ncbidot nlm nihdot gov/Genbank/GenbankOverview dot html and for a reference to the EST section, see dot ncbidot nlmdot nihdot gov/dbEST/; a general reference to dbEST, the EST database in GenBank, may be found in Boguski et al, Nat Genet. 1993 Aug. 4(4):332-3; all of which are hereby incorporated by reference as if fully set forth herein).

Novel splice variants were predicted using the LEADS clustering and assembly system as described in Sorek, R., Ast, G. & Graur, D. Alu-containing exons are alternatively spliced. Genome Res 12, 1060-7 (2002); U.S. Pat. No. 6,625,545; and U.S. patent application Ser. No. 10/426,002, published as US20040101876 on May 27 2004; all of which are hereby incorporated by reference as if fully set forth herein. Briefly, the software cleans the expressed sequences from repeats, vectors and immunoglobulins. It then aligns the expressed sequences to the genome taking alternatively splicing into account and clusters overlapping expressed sequences into "clusters" that represent genes or partial genes.

These were annotated using the GeneCarta (Compugen, Tel-Aviv, Israel) platform. The GeneCarta platform includes a rich pool of annotations, sequence information (particularly of spliced sequences), chromosomal information, alignments, and additional information such as SNPs, gene ontology terms, expression profiles, functional analyses, detailed domain structures, known and predicted proteins and detailed homology reports.

A brief explanation is provided with regard to the method of selecting the candidates. However, it should be noted that this explanation is provided for descriptive purposes only, and is not intended to be limiting in any way. The potential markers were identified by a computational process that was designed to find genes and/or their splice variants that are specifically expressed in cardiac tissue, as opposed to other types of tissues and also particularly as opposed to muscle tissue, by using databases of expressed sequences. Various parameters related to the information in the EST libraries, determined according to classification by library annotation, were used to assist in locating genes and/or splice variants thereof that are specifically and/or differentially expressed in heart tissues. The detailed description of the selection method and of these parameters is presented in Example 1 below.

Example 1

Identification of Differentially Expressed Gene Products—Algorithm

In order to distinguish between differentially expressed gene products and constitutively expressed genes (i.e., house keeping genes), an algorithm based on an analysis of frequencies was configured. A specific algorithm for identification of transcripts specifically expressed in heart tissue is described hereinbelow.

EST Analysis

ESTs were taken from the following main sources: libraries contained in Genbank version 136 (Jun. 15, 2003 ftp-dotncbidotnihdotgov/genbank/releasedot notes/gb136dot release dot notes) and Genbank version 139 (December 2003); and from the EST portion of LifeSeq, from Incyte Corporation (Wilmington, Del., USA). With regard to GenBank sequences, the human EST sequences from the EST (GBEST) section were used.

Library annotation—EST libraries were manually classified according to:
1. Tissue origin
2. Biological source—Examples of frequently used biological sources for construction of EST libraries include cancer cell-lines; normal tissues; cancer tissues; foetal tissues; and others such as normal cell lines and pools of normal cell-lines, cancer cell-lines and combinations thereof. A specific description of abbreviations used below with regard to these tissues/cell lines etc is given above.
3. Protocol of library construction—various methods are known in the art for library construction including normalized library construction; non-normalized library construction; subtracted libraries; ORESTES and others (described in the annotation available in Genbank). It will be appreciated that at times the protocol of library construction is not indicated in the information available about that library.

The following rules were followed:

EST libraries originating from identical biological samples were considered as a single library.

EST libraries which included above-average levels of contamination, such as DNA contamination for example, were eliminated. The presence of such contamination was determined as follows. For each library, the number of unspliced ESTs that are not fully contained within other spliced sequences was counted. If the percentage of such sequences (as compared to all other sequences) was at least 4 standard deviations above the average for all libraries being analyzed, this library was tagged as being contaminated and was eliminated from further consideration in the below analysis (see also Sorek, R. & Safer, H. M. A novel algorithm for computational identification of contaminated EST libraries. Nucleic Acids Res 31, 1067-74 (2003)for further details).

Clusters (genes) having at least five sequences including at least two sequences from the tissue of interest were analyzed. Splice variants were identified by using the LEADS software package as described above.

Example 2

Identification of Heart Tissue Specific Genes

For detection of heart tissue specific clusters, heart tissue libraries/sequences were compared to the total number of libraries/sequences in the cluster and in Genebank, and to the relevant numbers for muscle tissue libraries/sequences. Statistical tools were employed to identify clusters that were heart tissue specific, both as compared to all other tissues and also in comparison to muscle tissue.

The algorithm—for each tested tissue T and for each tested cluster the following were examined:

1. Each cluster includes at least 2 libraries from the tissue T. At least 3 clones (weighed—as described above) from tissue T in the cluster;

2. The following equation was then used to determine heart tissue-specific expression as compared to expression in all tissue types for a particular cluster:

$$\frac{t}{T} \Big/ \frac{n-t-m}{N-T-M}$$

in which n is the total number of ESTs available for a cluster, while N is the total number of ESTs available in all of the libraries considered in the analysis (effectively all ESTs in Genbank, except for those that were rejected as belonging to contaminated libraries). This ratio was preferably set to be at least about 8, although optionally the ratio could be set to be at least about 5.

3. The following equation was then used to determine heart tissue-specific expression vs. expression in skeletal muscle tissue for a particular cluster: $t/T/m/M$ in which t represents the number of heart tissue-specific ESTs for the cluster, while T is the number of all heart tissue-specific ESTs in the analysis; m is the number of skeletal muscle tissue-specific ESTs for the cluster, while M is the number of all skeletal muscle tissue-specific ESTs in the analysis. This ratio was preferably set to be at least about 4, although optionally the ratio could be set to be at least about 2.

4. Fisher exact test P-values were computed for weighted clone counts to check that the counts are statistically significant according to the following function: $F(t,T,n,N)$ which is the probability of a cluster actually being overexpressed in heart tissue, as compared to its overall level of expression. The P-value was preferably set to be less than about 1e-5, although optionally it could be set to be less than about 1e-3.

Example 3

Experimental and Marker Data

This Example relates to examples of sequences according to the present invention, including experiments involving these sequences, and illustrative, non-limiting examples of methods, assays and uses thereof. The materials and experimental procedures are explained first, as all experiments used them as a basis for the work that was performed.

The markers of the present invention were tested with regard to their expression in various heart and non-heart tissue samples. Unless otherwise noted, all experimental data relates to variants of the present invention, named according to the segment being tested (as expression was tested through RT-PCR as described). A description of the samples used in the panel is provided in Table I below. Tests were then performed as described below.

TABLE 1

Tissue samples in testing panel

| | Lot no. | Source | Tissue | Pathology | Sex/Age |
|---|---|---|---|---|---|
| 1-Am-Colon (C71) | 071P10B | Ambion | Colon | PM | F/43 |
| 2-B-Colon (C69) | A411078 | Biochain | Colon | PM-Pool of 10 | M&F |
| 3-Cl-Colon (C70) | 1110101 | Clontech | Colon | PM-Pool of 3 | M&F |
| 4-Am-Small Intestine | 091P0201A | Ambion | Small Intestine | PM | M/75 |
| 5-B-Small Intestine | A501158 | Biochain | Small Intestine | PM | M/63 |
| 6-B-Rectum | A605138 | Biochain | Rectum | PM | M/25 |
| 7-B-Rectum | A610297 | Biochain | Rectum | PM | M/24 |
| 8-B-Rectum | A610298 | Biochain | Rectum | PM | M/27 |
| 9-Am-Stomach | 110P04A | Ambion | Stomach | PM | M/16 |
| 10-B-Stomach | A501159 | Biochain | Stomach | PM | M/24 |
| 11-B-Esophagus | A603814 | Biochain | Esophagus | PM | M/26 |
| 12-B-Esophagus | A603813 | Biochain | Esophagus | PM | M/41 |
| 13-Am-Pancreas | 071P25C | Ambion | Pancreas | PM | M/25 |
| 14-CG-Pancreas | CG-255-2 | Ichilov | Pancreas | PM | M/75 |
| 15-B-Lung | A409363 | Biochain | Lung | PM | F/26 |
| 16-Am-Lung (L93) | 111P0103A | Ambion | Lung | PM | F/61 |
| 17-B-Lung (L92) | A503204 | Biochain | Lung | PM | M/28 |
| 18-Am-Ovary (O47) | 061P43A | Ambion | Ovary | PM | F/16 |
| 19-B-Ovary (O48) | A504087 | Biochain | Ovary | PM | F/51 |
| 20-B-Ovary (O46) | A504086 | Biochain | Ovary | PM | F/41 |
| 21-Am-Cervix | 101P0101A | Ambion | Cervix | PM | F/40 |
| 22-B-Cervix | A408211 | Biochain | Cervix | PM | F/36 |
| 23-B-Cervix | A504089 | Biochain | Cervix | PM-Pool of 5 | M&F |
| 24-B-Uterus | A411074 | Biochain | Uterus | PM-Pool of 10 | M&F |
| 25-B-Uterus | A409248 | Biochain | Uterus | PM | F/43 |
| 26-B-Uterus | A504090 | Biochain | Uterus | PM-Pool of 5 | M&F |
| 27-B-Bladder | A501157 | Biochain | Bladder | PM | M/29 |

TABLE 1-continued

Tissue samples in testing panel

| | Lot no. | Source | Tissue | Pathology | Sex/Age |
|---|---|---|---|---|---|
| 28-Am-Bladder | 071P02C | Ambion | Bladder | PM | M/20 |
| 29-B-Bladder | A504088 | Biochain | Bladder | PM-Pool of 5 | M&F |
| 30-Am-Placenta | 021P33A | Ambion | Placenta | PB | F/33 |
| 31-B-Placenta | A410165 | Biochain | Placenta | PB | F/26 |
| 32-B-Placenta | A411073 | Biochain | Placenta | PB-Pool of 5 | M&F |
| 33-B-Breast (B59) | A607155 | Biochain | Breast | PM | F/36 |
| 34-Am-Breast (B63) | 26486 | Ambion | Breast | PM | F/43 |
| 35-Am-Breast (B64) | 23036 | Ambion | Breast | PM | F/57 |
| 36-Cl-Prostate (P53) | 1070317 | Clontech | Prostate | PB-Pool of 47 | M&F |
| 37-Am-Prostate (P42) | 061P04A | Ambion | Prostate | PM | M/47 |
| 38-Am-Prostate (P59) | 25955 | Ambion | Prostate | PM | M/62 |
| 39-Am-Testis | 111P0104A | Ambion | Testis | PM | M/25 |
| 40-B-Testis | A411147 | Biochain | Testis | PM | M/74 |
| 41-Cl-Testis | 1110320 | Clontech | Testis | PB-Pool of 45 | M&F |
| 42-CG-Adrenal | CG-184-10 | Ichilov | Adrenal | PM | F/81 |
| 43-B-Adrenal | A610374 | Biochain | Adrenal | PM | F/83 |
| 44-B-Heart | A411077 | Biochain | Heart | PB-Pool of 5 | M&F |
| 45-CG-Heart | CG-255-9 | Ichilov | Heart | PM | M/75 |
| 46-CG-Heart | CG-227-1 | Ichilov | Heart | PM | F/36 |
| 47-Am-Liver | 081P0101A | Ambion | Liver | PM | M/64 |
| 48-CG-Liver | CG-93-3 | Ichilov | Liver | PM | F/19 |
| 49-CG-Liver | CG-124-4 | Ichilov | Liver | PM | F/34 |
| 50-Cl-BM | 1110932 | Clontech | Bone Marrow | PM-Pool of 8 | M&F |
| 51-CGEN-Blood | WBC#5 | CGEN | Blood | | M |
| 52-CGEN-Blood | WBC#4 | CGEN | Blood | | M |
| 53-CGEN-Blood | WBC#3 | CGEN | Blood | | M |
| 54-CG-Spleen | CG-267 | Ichilov | Spleen | PM | F/25 |
| 55-CG-Spleen | 111P0106B | Ambion | Spleen | PM | M/25 |
| 56-CG-Spleen | A409246 | Biochain | Spleen | PM | F/12 |
| 56-CG-Thymus | CG-98-7 | Ichilov | Thymus | PM | F/28 |
| 58-Am-Thymus | 101P0101A | Ambion | Thymus | PM | M/14 |
| 59-B-Thymus | A409278 | Biochain | Thymus | PM | M/28 |
| 60-B-Thyroid | A610287 | Biochain | Thyroid | PM | M/27 |
| 61-B-Thyroid | A610286 | Biochain | Thyroid | PM | M/24 |
| 62-CG-Thyroid | CG-119-2 | Ichilov | Thyroid | PM | F/66 |
| 63-Cl-Salivary Gland | 1070319 | Clontech | Salivary Gland | PM-Pool of 24 | M&F |
| 64-Am-Kidney | 111P0101B | Ambion | Kidney | PM-Pool of 14 | M&F |
| 65-Cl-Kidney | 1110970 | Clontech | Kidney | PM-Pool of 14 | M&F |
| 66-B-Kidney | A411080 | Biochain | Kidney | PM-Pool of 5 | M&F |
| 67-CG-Cerebellum | CG-183-5 | Ichilov | Cerebellum | PM | M/74 |
| 68-CG-Cerebellum | CG-212-5 | Ichilov | Cerebellum | PM | M/54 |
| 69-B-Brain | A411322 | Biochain | Brain | PM | M/28 |
| 70-Cl-Brain | 1120022 | Clontech | Brain | PM-Pool of 2 | M&F |
| 71-B-Brain | A411079 | Biochain | Brain | PM-Pool of 2 | M&F |
| 72-CG-Brain | CG-151-1 | Ichilov | Brain | PM | F/86 |
| 73-Am-Skeletal Muscle | 101P013A | Ambion | Skeletal Muscle | PM | F/28 |
| 74-Cl-Skeletal Muscle | 1061038 | Clontech | Skeletal Muscle | PM-Pool of 2 | M&F |

Materials and Experimental Procedures

RNA preparation—RNA was obtained from Clontech (Franklin Lakes, N.J. USA 07417, dot clontechdot com), BioChain Inst. Inc. (Hayward, Calif. 94545 USA www.biochain.com), ABS (Wilmington, Del. 19801, USA, dot abs-bioreagentsdot com) or Ambion (Austin, Tex. 78744 USA, dot ambiondot com). Alternatively, RNA was generated from tissue samples using TRI-Reagent (Molecular Research Center), according to Manufacturer's instructions. Tissue and RNA samples were obtained from patients or from postmortem. Total RNA samples were treated with DNaseI (Ambion) and purified using RNeasy columns (Qiagen).

RT PCR—Purified RNA (1 µg) was mixed with 150 ng Random Hexamer primers (Invitrogen) and 500 µM dNTP in a total volume of 15.6 µl. The mixture was incubated for 5 min at 65° C. and then quickly chilled on ice. Thereafter, 5 µl of 5X SuperscriptII first strand buffer (Invitrogen), 2.4 µl 0.1 M DTT and 40 units RNasin (Promega) were added, and the mixture was incubated for 10 min at 25° C., followed by further incubation at 42° C. for 2 min. Then, 1 µl (200units) of SuperscriptII (Invitrogen) was added and the reaction (final volume of 25 µl) was incubated for 50 min at 42° C. and then inactivated at 70° C. for 15 min. The resulting cDNA was diluted 1:20 in TE buffer (10 mM Tris pH=8, mM EDTA pH=8).

Figure 1:
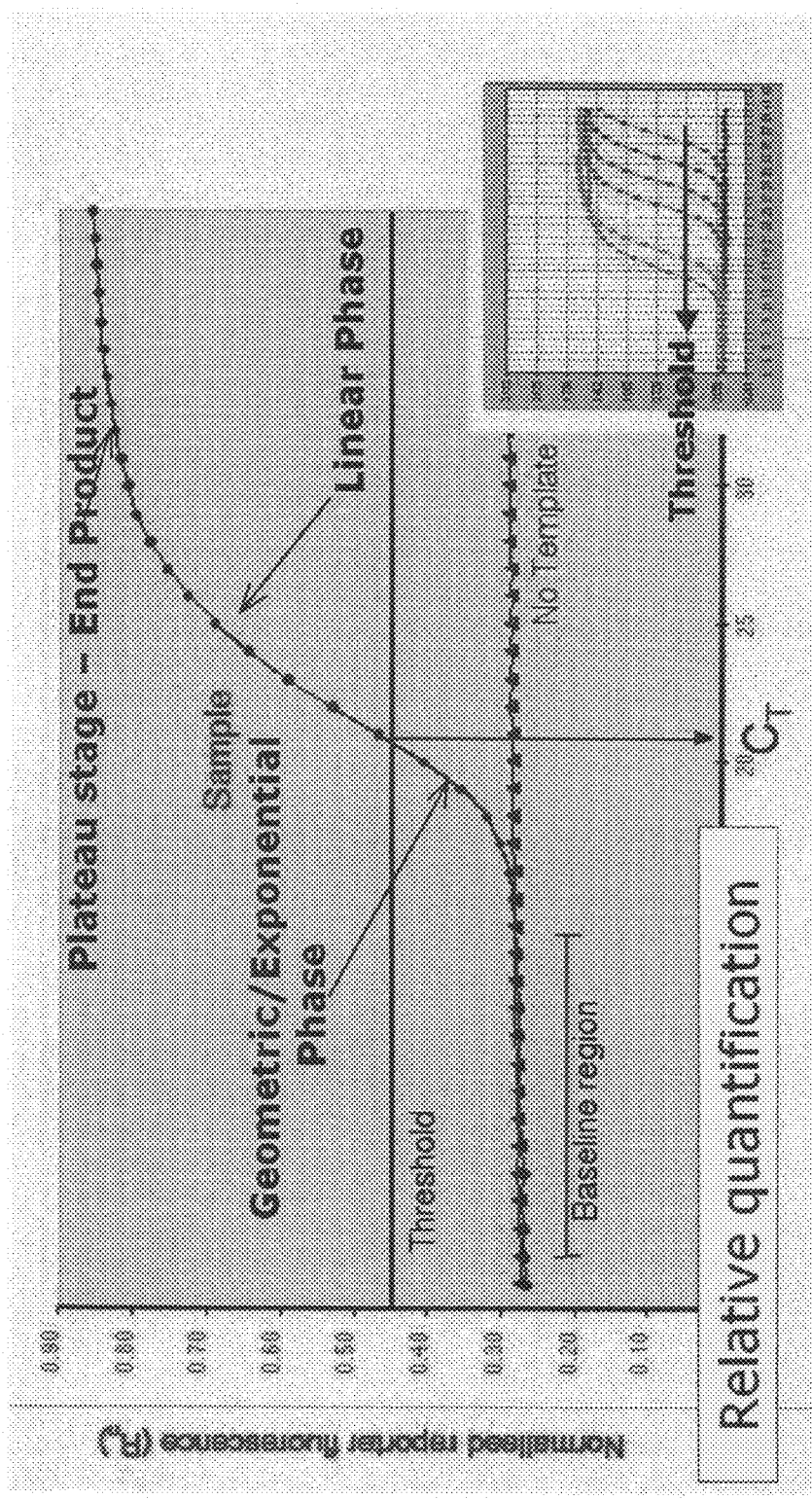

Real-Time RT-PCR analysis-cDNA (51µl), prepared as described above, was used as a template in Real-Time PCR reactions using the SYBR Green I assay (PE Applied Biosystem) with specific primers and UNG Enzyme (Eurogentech or ABI or Roche). The amplification was effected as follows: 50° C. for 2 min, 95° C. for 10 min, and then 40 cycles of 95° C. for 15 sec, followed by 60° C. for 1 min. Detection was performed by using the PE Applied Biosystem SDS 7000. The cycle in which the reactions achieved a threshold level (Ct) of fluorescence was registered and was used to calculate the relative transcript quantity in the RT reactions. The relative quantity was calculated using the equation $Q = \text{efficiency}^{-Ct}$. The efficiency of the PCR reaction was calculated from a standard curve, created by using serial dilutions of several reverse transcription (RT) reactions To minimize inherent differences in the RT reaction, the resulting relative quantities were normalized to the geometric mean of the relative quantities of several housekeeping (HSKP) genes. Schematic summary of quantitative real-time PCR analysis is presented in FIG. 1. As shown, the x-axis shows the cycle number. The $C_T$=Threshold Cycle point, which is the cycle that the amplification curve crosses the fluorescence threshold that was set in the experiment. This point is a calculated cycle number in which PCR products signal is above the background level (passive dye ROX) and still in the Geometric/Exponential phase (as shown, once the level of fluorescence crosses the measurement threshold, it has a geometrically increasing phase, during which measurements are most accurate, followed by a linear phase and a plateau phase; for quantitative measurements, the latter two phases do not provide accurate measurements). The y-axis shows the normalized reporter fluorescence. It should be noted that this type of analysis provides relative quantification.

The sequences of the housekeeping genes measured in all the examples on normal tissue samples panel were as follows:

```
RPL19 (GenBank Accession No. NM_000981),
                                       (SEQ ID NO:43)
RPL19 Forward primer:
                                       (SEQ ID NO:30)
TGGCAAGAAGAAGGTCTGGTTAG RPL19 Reverse primer:
                                       (SEQ ID NO:31)
TGATCAGCCCATCTTTGATGAG RPL19-amplicon:
                                       (SEQ ID NO:32)
TGGCAAGAAGAAGGTCTGGTTAGACCCCAATGAGACCAATGAAATCGCCA
ATGCCAACTCCCGTCAGCAGATCCGGAAGCTCATCAAAGATGGGCTGATC
A TATA box (GenBank Accession No. NM_003194),
                                       (SEQ ID NO:44)
TATA box Forward primer:
                                       (SEQ ID NO:33)
CGGTTTGCTGCGGTAATCAT TATA box Reverse primer:
                                       (SEQ ID NO:34)
TTTCTTGCTGCCAGTCTGGAC TATA box-amplicon:
                                       (SEQ ID NO:35)
CGGTTTGCTGCGGTAATCATGAGGATAAGAGAGCCACGAACCACGGCACT
GATTTTCAGTTCTGGGAAAATGGTGTGCACAGGAGCCAAGAGTGAAGAAC
AGTCCAGACTGGCAGCAAGAAA Ubiquitin (GenBank Accession No. BC000449)
                                       (SEQ ID NO:45)
Ubiquitin Forward primer:
                                       (SEQ ID NO:36)
ATTTGGGTCGCGGTTCTTG Ubiquitin Reverse primer:
                                       (SEQ ID NO:37)
TGCCTTGACATTCTCGATGGT Ubiquitin-amplicon:
                                       (SEQ ID NO:38)
ATTTGGGTCGCGGTTCTTGTTTGTGGATCGCTGTGATCGTCACTTGACAA
TGCAGATCTTCGTGAAGACTCTGACTGGTAAGACCATCACCCTCGAGGTT
GAGCCCAGTGACACCATCGAGAATGTCAAGGCA SDHA (GenBank Accession No. NM_004168)
                                       (SEQ ID NO:46)

-continued
SDHA Forward primer:
                                       (SEQ ID NO:39)
TGGGAACAAGAGGGCATCTG SDHA Reverse primer:
                                       (SEQ ID NO:40)
CCACCACTGCATCAAATTCATG SDHA-amplicon:
                                       (SEQ ID NO:41)
TGGGAACAAGAGGGCATCTGCTAAAGTTTCAGATTCCATTTCTGCTCAGT
ATCCAGTAGTGGATCATGAATTTGATGCAGTGGTGG
```

Description for Cluster Humnatpep

Cluster HUMNATPEP features 4 transcript(s) and 7 segment(s) of interest, the names for which are given in Tables 1 and 2, respectively, the sequences themselves are given at the end of the application. The selected protein variants are given in table 3.

TABLE 1

Transcripts of interest

| Transcript Name | SEQ ID NOS |
|---|---|
| HUMNATPEP_PEA_1_T1 | 1 |
| HUMNATPEP_PEA_1_T2 | 2 |
| HUMNATPEP_PEA_1_T3 | 2 |
| HUMNATPEP_PEA_1_T4 | 4 |

TABLE 2

Segments of interest

| Segment Name | SEQ ID NOS |
|---|---|
| HUMNATPEP_PEA_1_node_0 (SEQ ID NO: 5) | 5 |
| HUMNATPEP_PEA_1_node_1 (SEQ ID NO: 6) | 6 |
| HUMNATPEP_PEA_1_node_2 (SEQ ID NO: 7) | 7 |
| HUMNATPEP_PEA_1_node_3 (SEQ ID NO: 8) | 8 |
| HUMNATPEP_PEA_1_node_4 (SEQ ID NO: 9) | 9 |
| HUMNATPEP_PEA_1_node_5 (SEQ ID NO: 10) | 10 |
| HUMNATPEP_PEA_1_node_6 (SEQ ID NO: 11) | 11 |

TABLE 3

Proteins of interest

| Protein Name | SEQ ID NOS |
|---|---|
| HUMNATPEP_PEA_1_P2 (SEQ ID NO: 13) | 13 |
| HUMNATPEP_PEA_1_P3 (SEQ ID NO: 14) | 14 |
| HUMNATPEP_PEA_1_P7 (SEQ ID NO: 15) | 15 |

These sequences are variants of the known protein Natriuretic peptides B precursor (SEQ ID NO: 12) [Contains: Gamma-brain natriuretic peptide; Brain natriuretic peptide 32 (BNP-32)] (SwissProt accession identifier ANFB_HUMAN), referred to herein as the previously known protein.

Protein Natriuretic peptides B precursor (SEQ ID NO: 12) [Contains: Gamma-brain natriuretic peptide; Brain natriuretic peptide 32 (BNP-32)] is known or believed to have the following function(s): Acts as a cardiac hormone with a variety of biological actions including natriuresis, diuresis, vasorelaxation, and inhibition of renin and aldosterone secretion. It is thought to play a key role in cardiovascular homeostasis. Helps restore the body's salt and water balance. Improves heart function. The sequence for protein Natriuretic peptides B precursor (SEQ ID NO: 12) [Contains: Gamma-brain natriuretic peptide; Brain natriuretic peptide 32 (BNP-32)] is given at the end of the application, as "Natriuretic peptides B precursor (SEQ ID NO: 12) [Contains: Gamma-brain natriuretic peptide; Brain natriuretic peptide 32 (BNP-32)] amino acid sequence" (SEQ ID NO: 12). Known polymorphisms for this sequence are as shown in Table 4.

TABLE 4

Amino acid mutations for Known Protein

SNP position(s) on
amino acid sequence Comment

| | |
|---|---|
| 25 | R -> L (in dbSNP: 5227). /FTId = VAR_014580. |
| 47 | R -> H (in dbSNP: 5229). /FTId = VAR_014581. |
| 93 | M -> L (in dbSNP: 5230). /FTId = VAR_014582. |

Protein Natriuretic peptides B precursor (SEQ ID NO: 12) [Contains: Gamma-brain natriuretic peptide; Brain natriuretic peptide 32 (BNP-32)] localization is believed to be Secreted.

The previously known protein also has the following indication(s) and/or potential therapeutic use(s): Hepatic dysfunction, general; Hypertension, general; Heart failure; Asthma; Renal failure. It has been investigated for clinical/therapeutic use in humans, for example as a target for an antibody or small molecule, and/or as a direct therapeutic; available information related to these investigations is as follows. Potential pharmaceutically related or therapeutically related activity or activities of the previously known protein are as follows: Atrial peptide agonist; Diuretic. A therapeutic role for a protein represented by the cluster has been predicted. The cluster was assigned this field because there was information in the drug database or the public databases (e.g., described herein above) that this protein, or part thereof, is used or can be used for a potential therapeutic indication: Hepatoprotective; Antihypertensive; Antihypertensive, diuretic; Cardiostimulant; Vasodilator, coronary; Urological; Antiasthma; COPD treatment.

The following GO Annotation(s) apply to the previously known protein. The following annotation(s) were found: fluid secretion, cell surface receptor linked signal transduction, diuresis, natriuresis, negative regulation of angiogenesis, negative regulation of cell growth, regulation of blood pressure, regulation of vascular permeability, regulation of vasodilation which are annotation(s) related to Biological Process; diuretic hormone, which are annotation(s) related to Molecular Function; and extracellular space, which are annotation(s) related to Cellular Component.

The GO assignment relies on information from one or more of the SwissProt/TremB1 Protein knowledgebase, available from dot expasydot ch/sprot; or Locuslink, available from ncbidot nlmdot nihdot gov/projects/LocusLink.

The heart-selective diagnostic marker prediction engine provided the following results with regard to cluster HUMNATPEP. Predictions were made for selective expression of transcripts of this clusterin heart tissue, according to the previously described methods. The numbers on the y-axis of FIG. 2 below refer to weighted expression of ESTs in each category, as "parts per million" (ratio of the expression of ESTs for a particular cluster to the expression of all ESTs in that category, according to parts per million).

Overall, the following results were obtained as shown with regard to the histogram in FIG. 2, concerning the number of heart-specific clones in libraries/sequences.

This cluster was found to be selectively expressed in heart for the following reasons: in a comparison of the ratio of expression of the cluster in heart specific ESTs to the overall expression of the cluster in non-heart ESTs, which was found to be 18.3. Also the expression levels of this gene in muscle was negligible; and fisher exact test P-values were computed both for library and weighted clone counts to check that the counts are statistically significant, and were found to be 3.40E-17.

One particularly important measure of specificity of expression of a cluster in heart tissue is the previously described comparison of the ratio of expression of the cluster in heart as opposed to muscle. This cluster was found to be specifically expressed in heart as opposed to non-heart ESTs as described above. However, many proteins have been shown to be generally expressed at a higher level in both heart and muscle, which is less desirable. For this cluster, as described above, the expression levels of this gene in muscle was negligible, which clearly supports specific expression in heart tissue.

As noted above, cluster HUMNATPEP features 4 transcript(s), which were listed in Table 1 above. These transcript(s) encode for protein(s) which are variant(s) of protein Natriuretic peptides B precursor (SEQ ID NO: 12) [Contains: Gamma-brain natriuretic peptide; Brain natriuretic peptide 32 (BNP-32)]. A description of each variant protein according to the present invention is now provided.

Variant protein HUMNATPEP_PEA_1_P2 (SEQ ID NO: 13) according to the present invention has an amino acid sequence as given at the end of the application; it is encoded by transcript(s) HUMNATPEP_PEA_1_T1 (SEQ ID NO: 1). BNP splice variant HUMNATPEP_PEA_1_T1 (SEQ ID NO: 1) results from alternative splicing of the BNP gene, thus leading to the extension of exon 2 into the intron and to the generation of an extended 162 amino acid long protein, compared to the 134 amino acid long wild type protein. The protein encoded by this transcript contains the signal P (signal peptide) and the complete natriuretic peptide domain plus a unique sequence of 33 amino acids in its C-terminus.

An alignment is given to the known protein (Natriuretic peptides B precursor (SEQ ID NO: 12) [Contains: Gamma-brain natriuretic peptide; Brain natriuretic peptide 32 (BNP-32)]) at the end of the application. One or more alignments to one or more previously published protein sequences are given at the end of the application. A brief description of the relationship of the variant protein according to the present invention to each such aligned protein is as follows:

Comparison report between HUMNATPEP_PEA_1_P2 (SEQ ID NO: 13) and ANFB_HUMAN:

1. An isolated chimeric polypeptide encoding for HUMNATPEP_PEA_1_P2 (SEQ ID NO: 13), comprising a first amino acid sequence being at least 90% homologous to MDPQTAPSRALLLLLFLHLAFLGGRSH-PLGSPGSASDLETS-GLQEQRNHLQGKLSELQVEQTSLEPLQE-SPRPTGVWKSREVATEGIRGHRKMVLYTLRAPRSP KMVQGSGCFGRKMDRISSSSGLGCK corresponding to amino acids 1-129 of ANFB_HUMAN, which also corresponds to amino acids 1-129 of HUMNATPEP_PEA_1_P2 (SEQ ID NO: 13), and a second amino acid sequence being at least 70%, optionally at least 80%, preferably at least 85%, more preferably at least 90% and most preferably at least 95% homologous to a polypeptide having the sequence GKHPLPPRPPSPIPVCDTVRVTLGFVVSGNHTL corresponding to amino acids 130-162 of HUMNATPEP_PEA_1_P2 (SEQ ID NO: 13), wherein said first and second amino acid sequences are contiguous and in a sequential order.

2. An isolated polypeptide encoding for a tail of HUMNATPEP_PEA_1_P2 (SEQ ID NO: 13), comprising a polypeptide being at least 70%, optionally at least about 80%, preferably at least about 85%, more preferably at least about 90% and most preferably at least about 95% homologous to the sequence GKHPLPPRPPSPIPVCDTVRVTLGFVVSGNHTL in HUMNATPEP_PEA_1_P2 (SEQ ID NO: 13).

According to another aspect of the present invention there is provided a bridge fragment of HUMNATPEP_PEA_1_P2 (SEQ ID NO: 13) between 10 and 50 amino acids in length that spans the first and second amino acid sequences described above.

There is provided a bridge portion of HUMNATPEP_PEA_1_P2 (SEQ ID NO: 13), comprising a polypeptide having a length "n", wherein n is at least about 10 amino acids in length, optionally at least about 20 amino acids in length, preferably at least about 30 amino acids in length, more preferably at least about 40 amino acids in length and most preferably at least about 50 amino acids in length, wherein at least two amino acids comprise KG, having a structure as follows (numbering according to SEQ ID NO:1): a sequence starting from any of amino acid numbers 129-x to 129; ending at any of amino acid numbers 130+((n−2)−x), in which x varies from 0 to n−2, such that the value ((n−2)−x) is not allowed to be larger than 32.

For example, for peptides of 10 amino acids (such that n=10), the starting position could be as "early" in the sequence as amino acid number 121 if x=n−2=8(ie 121=129−8), such that the peptide would end at amino acid number 130 (130+(8−8=0)). On the other hand, the peptide could start at amino acid number 129 if x=0(ie 129=129−0), and could end at amino acid 138 (130+(8−0=8)).

The bridge portion above may also optionally comprise a polypeptide being at least 70%, optionally at least about 80%, preferably at least about 85%, more preferably at least about 90% and most preferably at least about 95% homologous to at least one sequence described above.

Similarly, the bridge portion may optionally be relatively short, such as from about 4 to about 9 amino acids in length. For four amino acids, the first bridge portion would comprise the following peptides: GCKG, CKGK, KGKH. All peptides feature KG as a portion thereof. Peptides of from about five to about nine amino acids could optionally be similarly constructed.

The location of the variant protein was determined according to results from a number of different software programs and analyses, including analyses from SignalP and other specialized programs. The variant protein is believed to be located as follows with regard to the cell: secreted. The protein localization is believed to be secreted because both signal-peptide prediction programs predict that this protein has a signal peptide, and neither trans-membrane region prediction program predicts that this protein has a trans-membrane region.

The variant protein has the following domains, as determined by using InterPro. The domains are described in Table 6:

TABLE 6

InterPro domain(s)

| InterPro ID | Domain description | Analysis type | Position(s) on protein |
| --- | --- | --- | --- |
| IPR000663 | Natriuretic peptide | FPrintScan | 109-118, 118-127 |
| IPR002408 | Natriuretic peptide, brain type | FPrintScan | 11-27, 110-120, 120-133, 28-38, 43-61 |
| IPR000663 | Natriuretic peptide | HMMPfam | 46-128 |
| IPR000663 | Natriuretic peptide | HMMSmart | 105-128 |
| IPR000663 | Natriuretic peptide | ScanRegExp | 112-128 |
| IPR000663 | Natriuretic peptide | BlastProDom | 27-129 |

Figure 3A:
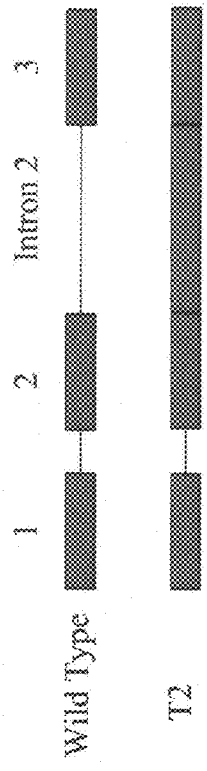
Figure 3B:
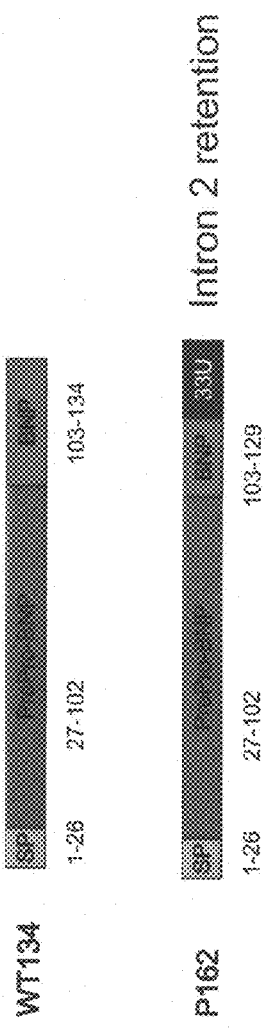

FIG. 3A shows a comparison of the genomic structure for the variant transcript HUMNATPEP_PEA_1_T1 (SEQ ID NO: 1) and the known or "WT" transcript. FIG. 3B shows a comparison of the structure of the variant protein HUMNATPEP_PEA_1_P2 (SEQ ID NO: 13) in comparison to the structure of the known or "WT" protein.

Variant protein HUMNATPEP_PEA_1_P2 (SEQ ID NO: 13) also has the following non-silent SNPs (Single Nucleotide Polymorphisms) as listed in Table 7, (given according to their position(s) on the amino acid sequence, with the alternative amino acid(s) listed; the last column indicates whether the SNP is known or not; the presence of known SNPs in variant protein HUMNATPEP_PEA_1_P2 (SEQ ID NO: 13) sequence provides support for the deduced sequence of this variant protein according to the present invention).

TABLE 7

Amino acid mutations

| SNP position(s) on amino acid sequence | Alternative amino acid(s) | Previously known SNP? |
| --- | --- | --- |
| 25 | R -> L | Yes |
| 47 | R -> H | Yes |
| 93 | M -> L | Yes |

Variant protein HUMNATPEP_PEA_1_P2 (SEQ ID NO: 13) is encoded by the following transcript(s): HUMNATPEP_PEA_1_T1 (SEQ ID NO: 1), for which the sequence(s) is/are given at the end of the application. The coding portion of transcript HUMNATPEP_PEA_1_T1 (SEQ ID NO: 1) is shown in bold; this coding portion starts at position 249 and ends at position 734. The transcript also has the following SNPs as listed in Table 8 (given according to their position on the nucleotide sequence, with the alternative nucleic acid listed; the last column indicates whether the SNP is known or not; the presence of known SNPs in variant protein HUMNATPEP_PEA_1_P2 (SEQ ID NO: 13) sequence provides support for the deduced sequence of this variant protein according to the present invention).

TABLE 8

Nucleic acid SNPs

| SNP position on nucleotide sequence | Alternative nucleic acid | Previously known SNP? |
| --- | --- | --- |
| 198 | A -> T | Yes |
| 322 | G -> T | Yes |
| 388 | G -> A | Yes |
| 525 | A -> T | Yes |

TABLE 8-continued

Nucleic acid SNPs

| SNP position on nucleotide sequence | Alternative nucleic acid | Previously known SNP? |
|---|---|---|
| 888 | C -> T | Yes |
| 1279 | -> T | No |

Variant protein HUMNATPEP_PEA_1_P3 (SEQ ID NO: 14) according to the present invention has an amino acid sequence as given at the end of the application; it is encoded by transcript(s) HUMNATPEP_PEA_1_T2 (SEQ ID NO: 2) and HUMNATPEP_PEA_1_T3 (SEQ ID NO: 3). An alignment is given to the known protein (Natriuretic peptides B precursor (SEQ ID NO: 12) [Contains: Gamma-brain natriuretic peptide; Brain natriuretic peptide 32 (BNP-32)]) at the end of the application. One or more alignments to one or more previously published protein sequences are given at the end of the application. A brief description of the relationship of the variant protein according to the present invention to each such aligned protein is as follows:

Comparison report between HUMNATPEP_PEA_1_P3 (SEQ ID NO: 14) and ANFB_HUMAN:

1. An isolated chimeric polypeptide encoding for HUMNATPEP_PEA_1_P3 (SEQ ID NO: 14), comprising a first amino acid sequence being at least 90% homologous to MDPQTAPSRALLLLLFLHLAFLGGRSH-PLGSPGSASDLETSGLQ corresponding to amino acids 1-44 of ANFB_HUMAN, which also corresponds to amino acids 1-44 of HUMNATPEP_PEA_1_P3 (SEQ ID NO: 14), and a second amino acid sequence being at least 70%, optionally at least 80%, preferably at least 85%, more preferably at least 90% and most preferably at least 95% homologous to a polypeptide having the sequence VRAEGSSGGLDSSNERVLTCCPKRPSSFLWN (SEQ ID NO: 43) corresponding to amino acids 45-75 of HUMNATPEP_PEA_1_P3 (SEQ ID NO: 14), wherein said first and second amino acid sequences are contiguous and in a sequential order.

2. An isolated polypeptide encoding for a tail of HUMNATPEP_PEA_1_P3 (SEQ ID NO: 14), comprising a polypeptide being at least 70%, optionally at least about 80%, preferably at least about 85%, more preferably at least about 90% and most preferably at least about 95% homologous to the sequence VRAEGSSGGLDSSNERVLTCCP-KRPSSFLWN (SEQ ID NO: 43) in HUMNATPEP_PEA_1_P3 (SEQ ID NO: 14).

The location of the variant protein was determined according to results from a number of different software programs and analyses, including analyses from SignalP and other specialized programs. The variant protein is believed to be located as follows with regard to the cell: secreted. The protein localization is believed to be secreted because both signal-peptide prediction programs predict that this protein has a signal peptide, and neither trans-membrane region prediction program predicts that this protein has a trans-membrane region.

Variant protein HUMNATPEP_PEA_1_P3 (SEQ ID NO: 14) also has the following non-silent SNPs (Single Nucleotide Polymorphisms) as listed in Table 9, (given according to their position(s) on the amino acid sequence, with the alternative amino acid(s) listed; the last column indicates whether the SNP is known or not; the presence of known SNPs in variant protein HUMNATPEP_PEA_1_P3 (SEQ ID NO: 14) sequence provides support for the deduced sequence of this variant protein according to the present invention).

TABLE 9

Amino acid mutations

| SNP position(s) on amino acid sequence | Alternative amino acid(s) | Previously known SNP? |
|---|---|---|
| 25 | R -> L | Yes |

Variant protein HUMNATPEP_PEA_1_P3 (SEQ ID NO: 14) is encoded by the following transcript(s): HUMNATPEP_PEA_1_T2 (SEQ ID NO: 2) and HUMNATPEP_PEA_1_T3 (SEQ ID NO: 3), for which the sequence(s) is/are given at the end of the application. The coding portion of transcript HUMNATPEP_PEA_1_T2 (SEQ ID NO: 2) and HUMNATPEP_PEA_1_T3 (SEQ ID NO: 3) are shown in bold; this coding portion starts at position 249 and ends at position 473. The transcript also has the following SNPs as listed in Table 10 (given according to their position on the nucleotide sequence, with the alternative nucleic acid listed; the last column indicates whether the SNP is known or not; the presence of known SNPs in variant protein HUMNATPEP_PEA_1_P3 (SEQ ID NO: 14) sequence provides support for the deduced sequence of this variant protein according to the present invention).

TABLE 10

Nucleic acid SNPs

| SNP positon on nucleotide sequence | Alternative nucleic acid | Previously known SNP? |
|---|---|---|
| 198 | A -> T | Yes |
| 322 | G -> T | Yes |
| 598 | C -> G | Yes |
| 620 | G -> A | Yes |
| 757 | A -> T | Yes |
| 969 | -> T | No |

Variant protein HUMNATPEP_PEA_1_P7 (SEQ ID NO: 15) according to the present invention has an amino acid sequence as given at the end of the application; it is encoded by transcript(s) HUMNATPEP_PEA_1_T4 (SEQ ID NO: 4). An alignment is given to the known protein (Natriuretic peptides B precursor (SEQ ID NO: 12) [Contains: Gamma-brain natriuretic peptide; Brain natriuretic peptide 32 (BNP-32)]) at the end of the application. One or more alignments to one or more previously published protein sequences are given at the end of the application. A brief description of the relationship of the variant protein according to the present invention to each such aligned protein is as follows:

Comparison report between HUMNATPEP_PEA_1_P7 (SEQ ID NO: 15) and ANFB_HUMAN:

1. An isolated chimeric polypeptide encoding for HUMNATPEP_PEA_1_P7 (SEQ ID NO: 15), comprising a first amino acid sequence being at least 90% homologous to MVLYTLRAPRSPKMVQGSGCFGRKM-DRISSSSGLGCKVLRRH corresponding to amino acids 93-134 of ANFB_HUMAN, which also corresponds to amino acids 1-42 of HUMNATPEP_PEA_1_P7 (SEQ ID NO: 15).

The location of the variant protein was determined according to results from a number of different software programs and analyses, including analyses from SignalP and other specialized programs. The variant protein is believed to be located as follows with regard to the cell: intracellularly. The protein localization is believed to be intracellular because neither of the trans-membrane region prediction programs predicted a trans-membrane region for this protein. In addition both signal-peptide prediction programs predict that this protein is a non-secreted protein.

Variant protein HUMNATPEP_PEA_1_P7 (SEQ ID NO: 15) is encoded by the following transcript(s): HUMNATPEP_PEA_1_T4 (SEQ ID NO: 4), for which the sequence(s) is/are given at the end of the application. The coding portion of transcript HUMNATPEP_PEA_1_T4 (SEQ ID NO: 4) is shown in bold; this coding portion starts at position 257 and ends at position 382. The transcript also has the following SNPs as listed in Table 11 (given according to their position on the nucleotide sequence, with the alternative nucleic acid listed; the last column indicates whether the SNP is known or not; the presence of known SNPs in variant protein HUMNATPEP_PEA_1_P7 (SEQ ID NO: 15) sequence provides support for the deduced sequence of this variant protein according to the present invention).

TABLE 11

Nucleic acid SNPs

| SNP position on nucleotide sequence | Alternative nucleic acid | Previously known SNP? |
|---|---|---|
| 198 | A -> T | Yes |
| 257 | A -> T | Yes |
| 469 | -> T | No |

As noted above, cluster HUMNATPEP features 7 segment(s), which were listed in Table 2 above and for which the sequence(s) are given at the end of the application. These segment(s) are portions of nucleic acid sequence(s) which are described herein separately because they are of particular interest. A description of each segment according to the present invention is now provided.

Segment cluster HUMNATPEP_PEA_1_node_0 (SEQ ID NO: 5) according to the present invention is supported by 21 libraries. The number of libraries was determined as previously described. This segment can be found in the following transcript(s): HUMNATPEP_PEA_1_T1 (SEQ ID NO: 1), HUMNATPEP_PEA_1_T2 (SEQ ID NO: 2), HUMNATPEP_PEA_1_T3 (SEQ ID NO: 3) and HUMNATPEP_PEA_1_T4 (SEQ ID NO: 4). Table 12 below describes the starting and ending position of this segment on each transcript.

TABLE 12

Segment location on transcripts

| Transcript name | Segment starting position | Segment ending position |
|---|---|---|
| HUMNATPEP_PEA_1_T1 (SEQ ID NO: 1) | 1 | 240 |
| HUMNATPEP_PEA_1_T2 (SEQ ID NO: 2) | 1 | 240 |
| HUMNATPEP_PEA_1_T3 (SEQ ID NO: 3) | 1 | 240 |
| HUMNATPEP_PEA_1_T4 (SEQ ID NO: 4) | 1 | 240 |

Segment cluster HUMNATPEP_PEA_1_node_1 (SEQ ID NO: 6) according to the present invention is supported by 24 libraries. The number of libraries was determined as previously described. This segment can be found in the following transcript(s): HUMNATPEP_PEA_1_T1 (SEQ ID NO: 1), HUMNATPEP_PEA_1_T2 (SEQ ID NO: 2) and HUMNATPEP_PEA_1_T3 (SEQ ID NO: 3). Table 13 below describes the starting and ending position of this segment on each transcript.

TABLE 13

Segment location on transcripts

| Transcript name | Segment starting position | Segment ending position |
|---|---|---|
| HUMNATPEP_PEA_1_T1 (SEQ ID NO: 1) | 241 | 380 |
| HUMNATPEP_PEA_1_T2 (SEQ ID NO: 2) | 241 | 380 |
| HUMNATPEP_PEA_1_T3 (SEQ ID NO: 3) | 241 | 380 |

Segment cluster HUMNATPEP_PEA_1_node_2 (SEQ ID NO: 7) according to the present invention is supported by 6 libraries. The number of libraries was determined as previously described. This segment can be found in the following transcript(s): HUMNATPEP_PEA_1_T2 (SEQ ID NO: 2) and HUMNATPEP_PEA_1_T3 (SEQ ID NO: 3). Table 14 below describes the starting and ending position of this segment on each transcript.

TABLE 14

Segment location on transcripts

| Transcript name | Segment starting position | Segment ending position |
|---|---|---|
| HUMNATPEP_PEA_1_T2 (SEQ ID NO: 2) | 381 | 612 |
| HUMNATPEP_PEA_1_T3 (SEQ ID NO: 3) | 381 | 612 |

Segment cluster HUMNATPEP_PEA_1_node_3 (SEQ ID NO: 8) according to the present invention is supported by 25 libraries. The number of libraries was determined as previously described. This segment can be found in the following transcript(s): HUMNATPEP_PEA-1-T1 (SEQ ID NO: 1), HUMNATPEP_PEA_1_T2 (SEQ ID NO: 2) and HUMNATPEP_PEA_1_T3 (SEQ ID NO: 3). Table 15 below describes the starting and ending position of this segment on each transcript.

TABLE 15

Segment location on transcripts

| Transcript name | Segment starting position | Segment ending position |
|---|---|---|
| HUMNATPEP_PEA_1_T1 (SEQ ID NO: 1) | 381 | 508 |
| HUMNATPEP_PEA_1_T2 (SEQ ID NO: 2) | 613 | 740 |
| HUMNATPEP_PEA_1_T3 (SEQ ID NO: 3) | 613 | 740 |

Segment cluster HUMNATPEP_PEA_1_node_4 (SEQ ID NO: 9) according to the present invention is supported by 24 libraries. The number of libraries was determined as previously described. This segment can be found in the following transcript(s): HUMNATPEP_PEA_1_T1 (SEQ ID NO: 1), HUMNATPEP_PEA_1_T2 (SEQ ID NO: 2), HUMNATPEP_PEA_1_T3 (SEQ ID NO: 3) and HUMNATPEP_PEA_1_T4 (SEQ ID NO: 4). Table 16 below describes the starting and ending position of this segment on each transcript.

TABLE 16

Segment location on transcripts

| Transcript name | Segment starting position | Segment ending position |
|---|---|---|
| HUMNATPEP_PEA_1_T1 (SEQ ID NO: 1) | 509 | 636 |
| HUMNATPEP_PEA_1_T2 (SEQ ID NO: 2) | 741 | 868 |
| HUMNATPEP_PEA_1_T3 (SEQ ID NO: 3) | 741 | 868 |
| HUMNATPEP_PEA_1_T4 (SEQ ID NO: 4) | 241 | 368 |

Segment cluster HUMNATPEP_PEA_1_node_5 (SEQ ID NO: 10) according to the present invention is supported by 4 libraries. The number of libraries was determined as previously described. This segment can be found in the following transcript(s): HUMNATPEP_PEA_1_T1 (SEQ ID NO: 1) and HUMNATPEP_PEA_1_T3 (SEQ ID NO: 3). Table 17 below describes the starting and ending position of this segment on each transcript.

TABLE 17

Segment location on transcripts

| Transcript name | Segment starting position | Segment ending position |
|---|---|---|
| HUMNATPEP_PEA_1_T1 (SEQ ID NO: 1) | 637 | 1178 |
| HUMNATPEP_PEA_1_T3 (SEQ ID NO: 3) | 869 | 1410 |

Segment cluster HUMNATPEP_PEA_1_node_6 (SEQ ID NO: 11) according to the present invention is supported by 20 libraries. The number of libraries was determined as previously described. This segment can be found in the following transcript(s): HUMNATPEP_PEA_1_T1 (SEQ ID NO: 1), HUMNATPEP_PEA_1_T2 (SEQ ID NO: 2), HUMNATPEP_PEA_1_T3 (SEQ ID NO: 3) and HUMNATPEP_PEA_1_T4 (SEQ ID NO: 4. Table 18 below describes the starting and ending position of this segment on each transcript.

TABLE 18

Segment location on transcripts

| Transcript name | Segment starting position | Segment ending position |
|---|---|---|
| HUMNATPEP_PEA_1_T1 (SEQ ID NO: 1) | 1179 | 1396 |
| HUMNATPEP_PEA_1_T2 (SEQ ID NO: 2) | 869 | 1086 |
| HUMNATPEP_PEA_1_T3 (SEQ ID NO: 3) | 1411 | 1628 |
| HUMNATPEP_PEA_1_T4 (SEQ ID NO: 4) | 369 | 586 |

Variant protein alignment to the previously known protein:

```
Sequence name: /tmp/DbNfNQq0rT/fgacU726zu:ANFB_HUMAN
Sequence documentation:
Alignment of: HUMNATPEP_PEA_1_P2 (SEQ ID NO:13) x ANFB_HUMAN  . .
Alignment segment 1/1:
                   Quality: 1257.00                          Escore:    0
           Matching length:  129                       Total length:  129
 Matching Percent Similarity:  100.00 Matching Percent Identity: 100.00
    Total Percent Similarity:  100.00    Total Percent Identity: 100.00
                      Gaps:    0
Alignment:

1  MDPQTAPSRALLLLLFLHLAFLGGRSHPLGSPGSASDLETSGLQEQRNHL     50
      |||||||||||||||||||||||||||||||||||||||||||||||||
   1  MDPQTAPSRALLLLLFLHLAFLGGRSHPLGSPGSASDLETSGLQEQRNHL     50

51  QGKLSELQVEQTSLEPLQESPRPTGVWKSREVATEGIRGHRKMVLYTLRA    100
      |||||||||||||||||||||||||||||||||||||||||||||||||
  51  QGKLSELQVEQTSLEPLQESPRPTGVWKSREVATEGIRGHRKMVLYTLRA    100

101  PRSPKMVQGSGCFGRKMDRISSSSGLGCK                        129
      |||||||||||||||||||||||||||||
 101  PRSPKMVQGSGCFGRKMDRISSSSGLGCK                        129

Sequence name: /tmp/IeoAjU0IUc/7tSYchNtfd:ANFB_HUMAN
Sequence documentation:
Alignment of: HUMNATPEP_PEA_1_P3 (SEQ ID NO:14) x ANFB_HUMAN  . .
Alignment segment 1/1:
                   Quality: 417.00                           Escore:    0
           Matching length:   44                       Total length:   44
```

-continued

```
Matching Percent Similarity: 100.00  Matching Percent Identity: 100.00
   Total Percent Similarity: 100.00     Total Percent Identity: 100.00
                       Gaps:     0
Alignment:

1  MDPQTAPSRALLLLLFLHLAFLGGRSHPLGSPGSASDLETSGLQ    44
    |||||||||||||||||||||||||||||||||||||||||||
 1  MDPQTAPSRALLLLLFLHLAFLGGRSHPLGSPGSASDLETSGLQ    44

Sequence name: /tmp/moJ5LwI4XU/p1T8doImXi:ANFB_HUMAN
Sequence documentation:
Alignment of: HUMNATPEP_PEA_1_P7 (SEQ ID NO:15) x ANFB_HUMAN  . .
Alignment segment 1/1:
                      Quality:  415.00                      Escore:   0
               Matching length:     42                Total length:    42
   Matching Percent Similarity: 100.00  Matching Percent Identity: 100.00
      Total Percent Similarity: 100.00     Total Percent Identity: 100.00
                         Gaps:      0
Alignment:

1  MVLYTLRAPRSPKMVQGSGCFGRKMDRISSSSGLGCKVLRRH    42
    ||||||||||||||||||||||||||||||||||||||||||
93  MVLYTLRAPRSPKMVQGSGCFGRKMDRISSSSGLGCKVLRRH   134
```

SEQ ID NO:16
>HUMNATPEP_PEA_1_P2_peptide SPKMVQGS-GCFGRKMDRISSSSGLGCKGKHPLP-PRPPSPIPVCDTVRVTLGFVVSGNHTL SEQ ID NO:17
>HUMNATPEP_PEA_1_P7_peptide SPKMVQGS-GCFGRKMDRISSSSGLGCKVLRRH Expression of ANFB_HUMAN Natriuretic peptides HUMNATPEP transcripts which are detectable by amplicon as depicted in sequence name HUMNATPEPseg5 (SEQ ID NO:20) specifically in heart tissue Expression of ANFB_HUMAN Natriuretic peptides transcripts detectable by or according to seg5 node(s), HUMNATPEPseg5 (SEQ ID NO:20) amplicon(s) and HUMNATPEPseg5 (SEQ ID NO: 18) HUMNATPEPseg5 (SEQ ID NO: 19) primers was measured by real time PCR. In parallel the expression of four housekeeping genes—RPL19 (GenBank Accession No. NM_000981 (SEQ ID NO: 43); RPL19 amplicon (SEQ ID NO: 32)), TATA box (GenBank Accession No. NM_003194 (SEQ ID NO: 44); TATA amplicon (SEQ ID NO: 35)), Ubiquitin (GenBank Accession No. BC000449 (SEQ ID NO: 45); amplicon—Ubiquitin-amplicon (SEQ ID NO: 38)) and SDHA (GenBank Accession No. NM_004168 (SEQ ID NO: 46); amplicon—SDHA-amplicon (SEQ ID NO: 41)), was measured similarly. For each RT sample, the expression of the above amplicons was normalized to the geometric mean of the quantities of the housekeeping genes. The normalized quantity of each RT sample was then divided by the median of the quantities of the heart tissue samples (Sample Nos. 44-46, Table 1 above, Tissue samples in testing panel), to obtain a value of expression for each sample relative to median of the heart tissue.

Figure 4:
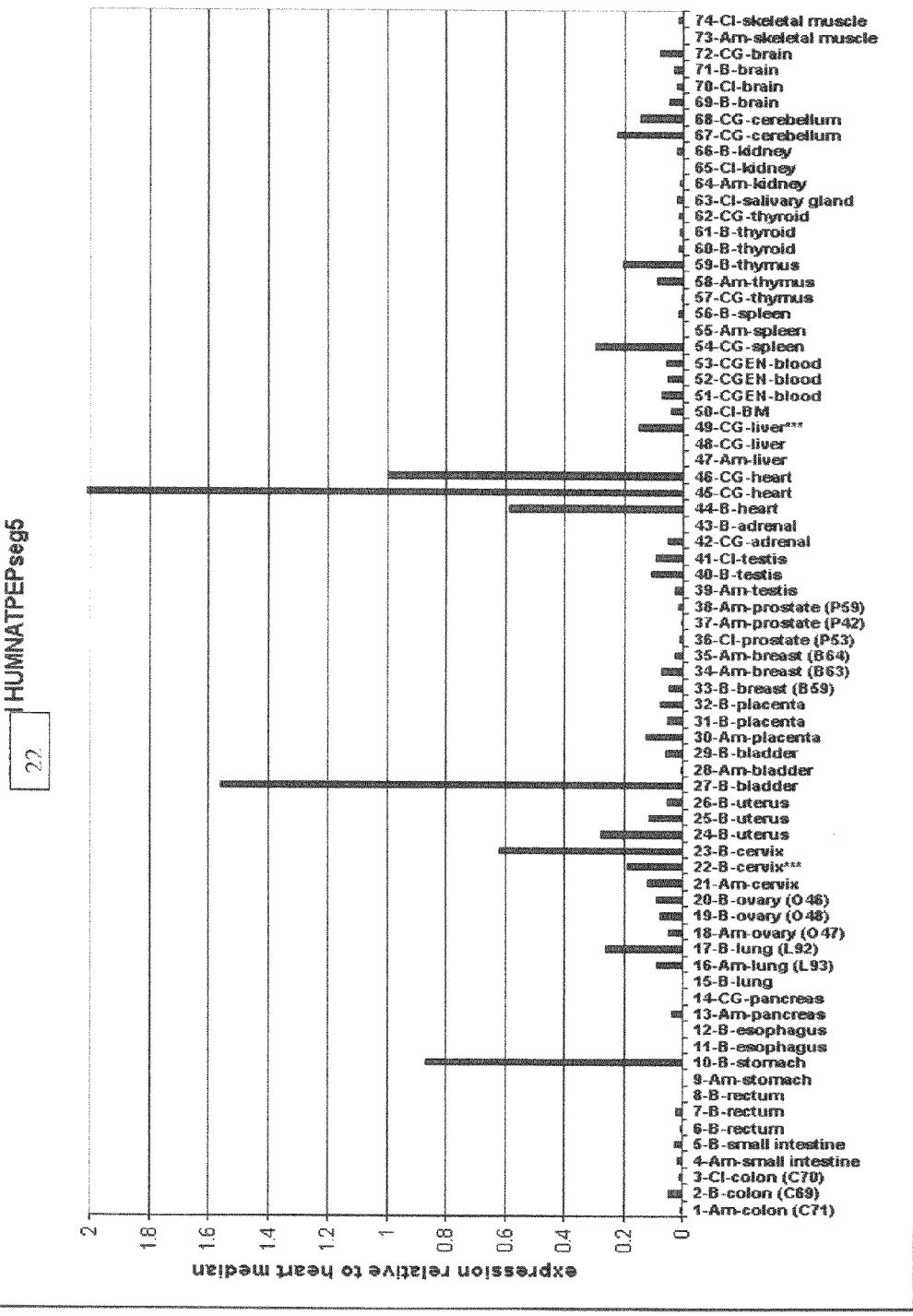

FIG. 4 is a histogram showing relative expression of the above-indicated ANFB_HUMAN Natriuretic peptides transcripts in heart tissue samples as opposed to other tissues.

As is evident from FIG. 4, the expression of ANFB_HUMAN Natriuretic peptides transcripts detectable by the above amplicon in heart tissue samples was significantly higher than in most other samples (Sample Nos. 1-9, 11-22, 24-26 ,28-43 , 47-74 Table 1, "Tissue samples in testing panel" above). Note that the expression of the above amplicon in one of the heart samples, sample no. 45, was higher compared to its expression in the other two heart samples (sample 44 and 46). Sample no. 45 is from fibrotic heart, and samples 44 and 46 are samples from normal hearts.

Primer pairs are also optionally and preferably encompassed within the present invention; for example, for the above experiment, the following primer pair was used as a non-limiting illustrative example only of a suitable primer pair: HUMNATPEPseg5 forward primer (SEQ ID NO: 18); and HUMNATPEPseg5 reverse primer (SEQ ID NO: 19).

The present invention also preferably encompasses any amplicon obtained through the use of any suitable primer pair; for example, for the above experiment, the following amplicon was obtained as a non-limiting illustrative example only of a suitable amplicon: HUMNATPEPseg5 (SEQ ID NO:20).

```
HUMNATPEPseg5 Forward primer:
                                           (SEQ ID NO:18)
CTTCCCCCATTCCAGTGTGT HUMNATPEPseg5 Reverse primer:
                                           (SEQ ID NO:19)
GAGGAAGCGATGTCCAGGTG HUMNATPEPseg5 Amplicon:
                                           (SEQ ID NO:20)
CTTCCCCCATTCCAGTGTGTGACACTGTTAGAGTCACTTTGGGGTTTGTT
GTCTCTGGGAACCACACTCTTTGAGAAAAGGTCACCTGGACATCGCTTCC
TC
```

Expression of ANFB_HUMAN Natriuretic Peptide HUMNATPEP Transcripts which are Detectable by Amplicon as Depicted in Sequence Name HUMNATPEP Seg2 (SEQ ID NO:23) Specifically in Heart Tissue Expression of ANFB_HUMAN Natriuretic peptide transcripts detectable by or according to seg2 node(s), HUMNATPEPseg2 (SEQ ID NO:23) amplicon(s) and HUMNATPEPseg2F2 (SEQ ID NO:21), HUMNATPEPseg2R2 (SEQ ID NO:22) primers was measured by real time PCR. In parallel the expression of four housekeeping genes—RPL19 (GenBank Accession No.

NM_000981 (SEQ ID NO: 43); RPL19 amplicon (SEQ ID NO: 32)), TATA box (GenBank Accession No. NM_003194 (SEQ ID NO: 44); TATA amplicon (SEQ ID NO: 35)), Ubiquitin (GenBank Accession No. BC000449 (SEQ ID NO: 45); amplicon—Ubiquitin-amplicon (SEQ ID NO: 38)) and SDHA (GenBank Accession No. NM_004168 (SEQ ID NO: 46); amplicon—SDHA-amplicon (SEQ ID NO: 41)), was measured similarly. For each RT sample, the expression of the above amplicons was normalized to the geometric mean of the quantities of the housekeeping genes. The normalized quantity of each RT sample was then divided by the median of the quantities of the heart samples (Sample Nos. 44-46, Table 1, "Tissue samples in testing panel" above), to obtain a value of expression for each sample relative to median of the heart.

Figure 5:
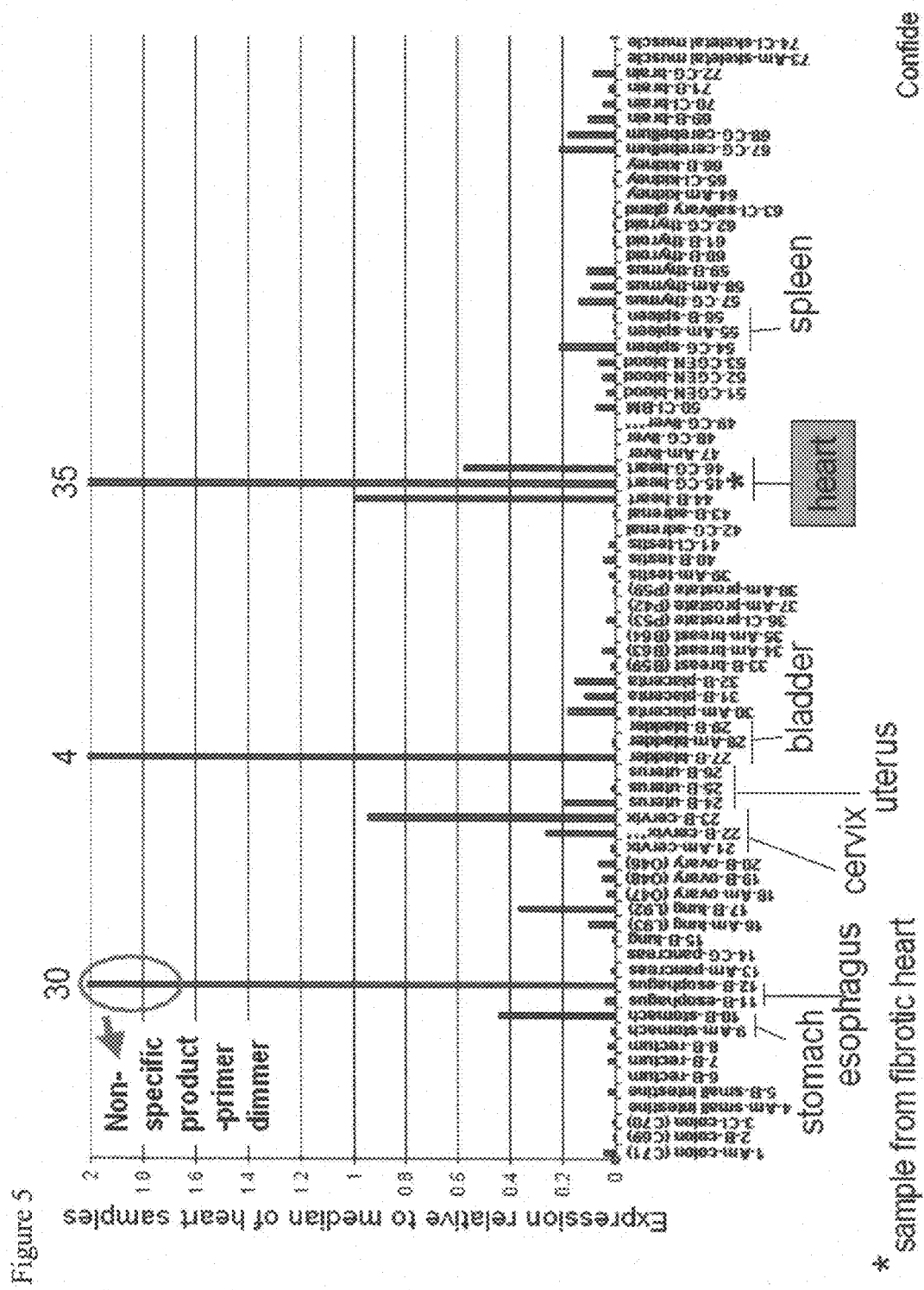

FIG. 5 is a histogram showing relative expression of the above-indicated ANFB_HUMAN Natriuretic peptides transcripts in heart tissue samples as opposed to other tissues.

As is evident from FIG. 5, the expression of ANFB_HUMAN Natriuretic peptide transcripts detectable by the above amplicon in heart tissue samples was higher than in most of the other samples (Sample Nos. 1-26, 28-43, 47-74 Table 1). Note that the expression of the above amplicon in one of the heart samples, sample no. 45, was higher compared to its expression in the other two heart samples (sample 44 and 46). Sample no. 45 is from fibrotic heart, and samples 44 and 46 are samples from normal hearts.

Primer pairs are also optionally and preferably encompassed within the present invention; for example, for the above experiment, the following primer pair was used as a non-limiting illustrative example only of a suitable primer pair: HUMNATPEPseg2F2 forward primer (SEQ ID NO:21); and HUMNATPEPseg2R2 reverse primer (SEQ ID NO:22).

The present invention also preferably encompasses any amplicon obtained through the use of any suitable primer pair; for example, for the above experiment, the following amplicon was obtained as a non-limiting illustrative example only of a suitable amplicon: HUMNATPEPseg2 (SEQ ID NO:23).

```
Forward primer HUMNATPEPseg2F2:
                                         (SEQ ID NO:21)
GCAGCAATGAAAGGGTCCTC Reverse primer HUMNATPEPseg2R2:
                                         (SEQ ID NO:22)
CATGGCACCCAAGTGAACC Amplicon HUMNATPEPseg2:
                                         (SEQ ID NO:23)
GCAGCAATGAAAGGGTCCTCACCTGCTGTCCCAAGAGGCCCTCATCTTTC
CTTTGGAATTAGTGATAAAGGAATCAGAAAATGGAGAGACTGGGTGCCCT
GACCCTGTACCCAAGGCAGTCGGTTCACTTGGGTGCCATG
```

Expression of Homo Sapiens Natriuretic Peptide Precursor B (NPPB) HUMNATPEP Transcripts which are Detectable by Amplicon as Depicted in Sequence Name HUMNATPEP seg3-4WT (SEQ ID NO:26) Specifically in Heart Tissue Expression of Homo sapiens natriuretic peptide precursor B (NPPB) transcripts detectable by or according to seg3-4 node(s), HUMNATPEP seg3-4WT (SEQ ID NO:26) amplicon(s) and primers HUMNATPEP seg3-4WT-F (SEQ ID NQ:24) and HUMNATPEP seg3-4WT-R (SEQ ID NO:25) was measured by real time PCR (this transcript relates to the known protein, or "WT" protein). In parallel the expression of four housekeeping genes—RPL19 (GenBank Accession No. NM_000981 (SEQ ID NO: 43); RPL19 amplicon (SEQ ID NO: 32)), TATA box (GenBank Accession No. NM_003194 (SEQ ID NO: 44); TATA amplicon (SEQ ID NO: 35)), Ubiquitin (GenBank Accession No. BC000449 (SEQ ID NO: 45); amplicon—Ubiquitin-amplicon (SEQ ID NO: 38)) and SDHA (GenBank Accession No. NM_004168 (SEQ ID NO: 46); amplicon—SDHA-amplicon (SEQ ID NO: 41), was measured similarly. For each RT sample, the expression of the above amplicons was normalized to the geometric mean of the quantities of the housekeeping genes. The normalized quantity of each RT sample was then divided by the median of the quantities of the heart samples (Sample Nos. 44-46, Table 1, "Tissue samples in testing panel" above), to obtain a value of expression for each sample relative to median of the heart samples.

Figure 6:
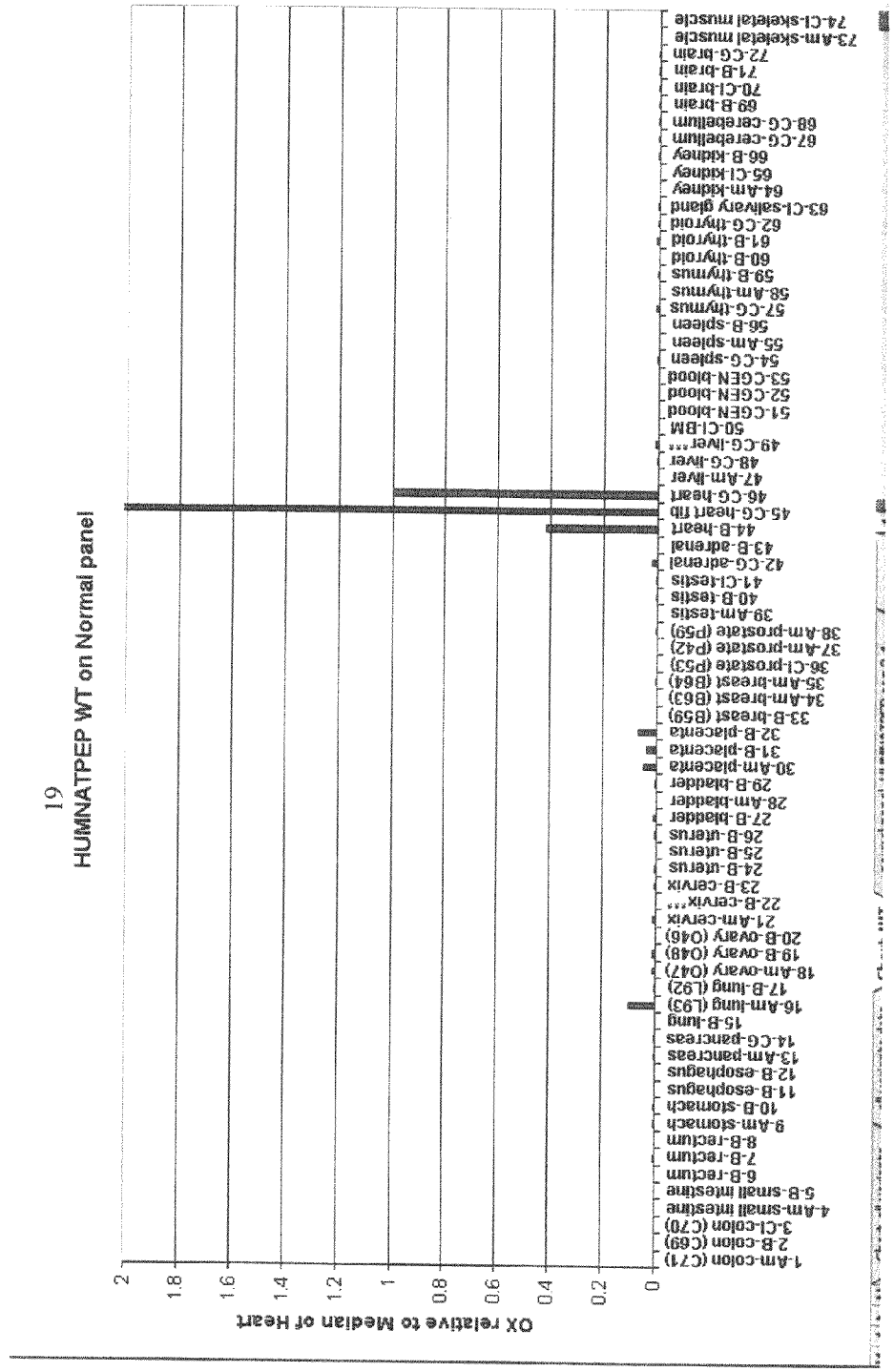

FIG. 6 is a histogram showing relative expression of the above-indicated Homo sapiens natriuretic peptide precursor B (NPPB) known protein transcripts in heart tissue samples as opposed to other tissues.

As is evident from FIG. 6, the expression of Homo sapiens natriuretic peptide precursor B (NPPB) transcripts detectable by the above amplicon(s) in heart tissue samples was higher than in the other samples (Sample Nos. 44-46 Table 1, as above). Note that the expression of the above amplicon in one of the heart samples, sample no. 45, was higher compared to its expression in the other two heart samples (sample 44 and 46). Sample no. 45 is from fibrotic heart, and samples 44 and 46 are samples from normal hearts.

Primer pairs are also optionally and preferably encompassed within the present invention; for example, for the above experiment, the following primer pair was used as a non-limiting illustrative example only of a suitable primer pair: HUMNATPEP seg3-4WT-F forward primer (SEQ ID NO:24; and HUMNATPEP seg3-4WT-R reverse primer (SEQ ID NO:25).

The present invention also preferably encompasses any amplicon obtained through the use of any suitable primer pair; for example, for the above experiment, the following amplicon was obtained as a non-limiting illustrative example only of a suitable amplicon: HUMNATPEP seg3-4WT (SEQ ID NO:26).

```
Forward primer HUMNATPEP seg3-4WT-F:
                                         (SEQ ID NO:24)
GTCCGGGTTACAGGAGCAGC Reverse primer HUMNATPEP seg3-4WT-R:
                                         (SEQ ID NO:25)
CCGCCTCAGCACTTTGCAG Amplicon HUMNATPEP seg3-4WT:
                                         (SEQ ID NO:26)
GTCCGGGTTACAGGAGCAGCGCAACCATTTGCAGGGCAAACTGTCGGAGC
TGCAGGTGGAGCAGACATCCCTGGAGCCCCTCCAGGAGAGCCCCCGTCCC
ACAGGTGTCTGGAAGTCCCGGGAGGTAGCCACCGAGGGCATCCGTGGGCA
CCGCAAAATGGTCCTCTACACCCTGCGGGCACCACGAAGCCCCAAGATGG
TGCAAGGGTCTGGCTGCTTTGGGAGGAAGATGGACCGGATCAGCTCCTCC
AGTGGCCTGGGCTGCAAAGTGCTGAGGCGG
```

Validation of expression of the transcript encoding for HUMNATPEP_PEA_1_P2 (SEQ ID NO: 13):

The validation of the above BNP splice variant transcript expression was done by performing RT-PCR amplification of 6 different RNA samples. Two postmortem pancreas tissues, three normal postmortem heart tissues and one heart tissue exhibiting focal fibrosis pathology were used (Table 9 below).

TABLE 9

| Lot no. | Source | Tissue | Pathology | Sex/Age |
|---|---|---|---|---|
| 44-B-Heart | A411077 | Biochain Heart | PB-Pool of 5M&F | |
| 45-CG-Heart | CG-255-9 | Ichilov | Heart | PM | M/75 |
| 46-CG-Heart | CG-227-1 | Ichilov | Heart | PM | F/36 |
| 13-Am-Pancreas | 071P25C | Ambion | Pancreas | PM | M/25 |
| 14-CG-Pancreas | CG-255-2 | Ichilov | Pancreas | PM | M/75 |
| Heart | CG-255-9 | Ichilov | heart | Focal fibrosis | M/75 |

RT reaction using random hexamers (Invitrogen, Cat. No. 48190-011) was performed using the standard manufacturer specifications. The primers used for RT_PCR were as follows:

```
(a) Forward primer: GTTCAGCCTCGGACTTGGAA         ("Primer A"; SEQ ID NO:27)

(b) Reverse primer: GTGACTCTAACAGTGTCACACACTGG   ("Primer B"; SEQ ID NO:28)

(c) Reverse primer (control): CCTTGTGGAATCAGAAGCAGG ("Primer C"; SEQ ID NO:29)
```

Primers A and B were used to identify the BNP variant and should produce an amplicon of length 355 bp. Primers A and C were used as a control and should produce two amplicons—the first of the wild type, with a length of 352 bp and the second of the splice variant, with a length of 893 bp.

The annealing temperature of the primers was as follows (calculated by AT/GC content):

Forward-A: 62 deg

Reverse-B 1:78 deg

Reverse 2-C: 64 deg

The RT-PCR conditions included 35 cycles of Denaturation: 94° C.-30 sec; followed by Annealing: 60° C.-30 sec; and Elongation: 72° C.-60 sec, using Taqara Hot start enzyme cat#R006A, lot#N1401.

The results shown in FIG. 7 demonstrate that although the BNP wild type product was detected by the RT-PCR in pancreas and in normal heart, expression of the BNP_T2 splice variant was detected only in the heart sample exhibiting focal fibrosis.

As can be seen from FIG. 7, BNP known transcript gene product was detected by RT-PCR in pancreas, normal heart and in heart focal fibrosis samples. The product size was as expected, about 352 bp (primers A+C). The RT_PCR reactions designed to detect the transcript for HUMNATPEP_PEA_1_P2 (SEQ ID NO: 13) splice variant were performed using primers A and B. The product of expected size (355 bp) was detected in heart focal fibrosis sample only.

Thus, without wishing to be limited by a single hypothesis, the new BNP splice variant appears to be differentially expressed in heart fibrotic tissue, and thus can be used for detection and/or quantitation of heart failure diseases and specifically cardiac fibrosis.

Example 4

Therapeutic Uses

HUMNATPEP_PEA_1_P2 (SEQ ID NO: 13) splice variant contains almost the complete sequence of known BNP (129 a.a out of 133) with the addition of unique sequence of 33 amino acids in its C-terminus. Structure-function analysis has identified the central ring structure in BNP as critical for the binding to its receptor and for its biological functions. HUMNATPEP_PEA_1_P2 (SEQ ID NO: 13) splice variant may preserve the ring structure and therefore retain the biological activity of BNP with an advantage of increased half life due to its longer size.

The variants of the present invention may optionally be used, additionally or alternatively, for therapeutic uses, including but not limited to, diuretic, natriuretic, vascular smooth muscle relaxing and vasodilation actions, and lowering blood volume and blood pressure. These variants may optionally be used for therapeutic treatment of heart failure. Preferably, the variant comprises HUMNATPEP_PEA_1_P2 (SEQ ID NO: 13) or a fragment thereof as described herein.

Coding regions on the below transcripts are shown in boldface type:

```
>HUMNATPEP_PEA_1_T1
                                              SEQ ID NO:1
AGGCGCGGAGGGGCTCATTCCCGGGCCCTGATCTCAGAGGCCCGGAATGT
GGCTGATAAATCAGAGATAACCCTGCATGGCAGGGCAGGCCCGACACTCA
GCTCCAGGATAAAAGGCCACGGTGTCCCGAGGAGCCAGGAGGAGCACCCC
GCAGGCTGAGGGCAGGTGGGAAGCAAACCCGGACGCATCGCAGCAGCAGC
AGCAGCAGCAGAAGCAGCAGCAGCAGCCTCCGCAGTCCCTCCAGAGACAT
GGATCCCCAGACAGCACCTTCCCGGGCGCTCCTGCTCCTGCTCTTCTTGC
ATCTGGCTTTCCTGGGAGGTCGTTCCCACCCGCTGGGCAGCCCCGGTTCA
GCCTCGGACTTGGAAACGTCCGGGTTACAGGAGCAGCGCAACCATTTGCA
GGGCAAACTGTCGGAGCTGCAGGTGGAGCAGACATCCCTGGAGCCCCTCC
AGGAGAGCCCCCGTCCCACAGGTGTCTGGAAGTCCCGGGAGGTAGCCACC
GAGGGCATCCGTGGGCACCGCAAAATGGTCCTCTACACCCTGCGGGCACC
ACGAAGCCCCAAGATGGTGCAAGGGTCTGGCTGCTTTGGGAGGAAGATGG
ACCGGATCAGCTCCTCCAGTGGCCTGGGCTGCAAAGGTAAGCACCCCCTG
CCACCCCGGCCGCCTTCCCCCATTCCAGTGTGTGACACTGTTAGAGTCAC
TTTGGGGTTTGTTGTCTCTGGGAACCACACTCTTTGAGAAAAGGTCACCT
GGACATCGCTTCCTCTTGTTAACAGCCTTCAGGGCCAAGGGGTGCCTTTG
TGGAATTAGTAAATGTGGGCTTATTTCATTACCATGCCCACAATACCTTC
TCCCCACCTCCTACTTCTTATCAAAGGGGCAGAATCTCCTTTGGGGGTCT
GTTTATCATTTGGCAGCCCCCCAGTGGTGCAGAAAGAGAACCAAACATTT
CCTCCTGGTTTCCTCTAAACTGTCTATAGTCTCAAAGGCAGAGAGCAGGA
TCAGCAGAGCAATGATAATCCCCAATTTACAGATGAGGAAACTGAGGCTC
AGAGAGTTGCATTAAGCCTCAAACGTCTGATGACTAACAGGGTGGTGGGT
GGCACACGATGAGGTAAGCTCAGCCCCTGCCTCCATCTCCCACCCTAACC
ATCATCACCCTCTCTCTTTCCCTGACAGTGCTGAGGCGGCATTAAGAGGA
AGTCCTGGCTGCAGACACCTGCTTCTGATTCCACAAGGGGCTTTTTCCTC
AACCCTGTGGCCGCCTTTGAAGTGACTCATTTTTTTAATGTATTTATGTA
TTTATTTGATTGTTTTATATAAGATGGTTTCTTACCTTTGAGCACAAAAT
TTCCACGGTGAAATAAAGTCAACATTATAAGCTTTATCTTTTGAAA

>HUMNATPEP_PEA_1_T2
                                              SEQ ID NO:2
AGGCGCGGAGGGGCTCATTCCCGGGCCCTGATCTCAGAGGCCCGGAATGT
GGCTGATAAATCAGAGATAACCCTGCATGGCAGGGCAGGCCCGACACTCA
GCTCCAGGATAAAAGGCCACGGTGTCCCGAGGAGCCAGGAGGAGCACCCC
GCAGGCTGAGGGCAGGTGGGAAGCAAACCCGGACGCATCGCAGCAGCAGC
AGCAGCAGCAGAAGCAGCAGCAGCAGCCTCCGCAGTCCCTCCAGAGACAT
```

```
>HUMNATPEP_PEA_1_T3
                                           SEQ ID NO:3
AGGCGCGGAGGGGCTCATTCCCGGGCCCTGATCTCAGAGGCCCGGAATGT
GGCTGATAAATCAGAGATAACCCTGCATGGCAGGGCAGGCCCGACACTCA
GCTCCAGGATAAAAGGCCACGGTGTCCCGAGGAGCCAGGAGGAGCACCCC
GCAGGCTGAGGGCAGGTGGGAAGCAAACCCGGACGCATCGCAGCAGCAGC
AGCAGCAGCAGAAGCAGCAGCAGCAGCCTCCGCAGTCCCTCCAGAGACAT
GGATCCCCAGACAGCACCTTCCCGGGCGCTCCTGCTCCTGCTCTTCTTGC
ATCTGGCTTTCCTGGGAGGTCGTTCCCACCCGCTGGGCAGCCCCGGTTCA
GCCTCGGACTTGGAAACGTCCGGGTTACAGGTGAGAGCGGAGGGCAGCTC
AGGGGGATTGGACAGCAGCAATGAAAGGGTCCTCACCTGCTGTCCCAAGA
GGCCCTCATCTTTCCTTTGGAATTAGTGATAAAGGAATCAGAAAATGGAG
AGACTGGGTGCCCTGACCCTGTACCCAAGGCAGTCGGTTCACTTGGGTGC
CATGAAGGGCTGGTGAGCCCAGGGGTGGGTCCCTGAGGCTTGGACGCCCC
CATTCATTGCAGGAGCAGCGCAACCATTTGCAGGGCAAACTGTCGGAGCT
GCAGGTGGAGCAGACATCCCTGGAGCCCCTCCAGGAGAGCCCCCGTCCCA
CAGGTGTCTGGAAGTCCCGGGAGGTAGCCACCGAGGGCATCCGTGGGCAC
CGCAAAATGGTCCTCTACACCCTGCGGGCACCACGAAGCCCCAAGATGGT
GCAAGGGTCTGGCTGCTTTGGGAGGAAGATGGACCGGATCAGCTCCTCCA
GTGGCCTGGGCTGCAAAGTGCTGAGGCGGCATTAAGAGGAAGTCCTGGCT
GCAGACACCTGCTTCTGATTCCACAAGGGGCTTTTTCCTCAACCCTGTGG
CCGCCTTTGAAGTGACTCATTTTTTTAATGTATTTATGTATTTATTTGAT
TGTTTTATATAAGATGGTTTCTTACCTTTGAGCACAAAATTTCCACGGTG
AAATAAAGTCAACATTATAAGCTTTATCTTTTGAAA

>HUMNATPEP_PEA_1_T4
                                           SEQ ID NO:4
AGGCGCGGAGGGGCTCATTCCCGGGCCCTGATCTCAGAGGCCCGGAATGT
GGCTGATAAATCAGAGATAACCCTGCATGGCAGGGCAGGCCCGACACTCA
GCTCCAGGATAAAAGGCCACGGTGTCCCGAGGAGCCAGGAGGAGCACCCC
GCAGGCTGAGGGCAGGTGGGAAGCAAACCCGGACGCATCGCAGCAGCAGC
AGCAGCAGCAGAAGCAGCAGCAGCAGCCTCCGCAGTCCCTCCGTGGGCAC
CGCAAAATGGTCCTCTACACCCTGCGGGCACCACGAAGCCCCAAGATGGT
GCAAGGGTCTGGCTGCTTTGGGAGGAAGATGGACCGGATCAGCTCCTCCA
GTGGCCTGGGCTGCAAAGTGCTGAGGCGGCATTAAGAGGAAGTCCTGGCT
GCAGACACCTGCTTCTGATTCCACAAGGGGCTTTTTCCTCAACCCTGTGG
CCGCCTTTGAAGTGACTCATTTTTTTAATGTATTTATGTATTTATTTGAT
TGTTTTATATAAGATGGTTTCTTACCTTTGAGCACAAAATTTCCACGGTG
AAATAAAGTCAACATTATAAGCTTTATCTTTTGAAA
```

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An isolated polypeptide comprising the amino acid sequence of SEQ ID NO:14.

\* \* \* \* \*